US012589014B2

(12) United States Patent
Franano et al.

(10) Patent No.: US 12,589,014 B2
(45) Date of Patent: Mar. 31, 2026

(54) EXPANDABLE BODY DEVICE AND METHOD OF USE

(71) Applicant: ARTIO MEDICAL, INC., Prairie Village, KS (US)

(72) Inventors: F. Nicholas Franano, Olathe, KS (US); Katherine Stephenson, Los Gatos, CA (US)

(73) Assignee: Artio Medical, Inc., Prairie Village, KS (US)

( * ) Notice: Subject to any disclaimer, the term of this patent is extended or adjusted under 35 U.S.C. 154(b) by 923 days.

(21) Appl. No.: 17/329,756

(22) Filed: May 25, 2021

(65) Prior Publication Data

US 2021/0275187 A1     Sep. 9, 2021

Related U.S. Application Data

(60) Division of application No. 14/372,967, filed as application No. PCT/US2012/047072 on Jul. 17, (Continued)

(51) Int. Cl.
*A61B 17/12* (2006.01)
*A61F 2/06* (2013.01)
(Continued)

(52) U.S. Cl.
CPC ........ *A61F 2/958* (2013.01); *A61B 17/12031* (2013.01); *A61B 17/12109* (2013.01);
(Continued)

(58) Field of Classification Search
CPC ........ A61B 17/12109; A61B 17/12113; A61B 17/12136; A61B 2017/12054;
(Continued)

(56) References Cited

U.S. PATENT DOCUMENTS 4,327,734 A     5/1982   White, Jr.
4,364,392 A     12/1982   Strother et al.
(Continued)

FOREIGN PATENT DOCUMENTS

EP          2665508 A2     11/2018
JP       2001510692 A       8/2001
(Continued)

OTHER PUBLICATIONS

Office Action for Canadian Application No. 3,049,059, issued Feb. 17, 2022 (03 Pages).
(Continued)

*Primary Examiner* — Todd J Scherbel
(74) *Attorney, Agent, or Firm* — Polsinelli PC

(57) ABSTRACT

Disclosed herein are medical devices comprising a single-lobed, thin-walled, expandable body ("ballstent" or "block-stent") and a flexible, elongated delivery device ("delivery catheter") and systems and methods of use for treating saccular vascular aneurysms and methods of use for occluding segments of blood vessels and other biological conduits. Expandable bodies comprising gold, platinum, or silver that can be compressed, positioned in the lumen of an aneurysm or blood vessel, and expanded to conform to the shape of the aneurysm or segment of blood vessel or biological conduit are disclosed. The external surface of the expandable bodies can be configured to promote local thrombosis and to promote the growth of tissue into and around the wall in order to reduce migration of the expandable body and to occlude and seal the aneurysm or biological conduit. The wall of the expandable bodies can also be configured to release drugs or pharmacologically active molecules, such as those that promote thrombosis, cell proliferation, extracellular matrix deposition, or tissue ingrowth.

18 Claims, 52 Drawing Sheets

Related U.S. Application Data 2012, now Pat. No. 11,013,516, which is a continuation-in-part of application No. PCT/US2012/021620, filed on Jan. 17, 2012, and a continuation-in-part of application No. PCT/US2012/021621, filed on Jan. 17, 2012, which is a continuation-in-part of application No. PCT/US2012/000030, filed on Jan. 17, 2012.

(60) Provisional application No. 61/433,305, filed on Jan. 17, 2011.

(51) Int. Cl.

| | |
|---|---|
| *A61F 2/958* | (2013.01) |
| *A61M 25/10* | (2013.01) |
| *A61B 17/00* | (2006.01) |
| *A61B 17/22* | (2006.01) |
| *A61B 90/00* | (2016.01) |

(52) U.S. Cl.
CPC .. *A61B 17/12113* (2013.01); *A61B 17/12131* (2013.01); *A61B 17/12136* (2013.01); *A61B 17/12172* (2013.01); *A61F 2/06* (2013.01); *A61M 25/1029* (2013.01); *A61B 2017/00004* (2013.01); *A61B 2017/00526* (2013.01); *A61B 2017/00849* (2013.01); *A61B 2017/00867* (2013.01); *A61B 2017/00884* (2013.01); *A61B 2017/00893* (2013.01); *A61B 2017/12054* (2013.01); *A61B 2017/12059* (2013.01); *A61B 2017/12063* (2013.01); *A61B 2017/12068* (2013.01); *A61B 2017/12077* (2013.01); *A61B 17/1214* (2013.01); *A61B 17/12177* (2013.01); *A61B 17/12181* (2013.01); *A61B 2017/22038* (2013.01); *A61B 2090/037* (2016.02); *A61B 2090/3966* (2016.02); *Y10T 29/49826* (2015.01)

(58) Field of Classification Search
CPC . A61B 2017/12063; A61B 2017/12059; A61F 2/958
See application file for complete search history.

(56) References Cited

U.S. PATENT DOCUMENTS

| | | | |
|---|---|---|---|
| 4,395,806 | A | 8/1983 | Wonder et al. |
| 5,181,921 | A | 1/1993 | Makita et al. |
| 5,334,210 | A | 8/1994 | Gianturco |
| 5,704,908 | A | 1/1998 | Hofmann et al. |
| 5,779,672 | A | 7/1998 | Dormandy, Jr. |
| 6,231,572 | B1 | 5/2001 | Hart et al. |
| 7,632,291 | B2 | 12/2009 | Stephens et al. |
| 2002/0082638 | A1* | 6/2002 | Porter ................ A61B 17/1219 |
| | | | 606/195 |
| 2003/0018388 | A1 | 1/2003 | Comer |
| 2003/0074084 | A1 | 4/2003 | Nakao |
| 2010/0160949 | A1 | 6/2010 | Takuma |

FOREIGN PATENT DOCUMENTS

| | | | |
|---|---|---|---|
| JP | 2004520881 | A | 7/2004 |
| JP | 2004536672 | A | 12/2004 |
| JP | 2007533360 | A | 11/2007 |
| WO | 98/57586 | A1 | 12/1998 |
| WO | 99/03404 | A1 | 1/1999 |
| WO | 00/27292 | A1 | 5/2000 |
| WO | 00/72909 | A1 | 12/2000 |
| WO | 01/12104 | A1 | 2/2001 |
| WO | 01/15608 | A1 | 3/2001 |
| WO | 02/051320 | A2 | 7/2002 |
| WO | 02/087449 | A1 | 11/2002 |
| WO | 03/011363 | A2 | 2/2003 |
| WO | 2004/112656 | A2 | 12/2004 |
| WO | 2012/099704 | A2 | 7/2012 |

OTHER PUBLICATIONS

Office Action for Israel Application No. 274404, issued on Dec. 27, 2021, 08 Pages (4 Pages of Official Copy and 4 Pages of English Translation).
Office Action for Japanese Application No. 2020-162388, issued on Jul. 19, 2022, 05 Pages (2 Pages of Official Copy and 3 Pages of English Translation).
Office Action from related European Patent Application No. 18182792.4, dated Mar. 11, 2022; 7 pgs.
Office Action from related Japanese Patent Application No. 2020-162388, dated Aug. 24, 2021 (English translation); 4 pgs.

* cited by examiner

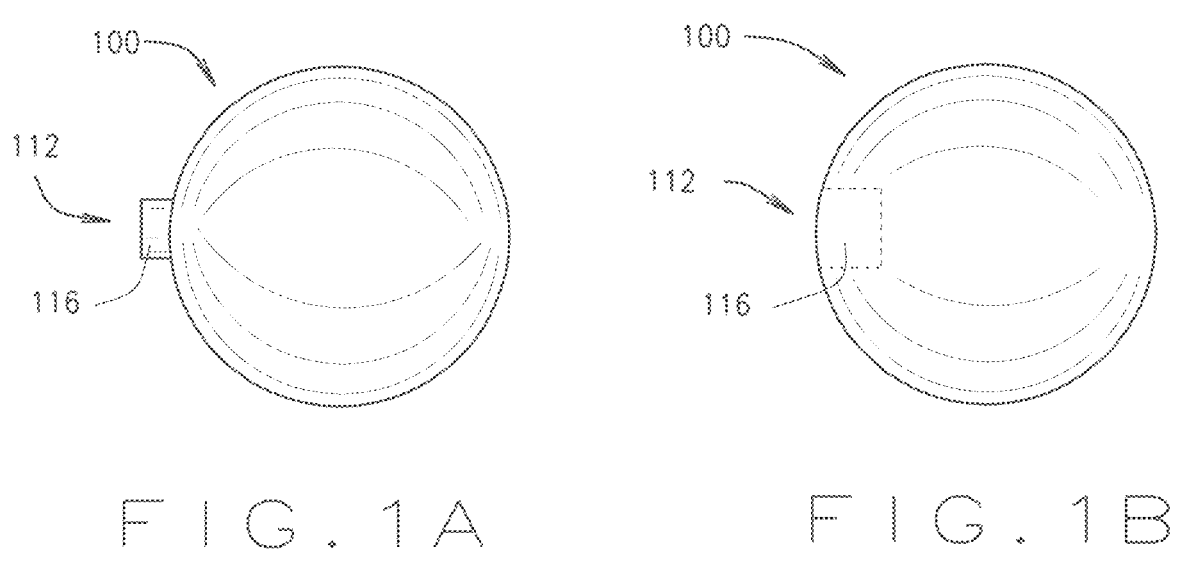
F I G . 1 A          F I G . 1 B
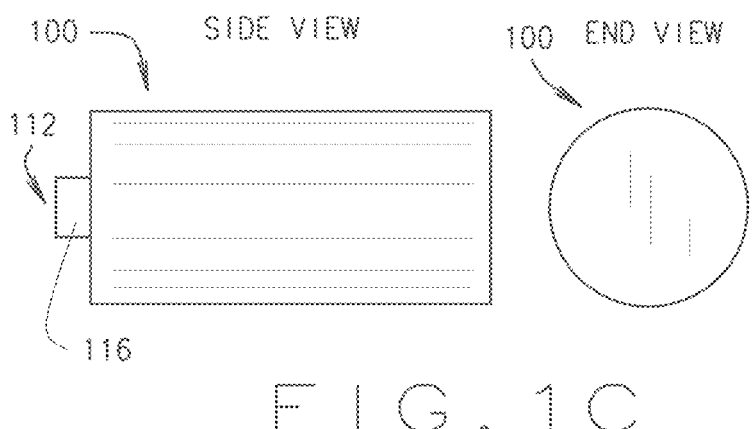
F I G . 1 C
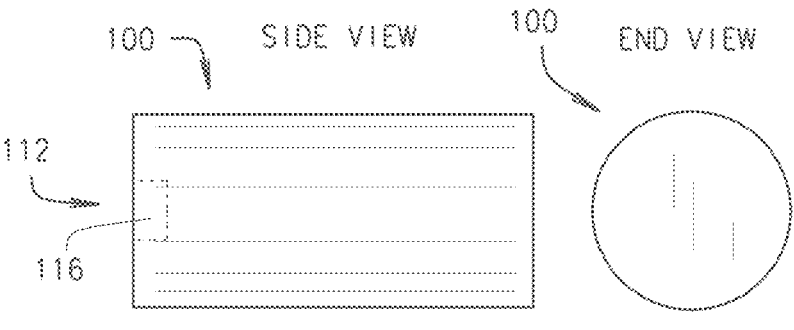
F I G . 1 D

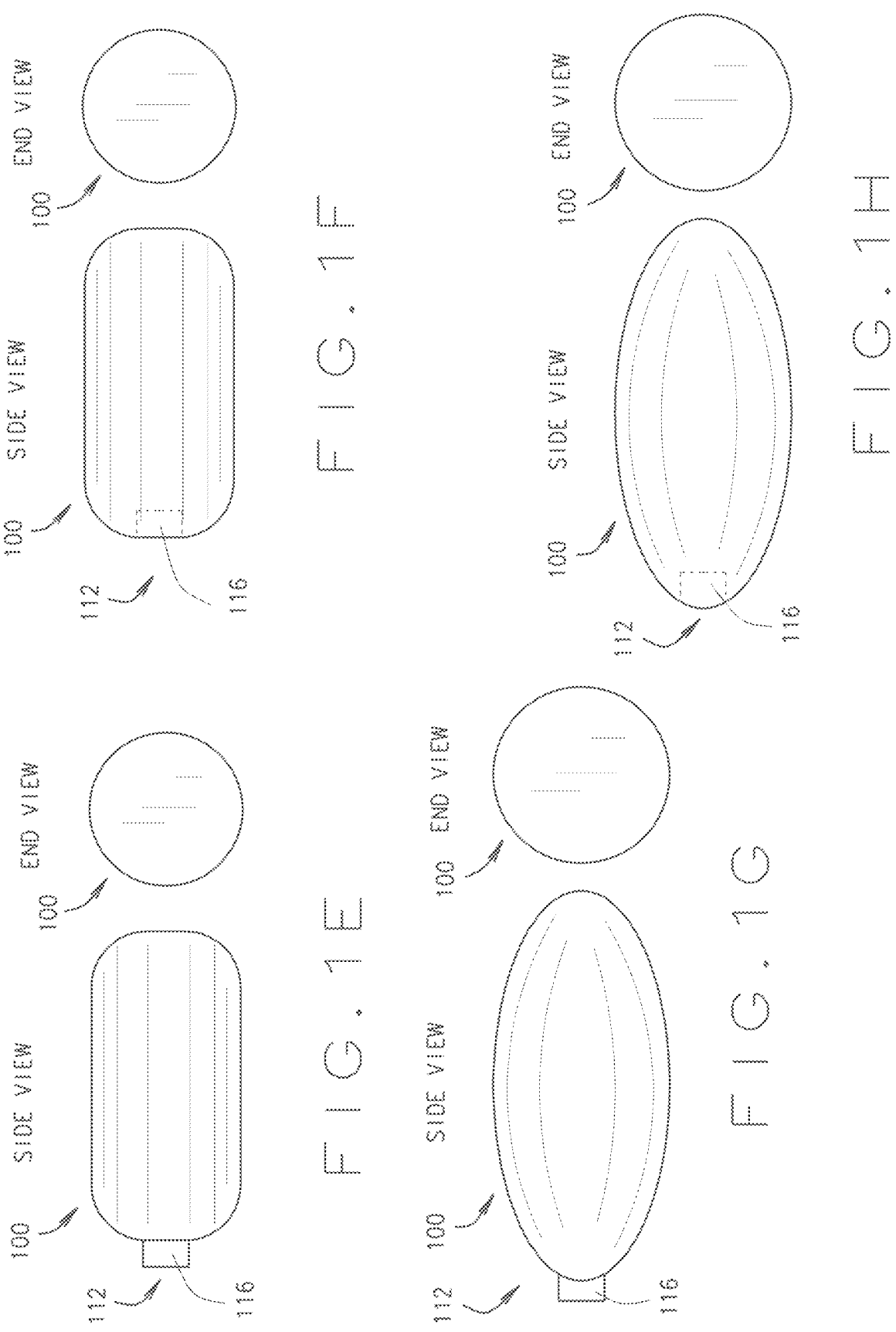

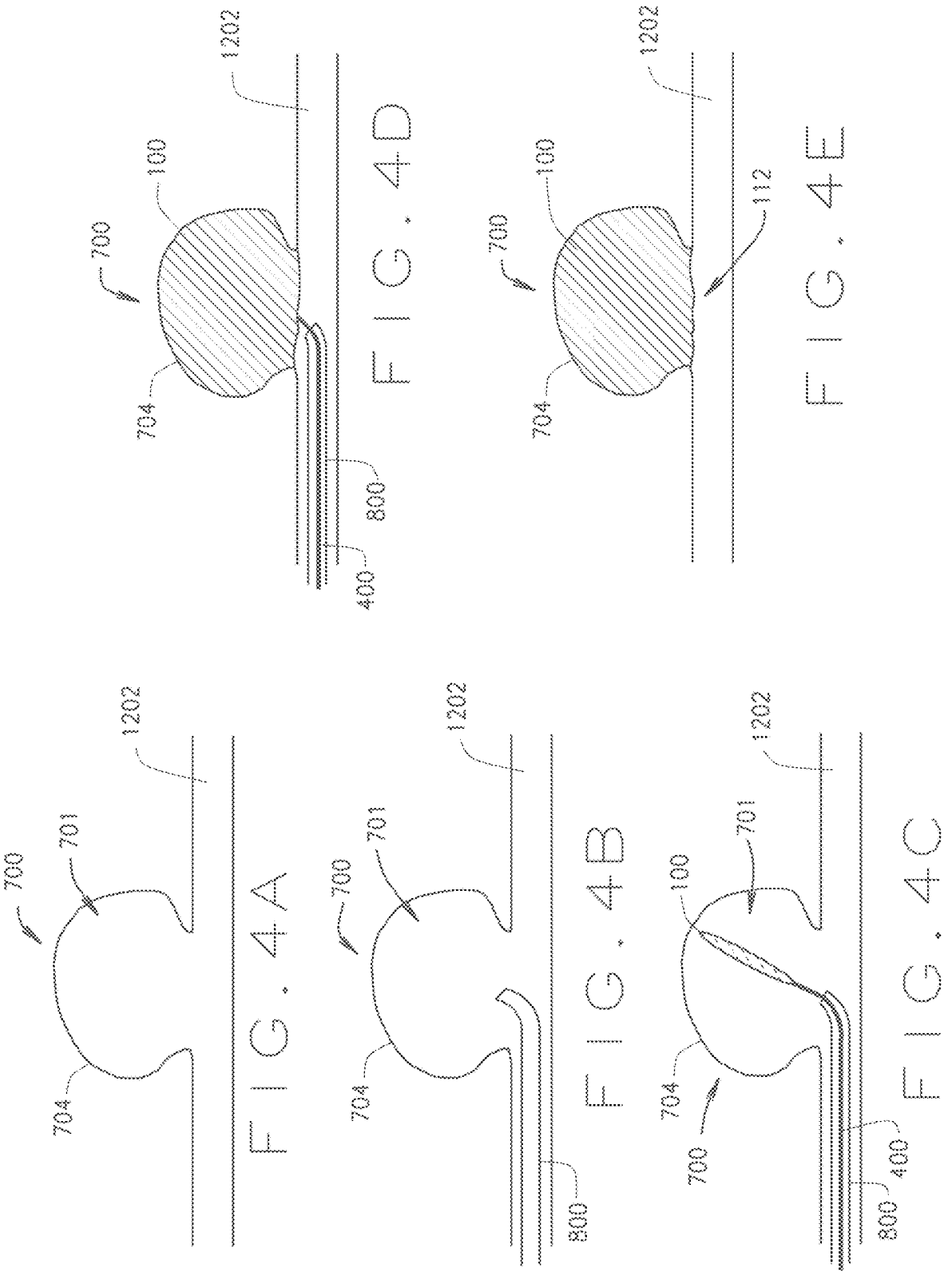

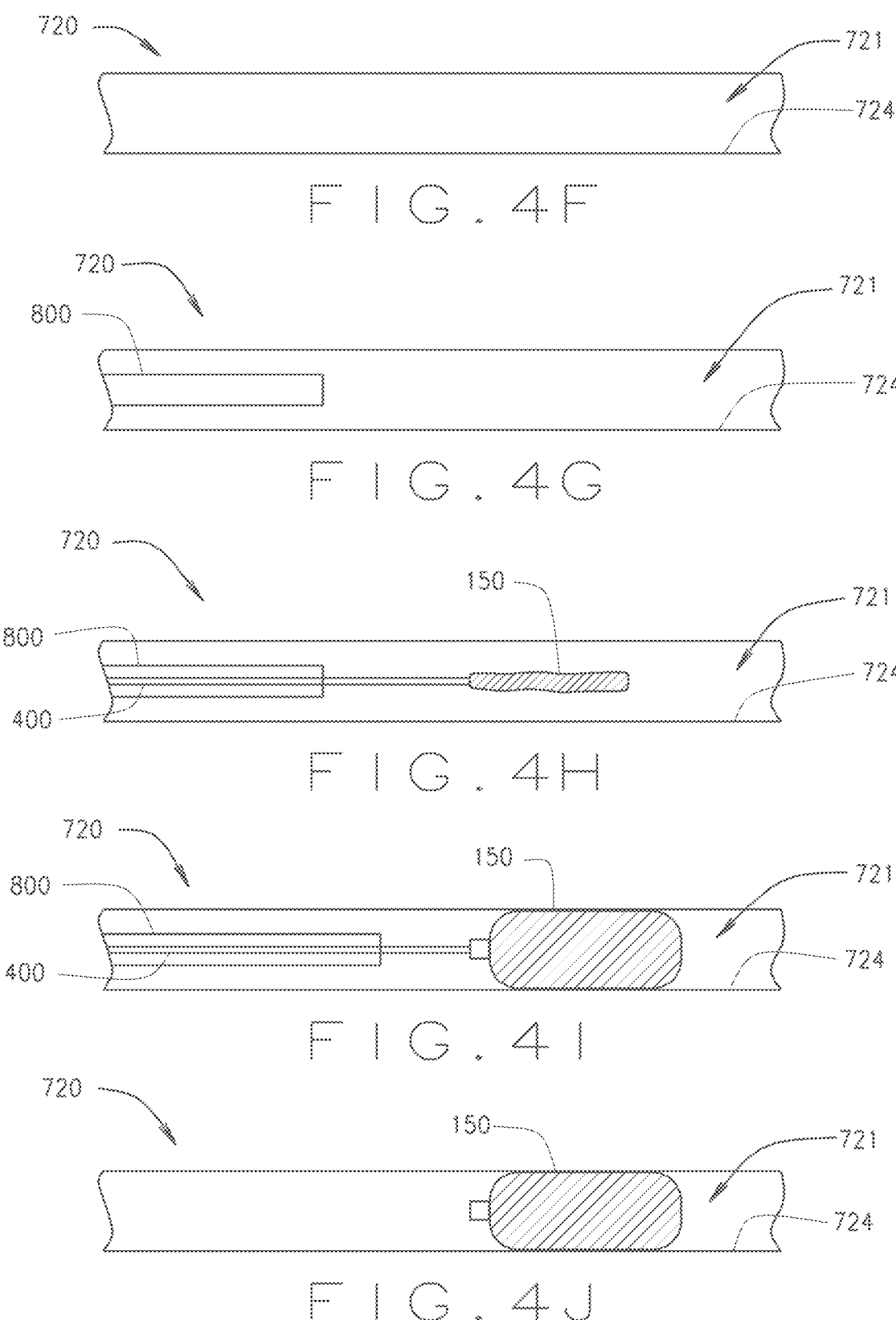
F I G . 4 F
F I G . 4 G
F I G . 4 H
F I G . 4 I
F I G . 4 J

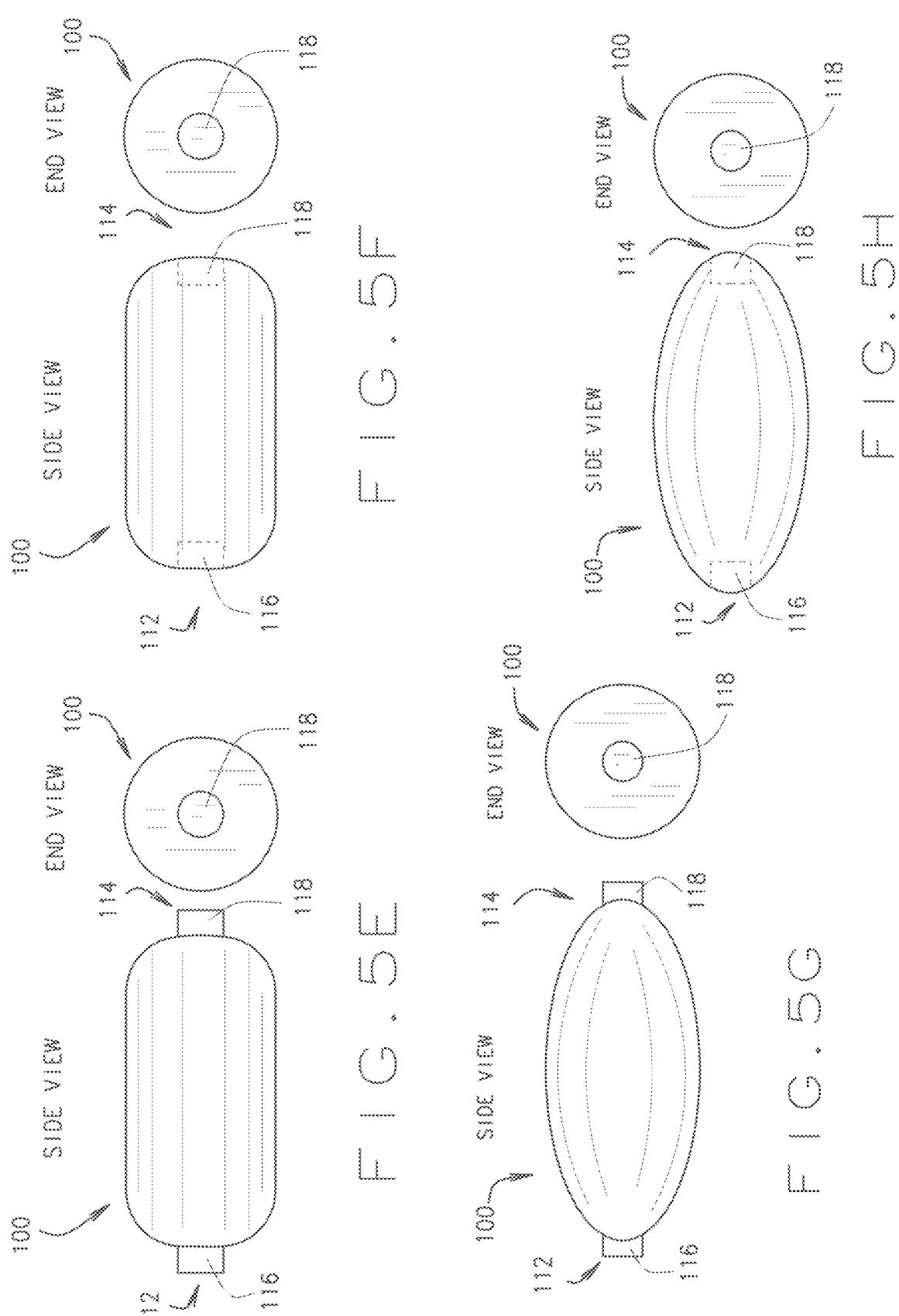

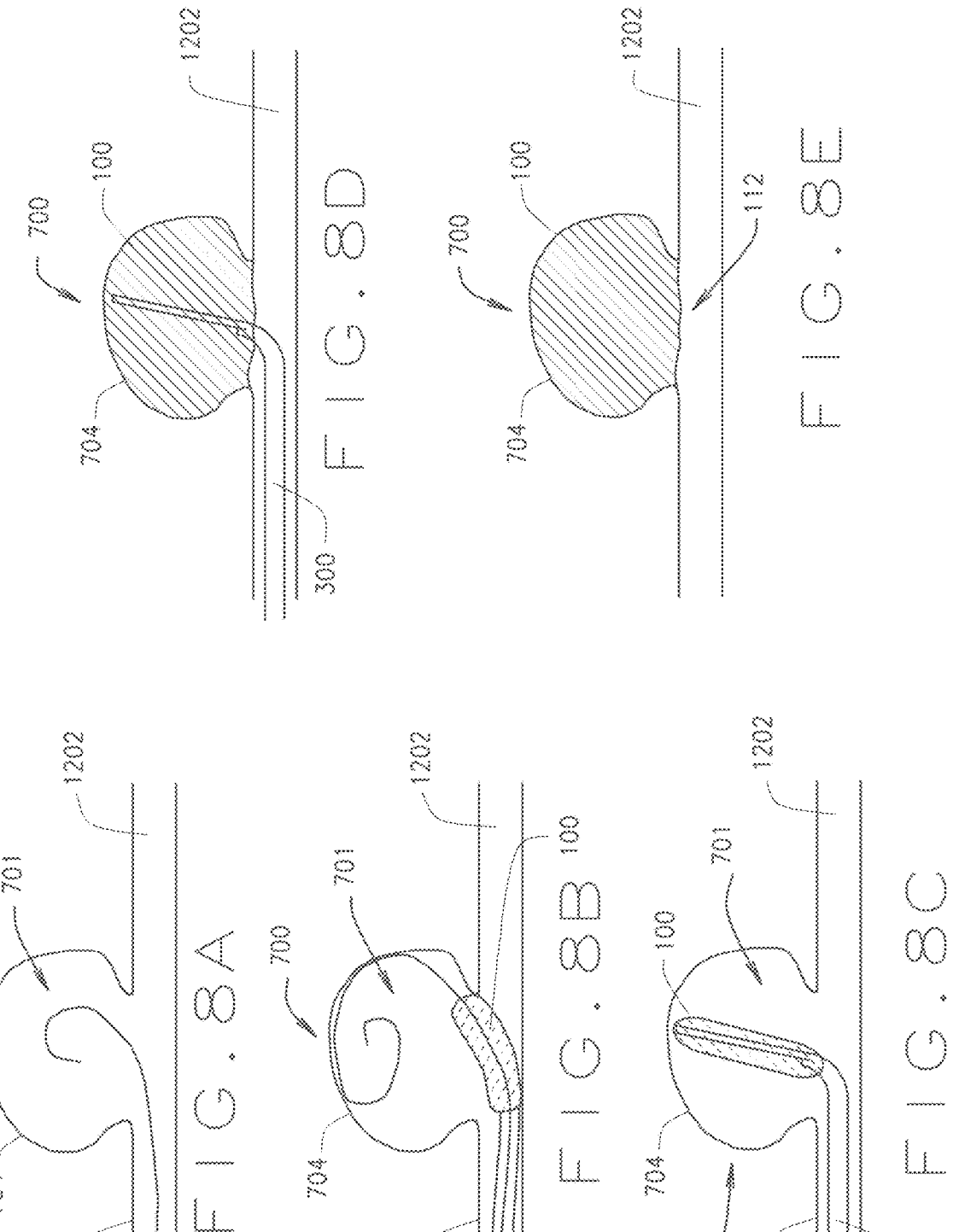

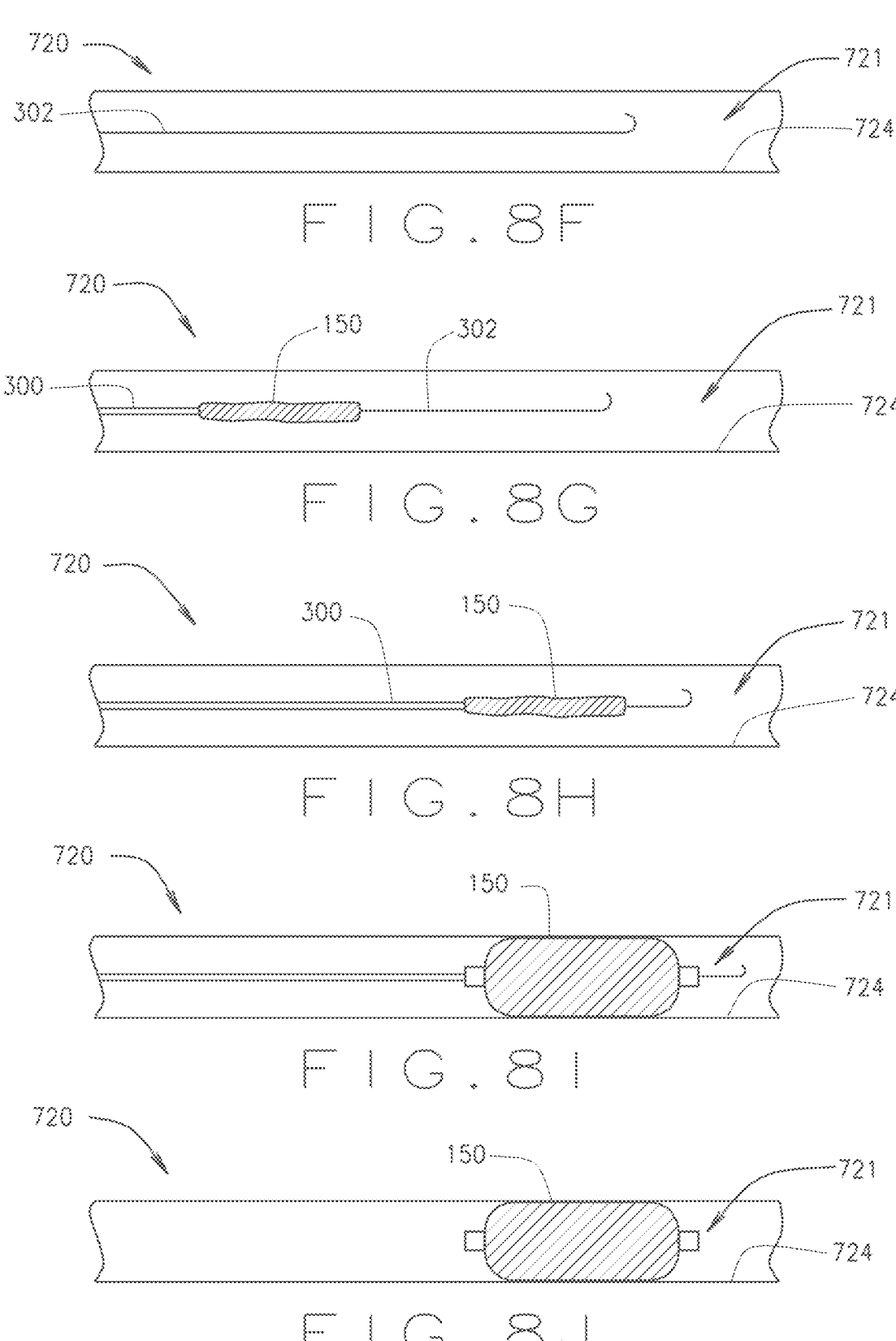
F I G . 8F
F I G . 8G
F I G . 8H
F I G . 8I
F I G . 8J

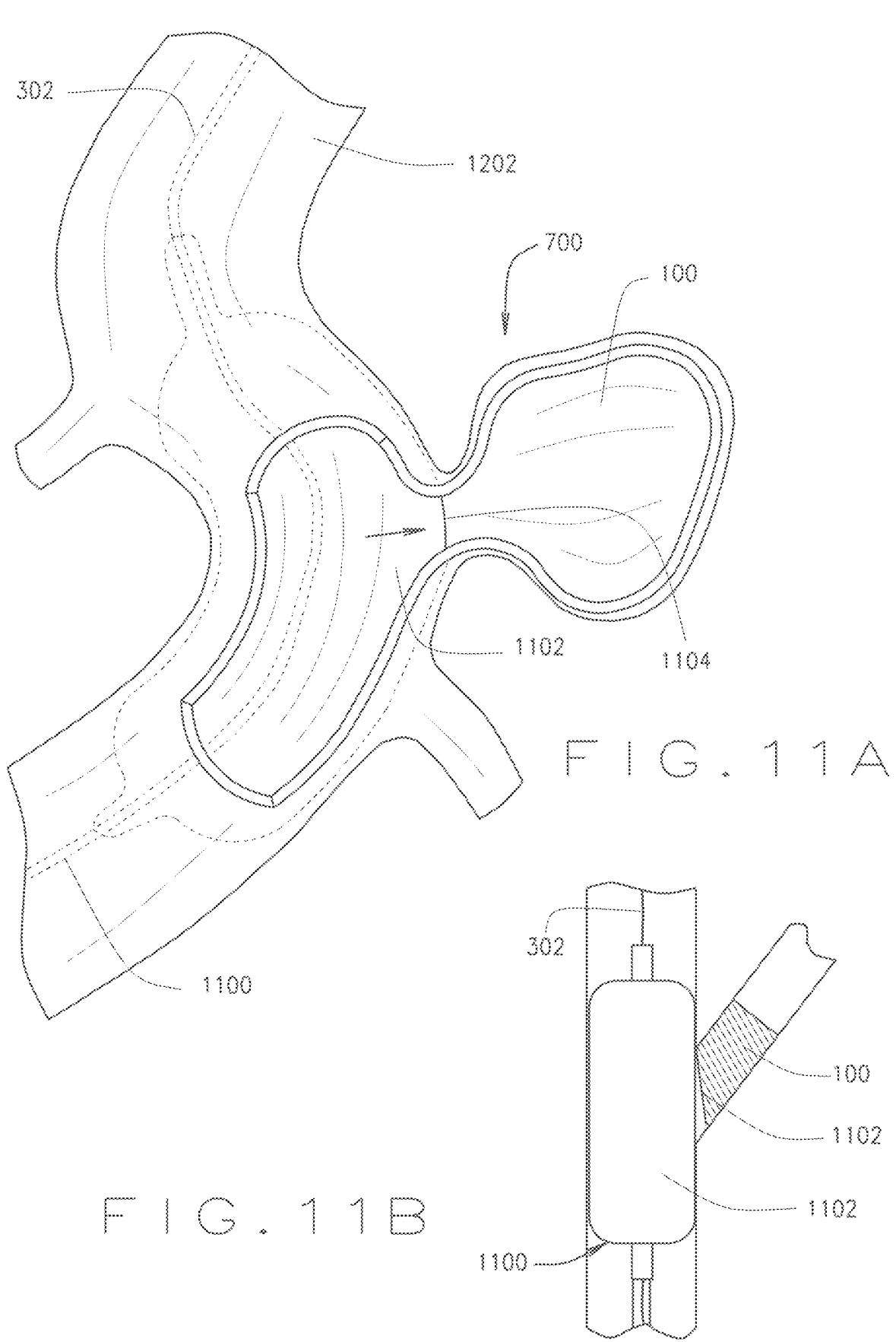
F I G . 1 1 A
F I G . 1 1 B

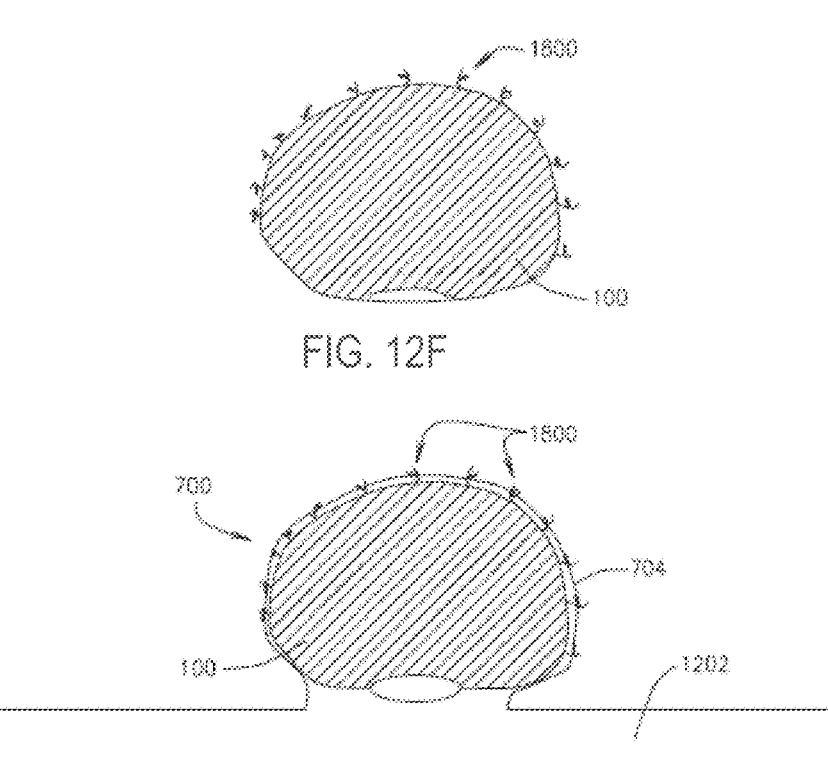
FIG. 12F
FIG. 12G
FIG. 12H
FIG. 12I
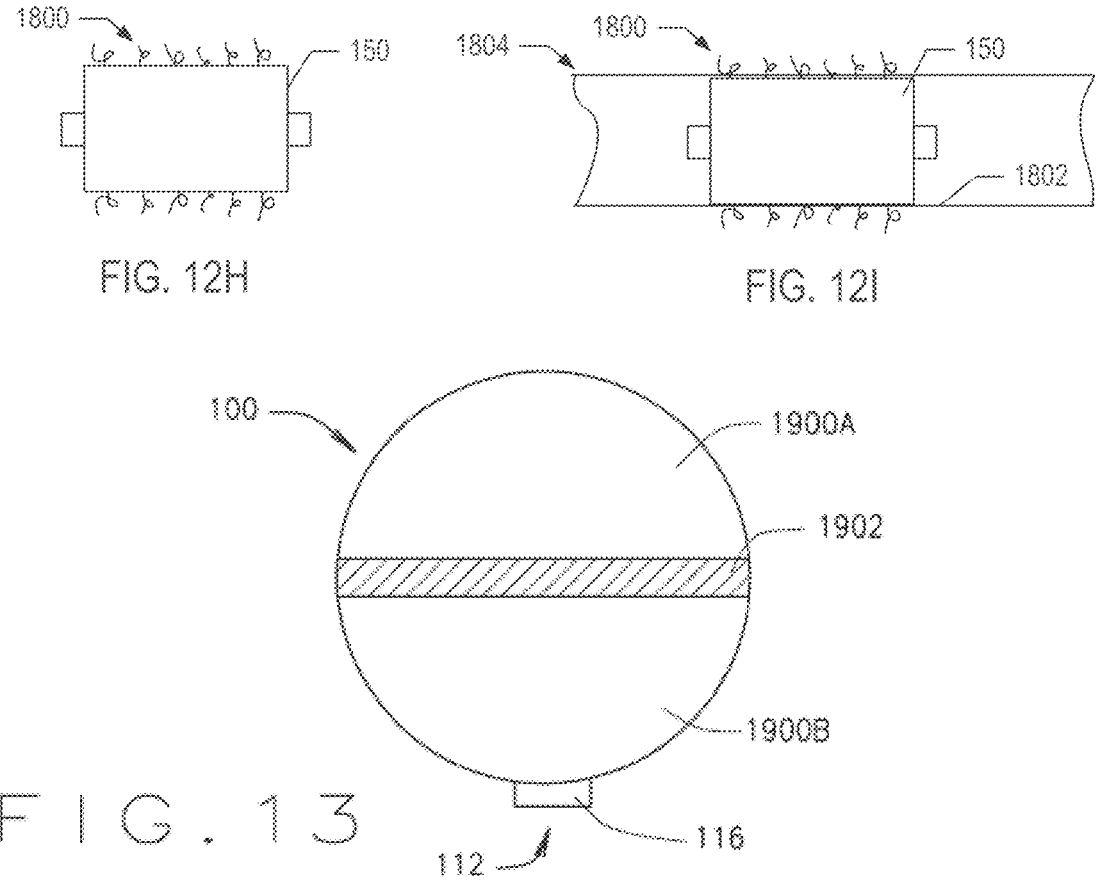
FIG. 13

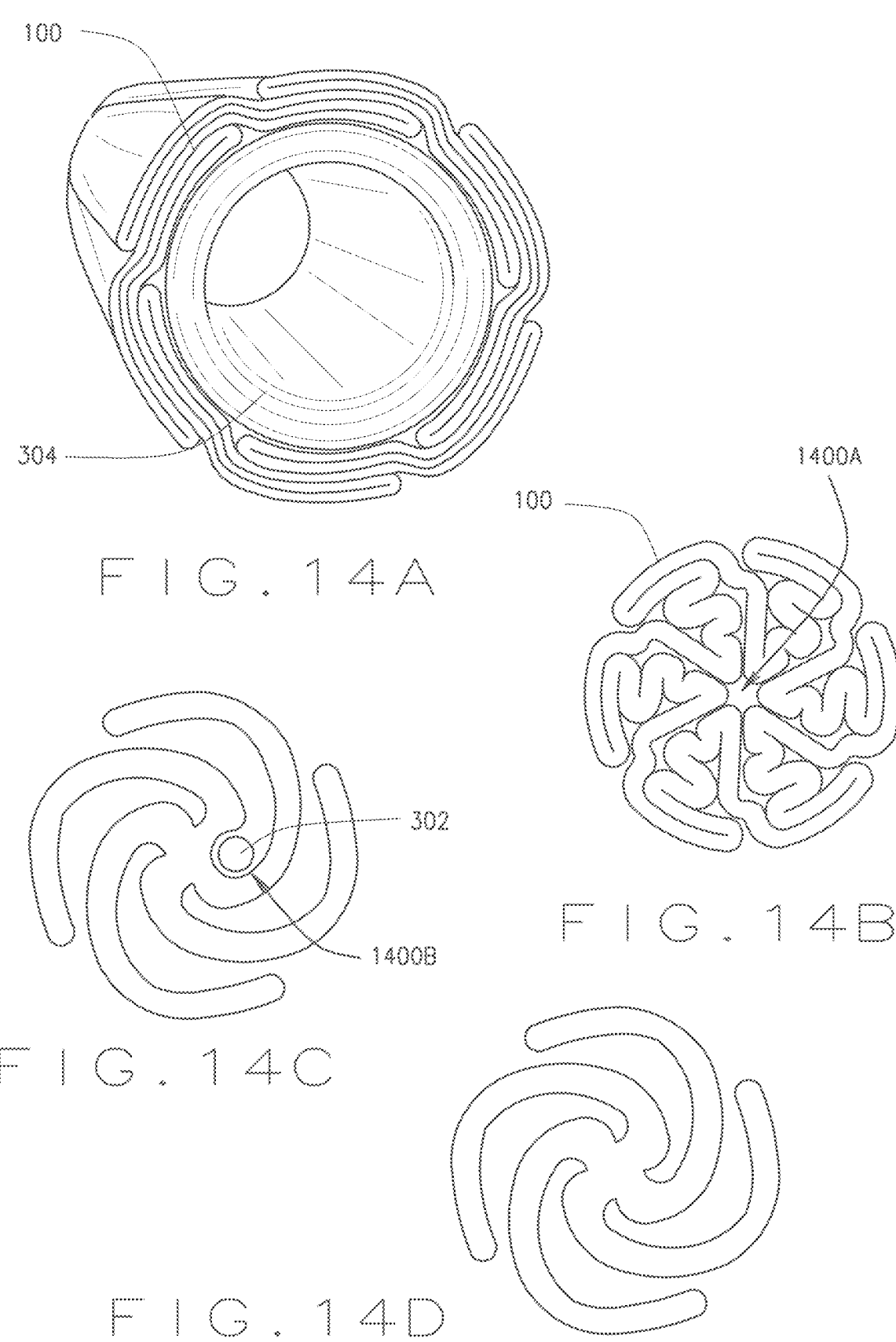
F I G . 1 4 A
F I G . 1 4 B
F I G . 1 4 C
F I G . 1 4 D

TABLE OF EXEMPLARY DIMENSIONS

ROUND BALLOON DIMENSIONS

| | Parameter | Units | MIN | MAX |
|---|---|---|---|---|
| PREFERRED | EXTERNAL LAYER THICKNESS | µm | 1.00 | 55.00 |
| FULL RANGE | EXTERNAL LAYER THICKNESS | µm | 0.50 | 60.00 |
| PREFERRED | EXTERNAL LAYER PORE DIAMETER | µm | 1.00 | 30.00 |
| FULL RANGE | EXTERNAL LAYER PORE DIAMETER | µm | 9.50 | 100.00 |
| PREFERRED | TOTAL WALL THICKNESS | µm | 3.00 | 10.00 |
| FULL RANGE | TOTAL WALL THICKNESS | µm | 3.00 | 60.00 |
| PREFERRED | VOLUME | cc | 0.004 | 0.52 |
| FULL RANGE | VOLUME | cc | 0.004 | 14.14 |
| PREFERRED | COMPRESSED DIAMETER | mm | 0.95 | 1.62 |
| FULL RANGE | COMPRESSED DIAMETER | mm | 0.65 | 2.25 |
| PREFERRED | EXPANDED DIAMETER | mm | 2.00 | 10.00 |
| FULL RANGE | EXPANDED DIAMETER | mm | 2.00 | 30.00 |

ROUND BALLOON DIMENSIONS

| | Parameter | Units | MIN | MAX |
|---|---|---|---|---|
| PREFERRED | INVERT NECK DIAMETER | mm | 0.25 | 2.00 |
| FULL RANGE | INVERT NECK DIAMETER | mm | 0.10 | 10.00 |
| PREFERRED | INVERT NECK LENGTH | mm | 1.00 | 4.00 |
| FULL RANGE | INVERT NECK LENGTH | mm | 0.50 | 10.00 |
| PREFERRED | NECK LENGTH | mm | 0.50 | 2.00 |
| FULL RANGE | NECK LENGTH | mm | 0.50 | 60.00 |
| PREFERRED | NECK OPENING DIAMETER | mm | 0.25 | 5.00 |
| FULL RANGE | NECK OPENING DIAMETER | mm | 0.10 | 20.00 |
| PREFERRED | INNER LAYER THICKNESS | µm | 1.00 | 2.00 |
| FULL RANGE | INNER LAYER THICKNESS | µm | 0.50 | 2.00 |

FIG. 30A

GUIDE WIRE

| | | | UNITS | mm | mm |
|---|---|---|---|---|---|
| PREFERRED | EXTERNAL DIAMETER | | | 0.65 | 1.57 |
| FULL RANGE | EXTERNAL DIAMETER | | UNITS | mm | mm |
| | | | | MIN 0.10 | MAX 2.15 |

TABLE OF EXEMPLARY DIMENSIONS

OBLONG BALLOON DIMENSIONS

| | | UNITS | cc | cc |
|---|---|---|---|---|
| PREFERRED | VOLUME | | 0.004 | 16.76 |
| FULL RANGE | VOLUME | UNITS | cc | cc |
| | | | 0.001 | 523.80 |
| PREFERRED | LENGTH | UNITS | mm | mm |
| | | | 2.00 | 60.00 |
| FULL RANGE | LENGTH | UNITS | mm | mm |
| | | | 2.00 | 100.00 |
| PREFERRED | EXPANDED DIAMETER | UNITS | mm | mm |
| | | | 2.00 | 20.00 |
| FULL RANGE | EXPANDED DIAMETER | UNITS | mm | mm |
| | | | MIN 1.00 | MAX 100.00 |

DELIVERY CATHETER DIMENSIONS

| | | UNITS | mm | mm |
|---|---|---|---|---|
| PREFERRED | LENGTH | | 75.00 | 225.00 |
| FULL RANGE | LENGTH | UNITS | mm | mm |
| | | | 5.00 | 300.00 |
| PREFERRED | SINGLE CENTRAL LUMEN DIAMETER | UNITS | mm | mm |
| | | | 0.70 | 1.57 |
| FULL RANGE | SINGLE CENTRAL LUMEN DIAMETER | UNITS | mm | mm |
| | | | 0.45 | 2.20 |
| PREFERRED | WALL THICKNESS | UNITS | mm | mm |
| | | | 0.05 | 0.15 |
| FULL RANGE | WALL THICKNESS | UNITS | mm | mm |
| | | | 0.05 | 0.50 |
| PREFERRED | EXTERNAL DIAMETER | UNITS | mm | mm |
| | | | 1.00 | 1.67 |
| FULL RANGE | EXTERNAL DIAMETER | UNITS | mm | mm |
| | | | MIN 0.70 | MAX 7.30 |

FIG. 30B

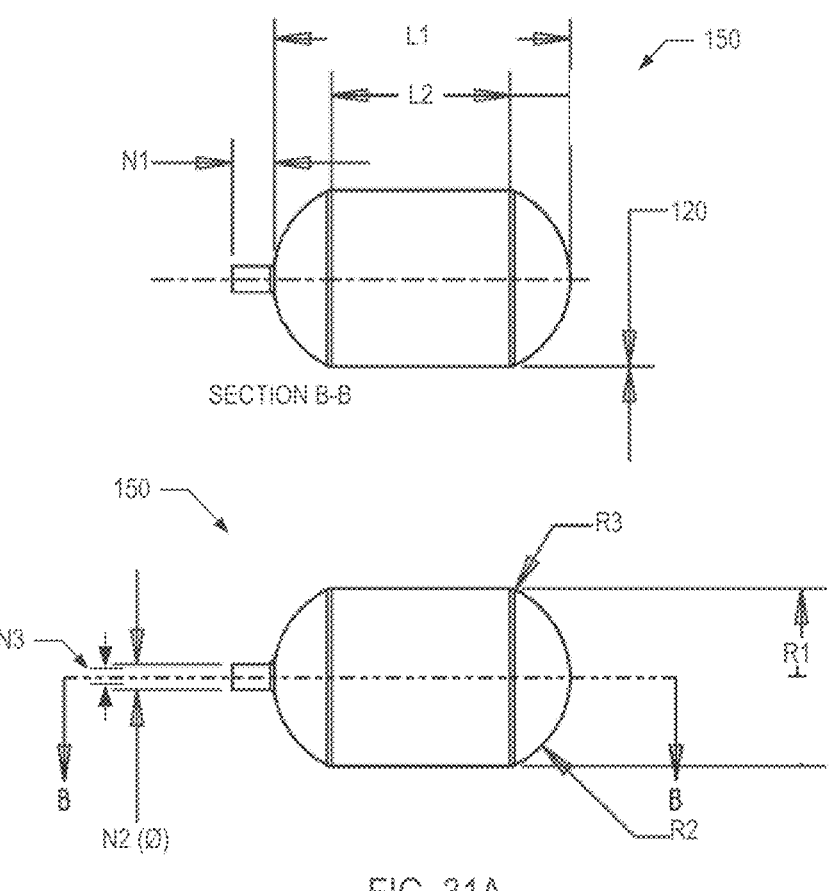
SECTION B-B
FIG. 31A
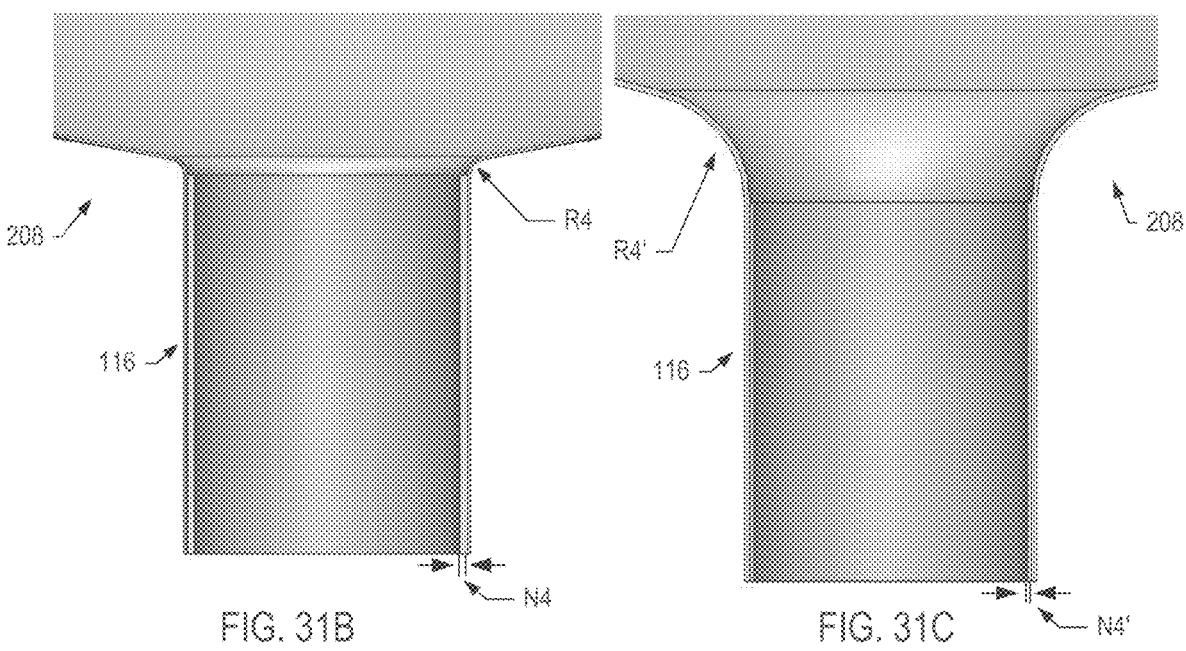
FIG. 31B
FIG. 31C

SECTION A-A

Section B-B

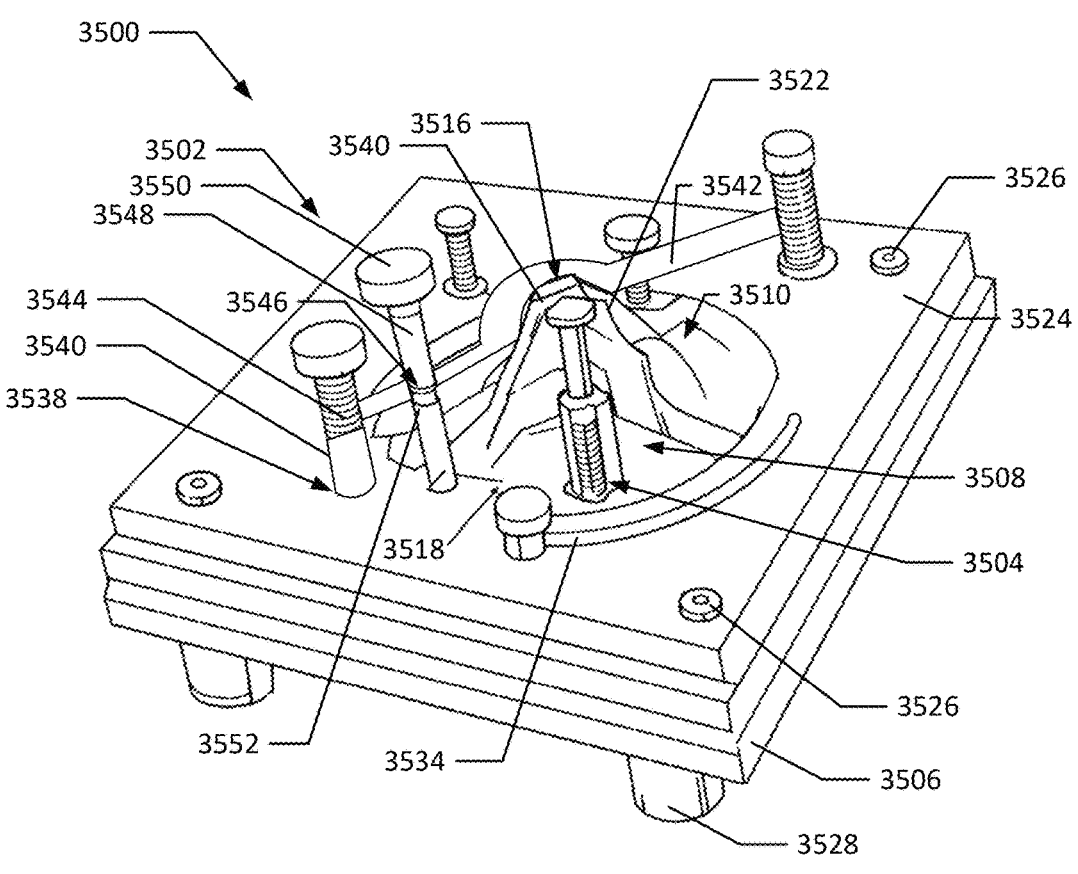
FIG. 41C
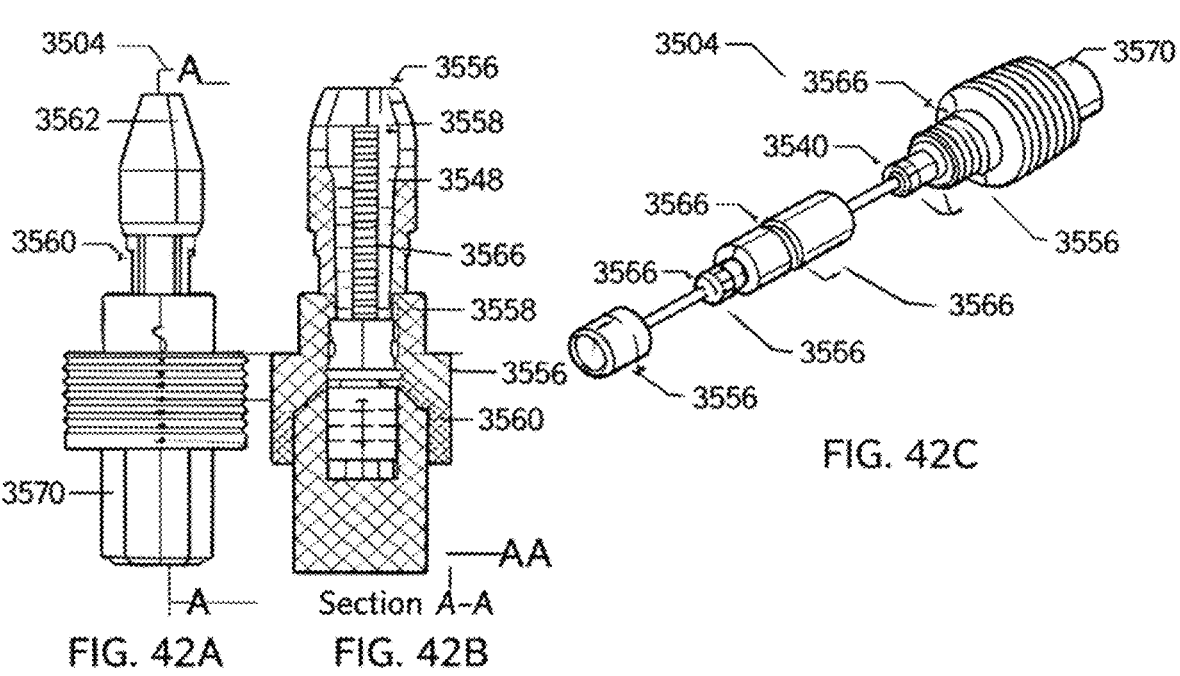
FIG. 42A       FIG. 42B
FIG. 42C

4000

| | |
|---|---|
| CONDUCT ELECTROFORMING | 4002 |
| COAT THE ELECTROFORMED EXPANDABLE BODY | 4004 |
| ETCH DETACHMENT AND BONDING SITES | 4006 |
| ANNEAL THE EXPANDABLE BODY | 4008 |
| FOLD AND WRAP THE EXPANDABLE BODY | 4010 |
| ANNEAL THE EXPANDABLE BODY | 4012 |

4102 — OBTAIN COIL REINFORCED CATHETER

4104 — REMOVE OUTER COATING

4106 — UNWRAP ELECTRICAL CONDUCTORS

4108 — WELD ELECTRODE RING TO CATHODE

4110 — COVER EXPOSED ELECTRICAL CONDUCTORS

4112 — MASK BONDING SITES

COAT CATHETER — 4114

ENGAGE CATHETER TO FLUID SOURCE FITTING — 4116

EXTEND ANODE AND CATHODE — 4118

JACKET ELECTRICAL CONDUCTORS — 4120

SOLDER ELECTRICAL CONDUCTORS TO PLUG — 4122

HEAT SHRINK OVER SOLDER — 4124

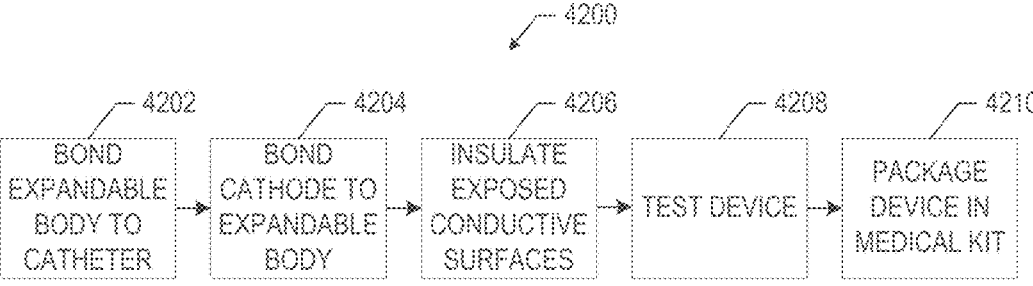

4202 — BOND EXPANDABLE BODY TO CATHETER

4204 — BOND CATHODE TO EXPANDABLE BODY

4206 — INSULATE EXPOSED CONDUCTIVE SURFACES

4208 — TEST DEVICE

4210 — PACKAGE DEVICE IN MEDICAL KIT

FIG. 47

EXPANDABLE BODY DEVICE AND METHOD OF USE

CROSS REFERENCE TO RELATED APPLICATIONS

The present application claims priority to and is a divisional of U.S. patent application Ser. No. 14/372,967, entitled "EXPANDABLE BODY DEVICE AND METHOD OF USE," which is a U.S. National Patent Application of PCT Application No. PCT/US2012/047072 filed Jul. 17, 2012, which claims the benefit of and is a Continuation-in-Part of PCT Application No. PCT/US2012/021620 filed Jan. 17, 2012, PCT Application No. PCT/US2012/021621 filed Jan. 17, 2012, and PCT Application No. PCT/US2012/00030 filed Jan. 17, 2012, each of which claims the benefit of U.S. Provisional Application No. 61/433,305 filed Jan. 17, 2011, the disclosures of each being incorporated herein by reference in their entireties for all purposes.

FIELD OF THE PRESENT DISCLOSURE

The present disclosure relates to devices and systems including an expandable body and a delivery catheter for the treatment of saccular aneurysms of the vascular system or the occlusion of blood vessel segments, where the expandable body ultimately remains in the aneurysm or blood vessel segment in an expanded state. Further, the present disclosure relates to components for, and methods of, attaching the expandable body to the delivery catheter, as well as components for, and methods of, separating the expanded body from the delivery catheter, such that the expanded body remains in place in an expanded state while the delivery catheter is removed from the patient's body.

BACKGROUND OF THE PRESENT DISCLOSURE

An aneurysm is an abnormal outward bulging of a blood vessel that can occur anywhere in the body. This bulge weakens the blood vessel wall, making it susceptible to rupture, which results in bleeding or hemorrhage. Aneurysms are common in the arterial circulation of the brain, where they are known as cerebral aneurysms. When cerebral aneurysms rupture, this often leads to a hemorrhagic stroke, and sometimes brain damage and death. Cerebral aneurysms are a common condition, affecting an estimated 2% of the adult population. Approximately 90% of cerebral aneurysms are saccular with a rounded, pouch-like shape. Invasive surgery remains a mainstay in their treatment, with the surgery involving opening the skull and sealing the aneurysms by placing a small surgical clip on the outside of the neck, thereby limiting blood flow into the aneurysm sac.

Alternatively, minimally invasive, catheter-based, endovascular treatments have been developed wherein a series of small metal coils are used to fill the aneurysm sac, effectively stabilizing it. In order to treat a blood vessel or aneurysm with coils, a physician inserts a catheter into a lumen of the vascular system and maneuvers the catheter tip into the aneurysm sac. With the catheter tip in position, the physician passes small coils through the catheter into the lumen of the vessel or the cavity of the aneurysm. Although effective, coiling of saccular cerebral aneurysms has drawbacks. First, coil placement is difficult to control, often resulting in coil protrusion into the parent vessel or coil migration to non-target locations. Second, coils only partially fill the aneurysm sac. The accumulation of thrombus and scar tissue is required to seal the aneurysm, a process that takes weeks to occur and is sometimes incomplete, often resulting in aneurysm recanalization or rupture, and reducing the effectiveness of coils in the treatment of acute aneurysm rupture with subarachnoid hemorrhage. Incomplete filling of saccular aneurysms with coils is especially common in the neck region of saccular aneurysms, where coil density can be low and blood flow rates high. Third, numerous coils are usually required to treat the aneurysm, resulting in high costs and long treatment times. Fourth, coils are susceptible to compaction, further exposing the aneurysm neck and leading to substantial rates of aneurysm recurrence.

More recently, traditional tubular stents have been adapted for the treatment of cerebral aneurysms. These stents are placed on delivery devices and positioned in the parent vessel adjacent to the aneurysm. These stents are then expanded in the parent vessel with the delivery device, followed by removal of the delivery device. The expanded metal stent acts to seal the neck of the aneurysm and keep blood flow out of the aneurysm sac in order to promote aneurysm thrombosis. Although effective, the use of these "flow diverting" stents has drawbacks. First, the stents may cover and divert blood flow away from important arterial branches adjacent to the aneurysm, sometimes resulting in ischemia and stroke. Second, the stents are a source of thrombus and intimal hyperplasia formation in the parent vessel, which can result in narrowing in the parent vessel lumen, ischemia, and stroke.

In other clinical situations, patients can benefit from the occlusion of certain artery or vein segments through endovascular means. Clinical settings where endovascular vessel occlusion is beneficial include reducing bleeding from an injured vessel, reducing blood flow to tumors, and rerouting the path of blood in the vascular system for other purposes. Alternatively, minimally invasive, catheter-based, endovascular treatments have been developed to occlude blood vessel segments. Endovascular medical devices for blood vessel occlusion include balloon catheters wherein the balloon can be inflated to fill the lumen of a blood vessel segment and detached from the catheter. There are two major drawbacks to the use of detachable balloon catheters for blood vessel occlusion. First, the balloons are made of polymers that generally resist tissue incorporation. This limits fixation of the devices where they are placed. Second, the balloons are configured with elastic walls which are expanded with pressurization and valves designed to maintain that pressure after detachment. Unfortunately, there is a substantial rate of balloon and valve failure, resulting in deflation. Without tissue incorporation, balloon deflation can lead to balloon migration and occlusion of non-target vessel segments.

Endovascular medical devices for blood vessel occlusion include metal coils that are used to fill a portion of the lumen of a blood vessel segment to induce thrombosis and occlusion of the blood vessel segment. There are several major drawbacks to the use of metal coils for blood vessel occlusion. First, numerous coils are usually required to occlude the blood vessel segment, resulting in higher costs and longer treatment times. Second, coil placement is difficult to control, often resulting in coil placement in non-target vessel segments. Third, coils only partially fill the blood vessel. The accumulation of thrombus and scar tissue is required to occlude the blood vessel, a process that takes weeks to occur and is sometimes incomplete, often resulting in incomplete occlusion or recanalization and a failed treatment.

More recently, endovascular medical devices for blood vessel occlusion have been developed that include basket structures that are used to fill a portion of the lumen of a blood vessel segment to induce thrombosis and occlusion of the blood vessel segment. Although only a single basket structure is usually required to occlude a blood vessel segment, and the devices are generally easier to control, these devices only partially fill the blood vessel and require the accumulation of thrombus and scar tissue to occlude the blood vessel. As with coils, this process takes weeks to occur and is sometimes incomplete, often resulting in incomplete occlusion or recanalization and a failed treatment.

Therefore, there remains a need for medical devices, systems, and methods for treating saccular aneurysms, including cerebral aneurysms, which result in a more effective and complete sealing of saccular aneurysms that is more durable and permanent. It is further desired to have medical devices, systems, and methods that seal aneurysm sacs more quickly. Finally, it is desired to have medical devices, systems, and methods that can be performed more easily and in less time, with a lower risk of complications, and at a lower cost, when compared with existing treatments.

There also remains a need for catheter-based medical devices, systems, and methods for the occlusion of blood vessel segments that are simple to perform, result in a rapid, controlled, and complete occlusion, have a low risk of recanalization, device migration, or other complications, and can be purchased at a reasonable cost.

SUMMARY OF THE PRESENT DISCLOSURE

Disclosed herein are medical systems and devices for the treatment of saccular aneurysms using an expandable body or structure. Also disclosed are medical systems and devices for the occlusion or blockage of blood vessel segments, including arteries, veins, and other vascular conduits of the vascular system using an expandable body or structure. The expandable body may be configured for use as a balloon, a ballstent, or a blockstent. The terms expandable body, expandable structure, expandable balloon, ballstent, and blockstent, as used herein, refer to an expandable body having a single-layered or multi-layered construction and wherein the expandable body may be first introduced in a non-expanded state into a patient using a delivery device, second, negotiated in the non-expanded state through the cardiovascular system of the patient to a target treatment site (i.e., implantation site), third, expanded at the target treatment site into an expanded state, and, fourth, detached from the delivery device to remain in the patient's body in an expanded configuration at the target treatment site. Also disclosed herein are methods of manufacturing and using the medical systems and medical devices.

A medical system disclosed herein may be for filling a biological space of a patient. Such a medical system includes a single lobed metallic expandable body (e.g., a ballstent or blockstent) and delivery device. Filling of a biological space includes filling at least a portion of a lumen of a ruptured or non-ruptured aneurysm or a lumen of a blood vessel segment, including arteries and veins.

The single lobed metallic expandable body includes a distal region, a proximal region generally opposite the distal region, and an intermediate region transitioning from the distal region to the proximal region. A center axis extends proximal-distal between the proximal region and distal region of the single lobed metallic expandable body. A wall of the single lobed metallic expandable body extends generally continuously through the intermediate region from the distal region to the proximal region to define an exterior surface of the expandable body and an interior surface of the expandable body. The interior surface defines an interior volume of the expandable body, wherein the expandable body is configured to expand from a deliverable (i.e., collapsed or non-expanded) configuration to an expanded configuration.

The delivery device has a longitudinally extending body that includes a proximal end and a distal end generally opposite the proximal end. The distal end of the delivery device is operably coupled to the proximal region of the expandable body. In one embodiment, when the expandable body is in the deliverable configuration, the wall assumes a pleated configuration having a plurality of pleats folded over in a clockwise direction relative to the center axis, or, alternately, in a counter-clockwise direction relative to the center axis to form a folded-over region of the expandable body. Conversely, when the expandable body is in the expanded configuration, the plurality of pleats is not folded over and the pleated configuration substantially ceases to exist.

In one embodiment, the medical system includes an electrolysis system having an electrical circuit partially supported on the delivery device and configured to decouple a proximal region of the expandable body from a distal end of the delivery device by electrolysis. In other embodiments, the medical system includes an electrical system having an electrical circuit partially supported on the delivery device to supply electrical energy to a polymer link coupled to the proximal region of the expandable body and the delivery device. The supplied electrical energy heats the link thereby causing the link to release. The electrical system can also heat the polymer coupling by passing an electric current through a resistive heating element or wire adjacent to the polymer coupling.

Methods for filling a biological space of a patient are also disclosed herein. One method includes providing a single-lobed metallic expandable body configured to expand from a deliverable configuration to an expanded configuration. The expandable body is delivered into the biological space of the patient in a deliverable configuration via a delivery device having a distal end operably coupled to a proximal region of the expandable body. A fluid medium can be delivered into the interior volume of the expandable body via the delivery device to cause the expandable body to assume the expanded configuration. After expansion, the expandable body is decoupled from the delivery device.

In one embodiment, the method includes using an electrolysis system having an electrical circuit partially supported on the delivery device to decouple a proximal region of the expandable body from a distal end of the delivery device by electrolysis. In other embodiment, the method includes using an electrical system having an electrical circuit partially supported on delivery device to supply electrical energy to a polymer link coupled to the proximal region of the expandable body and the delivery device. The supplied electrical energy heats the link thereby causing the link to release. The electrical system may also be configured to heat the polymer coupling by passing an electric current through a resistive heating element or wire adjacent to the polymer coupling.

Methods for manufacturing a system for filling a biological space of a patient are also disclosed herein. One method includes manufacturing a single lobed metallic expandable body having a distal region, a proximal region generally opposite the distal region, and an intermediate region transitioning from the distal region to the proximal region. A center axis extends proximal-distal between the proximal region and distal region of the single lobed metallic expandable body. A wall of the single lobed metallic expandable body extends generally continuously through the intermediate region from the distal region to the proximal region to define an exterior surface of the expandable body and an interior surface of the expandable body. The interior surface defines an interior volume of the expandable body.

The methods also include manufacturing a delivery device having a longitudinally extending body that includes a proximal end and a distal end generally opposite the proximal end, operably coupling the distal end of the delivery device to the proximal region of the expandable body. The methods of manufacturing also include forming the wall of the expandable body into a pleated configuration. The pleated configuration includes a plurality of pleats folded over in a clockwise direction relative to the center axis, or alternately, a counter-clockwise direction relative to the center axis to form a folded-over region of the expandable body.

Another method of manufacturing a system for filling a biological space of a patient includes coupling a stainless steel ring to a proximal end of a sacrificial mandrel, depositing a metal layer over the sacrificial mandrel and at least over a portion of the stainless steel ring, and eliminating the sacrificial mandrel to leave behind the metal layer in the form of a hollow body having the shape of the sacrificial mandrel. The stainless steel ring is therefore joined to and extending from a proximal region of the hollow body.

The method can include applying an electrical insulation material to an exterior surface and an interior surface of the hollow body and an exterior surface of the stainless steel ring and creating an anode by rendering a portion of the exterior surface of the region of the neck composed of the stainless steel ring free of the electrical insulation material. The method further includes coupling the stainless steel ring to a distal end of a delivery device and electrically coupling an electrolysis system to the potential anode through a conduction path that travels through the delivery device.

In the various embodiments of the systems and methods described above, the walls of the expandable body can include at least one metal layer having a thickness ranging between approximately 5 μm and 50 μm. In one example, the metal layer of the distal, intermediate, and proximal regions may include gold or platinum. The wall of the expandable body may also include an inner layer of a non-metallic coating extending over an inner surface of the metal layer and an outer layer of a non-metallic coating extending over an outer surface of the metal layer. The non-metallic coatings may be an electrical insulation material, including, for example, Parylene. For example, an inner layer and outer layer of Parylene may coat the gold or platinum metal layer.

A surface of the metal layer may include rounded, pebbled, or granular surface structures that have a surface height of approximately 0.1 μm to approximately 10 μm. The outer surface of the metal layer may include generally tubular protrusions. In one embodiment, some of the generally tubular protrusions are branched. In another embodiment, some are joined on both ends to the metal layer to form loops.

The metal layer of the expandable body may be produced by electroforming on a mandrel, wherein optionally all or a portion of the mandrel is sacrificial. Portions of the mandrel may be formed of sacrificial aluminum components, as well as non-sacrificial steel or stainless steel components. The mandrel may have a lapped finish with no more than approximately 0.1 micron between peak and valley of rough surface features. Alternately, the mandrel may have a pleated outer surface that generally replicates a pleated configuration of the expandable body that is intermediate in shape between the deliverable configuration and the expanded configuration. A non-sacrificial stainless steel mandrel component may include a surface layer of gold or platinum that extends over at least a portion of one of an inner surface or an outer surface of the stainless steel surface layer of the non-sacrificial mandrel component.

In various embodiments, the expandable body may undergo one or more annealing processes. The expandable body may be annealed before and after being folded into the deliverable configuration. Further, the expandable body may undergo an annealing process while comprising a non-metallic coating.

The wall of the expandable body may include pores that may extend completely through the thickness of the wall from the interior to the exterior surface. The pores range from 1 micron to 500 microns in diameter. As such, the expandable body may be inflated by a fluid supply device in fluid communication with the interior volume of the expandable body via the delivery device. The fluid supply device is configured to provide a supply fluid flow rate to the interior volume that exceeds an escape fluid flow rate from a plurality of pores at a fluid delivery pressure.

When in the delivery configuration, the folded-over region of the expandable body may define a wire-receiving channel. In one embodiment, however, no portion of the delivery device is found within the folded-over region of the expandable body. Each pleat includes a ridge line extending proximal-distal and radially away from the center axis and each pleat is separated from any immediately adjacent pleat by an interposed trough extending proximal-distal, such that the pleated configuration has an alternating ridge-trough arrangement. When folded each pleat is folded over an immediately adjacent pleat in a clockwise direction relative to the center axis, or in a counter-clockwise direction relative to the center axis. In one embodiment, no portion of the delivery device is found within the folded-over region of the expandable body. In another embodiment, the folded-over region of the expandable body may define a channel for receiving a guidewire.

In various embodiments, the expandable body is inflatable to achieve the expanded configuration. The expandable body is inflated via the delivery of a fluid medium to the interior volume of the expandable body. The fluid medium typically includes a liquid or gas. During expansion, pressure within various embodiments of the expandable body is three atmospheres. Other suitable pressures include two atmospheres and one atmosphere or less.

During inflation, the pleated configuration and the plurality of pleats of the expandable body that are present in the deliverable configuration are substantially eliminated. When expanded, the expandable body possesses sufficient strength to maintain itself in the expanded configuration within a biological space after separation from the delivery device.

The metallic expandable body and the delivery device are configured to allow the interior volume of the expandable body to, optionally, be at least partially filled with a solid or semi-solid support structure. The support structures include metallic or polymeric coils or wires, metallic or polymeric expansile structures, beads, balls, microspheres, a bioresorbable material, or combinations thereof. In one embodiment, solid or semi-solid material or members not derived from the patient are not required in the interior volume of the expandable body to cause the expandable body to assume or maintain the expanded configuration after separation of the expandable body and the delivery device.

When the expandable body is in the expanded configuration, the expandable body has an overall shape that is a sphere or an oblong shape. In one particular embodiment where the expandable body is to serve as a ballstent, the intermediate region, the proximal region, and the distal region combine to form a generally spherical shape. In another particular embodiment where the expandable body is to serve as a blockstent, the intermediate region is generally cylindrical and the proximal region and the distal region are both generally hemispherical.

The expandable body may include a neck extending proximally away from the proximal region to operably couple to the distal end of a delivery device. In one embodiment, both the expandable body and the neck are formed entirely from a malleable metal such as gold or platinum. In another embodiment, at least a portion of the neck includes stainless steel while the remainder of the expandable body includes a malleable metal such as gold or platinum. The delivery device may be operably coupled the neck portion of the proximal region of the expandable body by an elastic sleeve. The elastic sleeve may be formed of ChronoPrene, silicone, or PEBAX®. A PEBAX® sleeve may have a durometer ranging between 25 and 80 Shore D. The delivery device may be engaged to the expandable body by a friction fit. Additionally, a vacuum may be present in the catheter. The expanded expandable body and the delivery device may be separated by pulling apart the delivery device and the expandable body. The delivery device includes a longitudinally extending body, which may have a hydrophilic or lubricious coating. This coating may also be present on the expandable body. The distal segment of the longitudinally extending body is operably coupled to a proximal region of the expandable body. For example, the distal end of the longitudinally extending body may be received in the neck at the proximal region of the expandable body, such that the outer surface of the distal segment of the longitudinally extending body is in contact with an inner surface of the neck of the expandable body. In another example, the distal segment of the longitudinally extending body terminates near a proximal edge of a ring-shaped region of exposed metal in the neck of the expandable body.

The various systems and methods may include or use an electrolysis system configured to deliver constant current, a constant voltage, or a square wave voltage to the exposed metal surface on the neck to detach the expandable body. The separation occurs in an annular, ring-shaped non-coated or exposed metal surface region of the neck formed of stainless steel or gold and exposed by, for example, laser etching. During electrolysis, the ring-shaped non-coated or exposed metal surface region of the neck acts as an anode. When delivering a square wave voltage, the voltage of the anode is modulated based on a comparison between the voltage of the anode and the voltage of a reference electrode supported on the delivery device or residing external to the delivery device, such as with a needle or electrode pad residing on or in the patient.

One method of manufacturing the expandable body includes: a) providing a sacrificial mandrel comprising a pleated outer surface; b) depositing a metal layer over the sacrificial mandrel; c) removing the sacrificial mandrel and leaving behind the metal layer in the form of a hollow pleated body; d) coating with a non-metallic material an interior surface and an exterior surface of metal layer of the hollow pleated body; and e) folding the hollow pleated body to further increase the extent to which the hollow pleated body is pleated, the folding comprising folding over a plurality of pleats in a clockwise direction relative to a center axis of the hollow pleated body, or a counter-clockwise direction relative to the center axis.

The portion of the electrolysis system supported on the delivery device includes one or more conductors embedded in the wall of the catheter that act as both electrical conductors for the electrical system and structural reinforcement for the catheter wall. The conductors are wires, cables, or other electrical conductors that may be routed through the catheter wall in a spiral, braided, or straight configuration. One of the conductors is in electrical communication with a portion of the expandable body that can function as an anode, such as at or near a ring-shaped region of the neck having an exposed metal surface, while another of the conductors is in electrical communication with a structure supported on the delivery device that can function as a cathode, such as a platinum metal ring. In one embodiment, one of the conductors is in electrical communication with a structure supported on the delivery device that can function as a reference electrode.

DESCRIPTION OF FIGURES

FIGS. 1A-H are side and end views of embodiments of the expandable body of the medical device.

FIGS. 4A-E are views of an embodiment of the medical device illustrating a sequence of steps associated with the delivery of the expandable body to an aneurysm and deployment.

FIGS. 4F-J are views of an embodiment of the medical device located in a vessel lumen and illustrating a sequence of a sequence of steps associated with blocking or occluding the lumen of a vessel segment.

FIGS. 5A-H are side and end views of embodiments of the expandable body of the medical device.

FIGS. 8A-E are views of an embodiment of the medical device illustrating a sequence of steps associated with the delivery of the expandable body to an aneurysm and deployment.

FIGS. 8F-J are views of an embodiment of the medical device located in a vessel lumen and illustrating a sequence of a sequence of steps associated with blocking or occluding the lumen of a vessel segment.

FIGS. 11A-B are plan views of embodiments of the ballstent and blockstent, respectively, wherein the shape of the expanded body is being changed by applying an external force using a balloon catheter.

FIGS. 12F-I are plan views of embodiments of the ballstent and blockstent with external surface projections for anchoring the expanded body to the surrounding tissues.

FIG. 13 is a plan view of an embodiment of the ballstent having an elastomer joint.

FIG. 14A is a perspective view of an embodiment of an expandable body as compressed against a delivery catheter.

FIG. 14B is a perspective view of an embodiment of a compressed expandable body.

FIG. 14C is a perspective view of an embodiment of a compressed expandable body that defines an off-center channel.

FIG. 14D is a perspective view of an embodiment of a compressed expandable body.

Figures 15A, 15B, 15C, 15D:
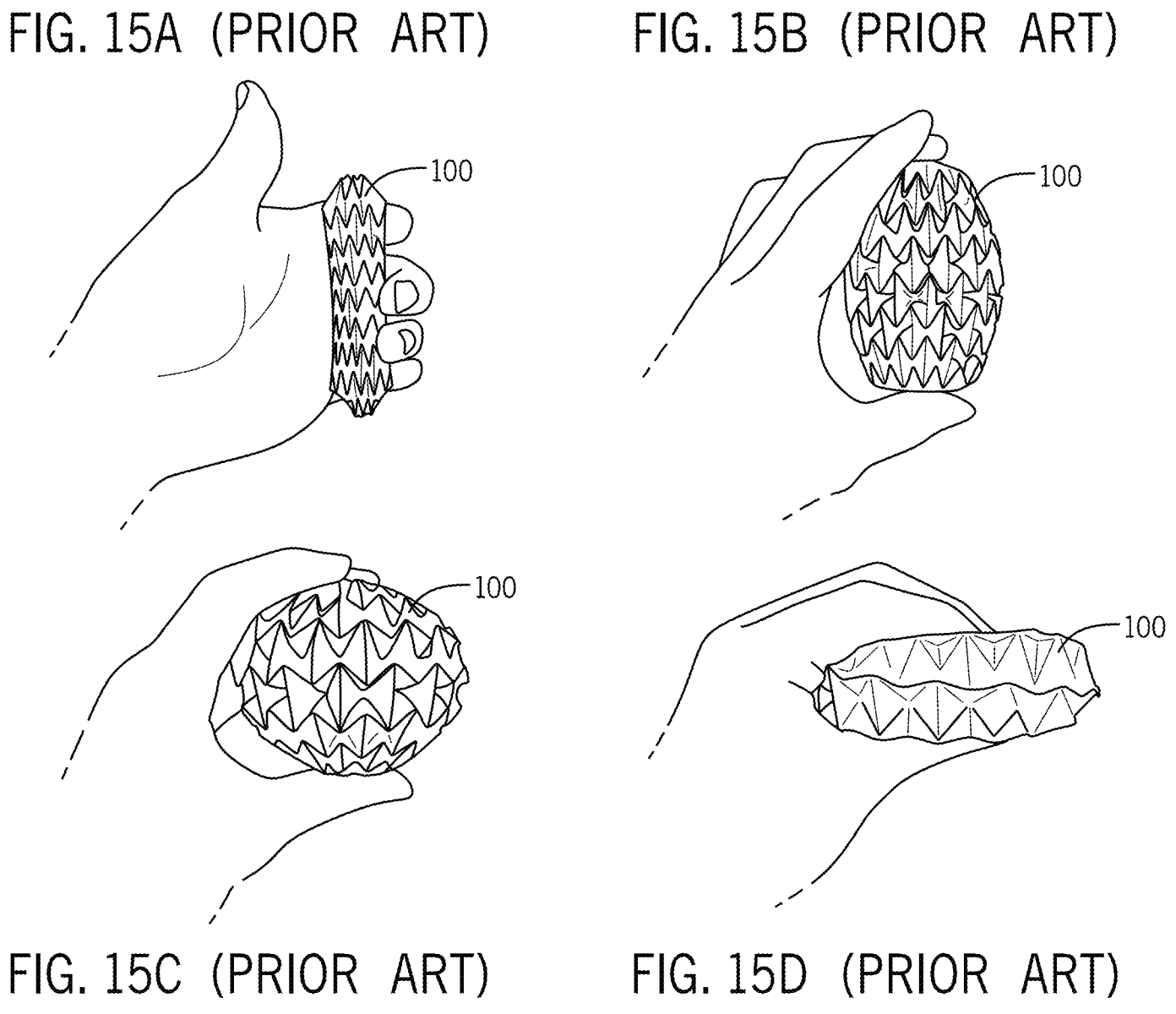

FIGS. 15A-D are photographs depicting an exemplary manner of folding and compressing an expandable body.

FIGS. 23A-B are perspective views of partial cross-sections of an embodiment of the medical device wherein the expandable body is attached to the delivery catheter, wherein FIG. 23A depicts a compressed expandable body and FIG. 23B depicts an expanded expandable body.

FIG. 30A is a table providing exemplary dimensions for embodiments of the expandable body when in spherical form. The dimensions are provided for example and not limitation.

FIG. 30B is a table providing exemplary dimensions for embodiments of the delivery catheter, the guide wire, and the expandable body when in the form of a blockstent having a cylindrical intermediate portion and hemispherical ends. The dimensions are provided for example and not limitation.

FIG. 31A illustrates various dimensions for an expandable body having a cylindrical intermediate portion and hemispherical ends.

FIGS. 31B-C illustrate various dimensions for a neck region of an expandable body.

11

Figures 37A, 37B, 37C, 37D:
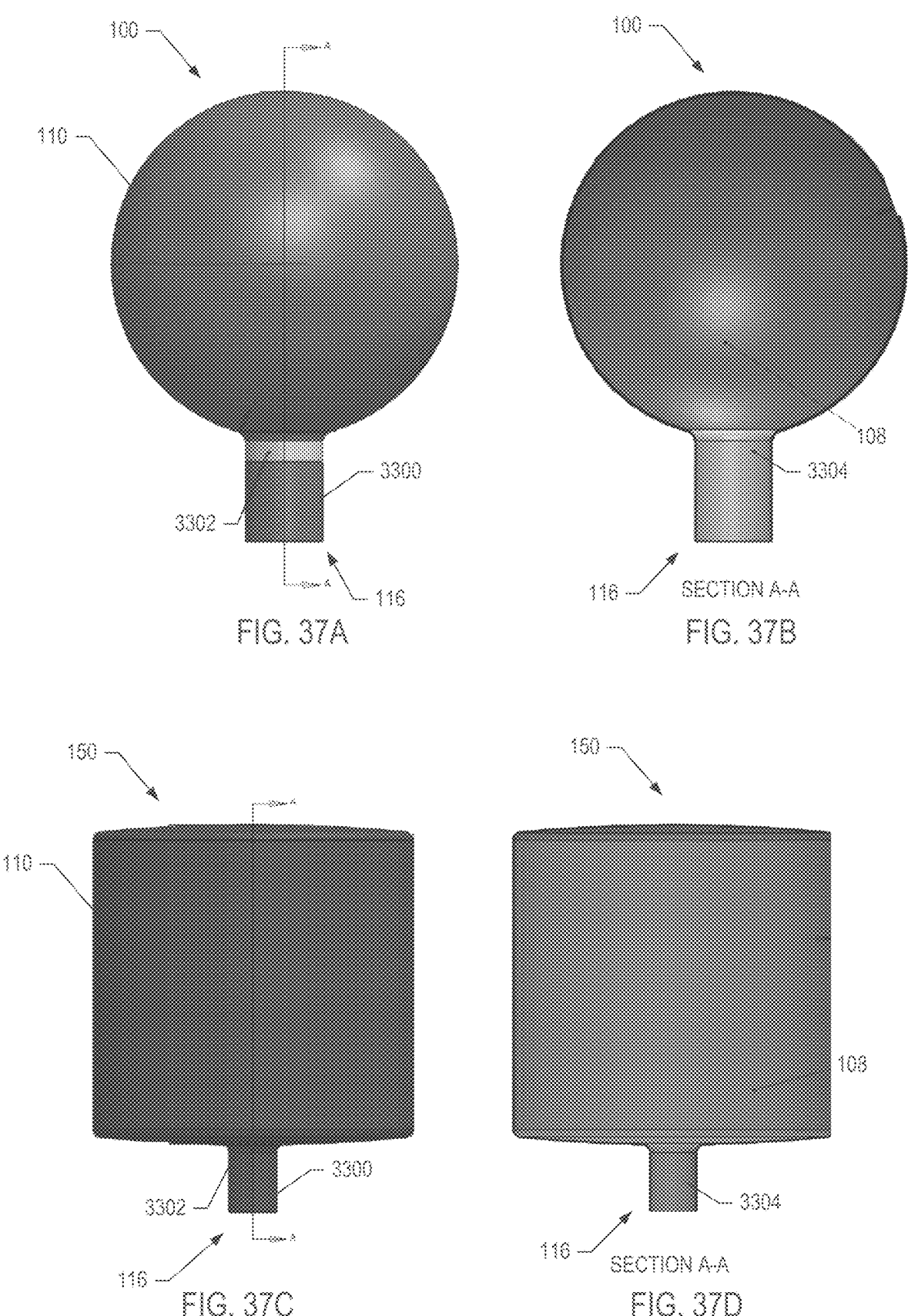

FIGS. 37A-B respectively depict coatings on an exterior surface and an interior surface of a metal expandable body in the spherical form of a ballstent.

FIGS. 37C-D respectively depict coatings on an exterior surface and an interior surface of a metal expandable body in the form of a blockstent.

FIGS. 37E-H are various plan views and cross-sections depicting a region of exposed metal surface wherein the metal expanded body is detached from the delivery catheter by electrolysis.

Figures 38A, 38B:
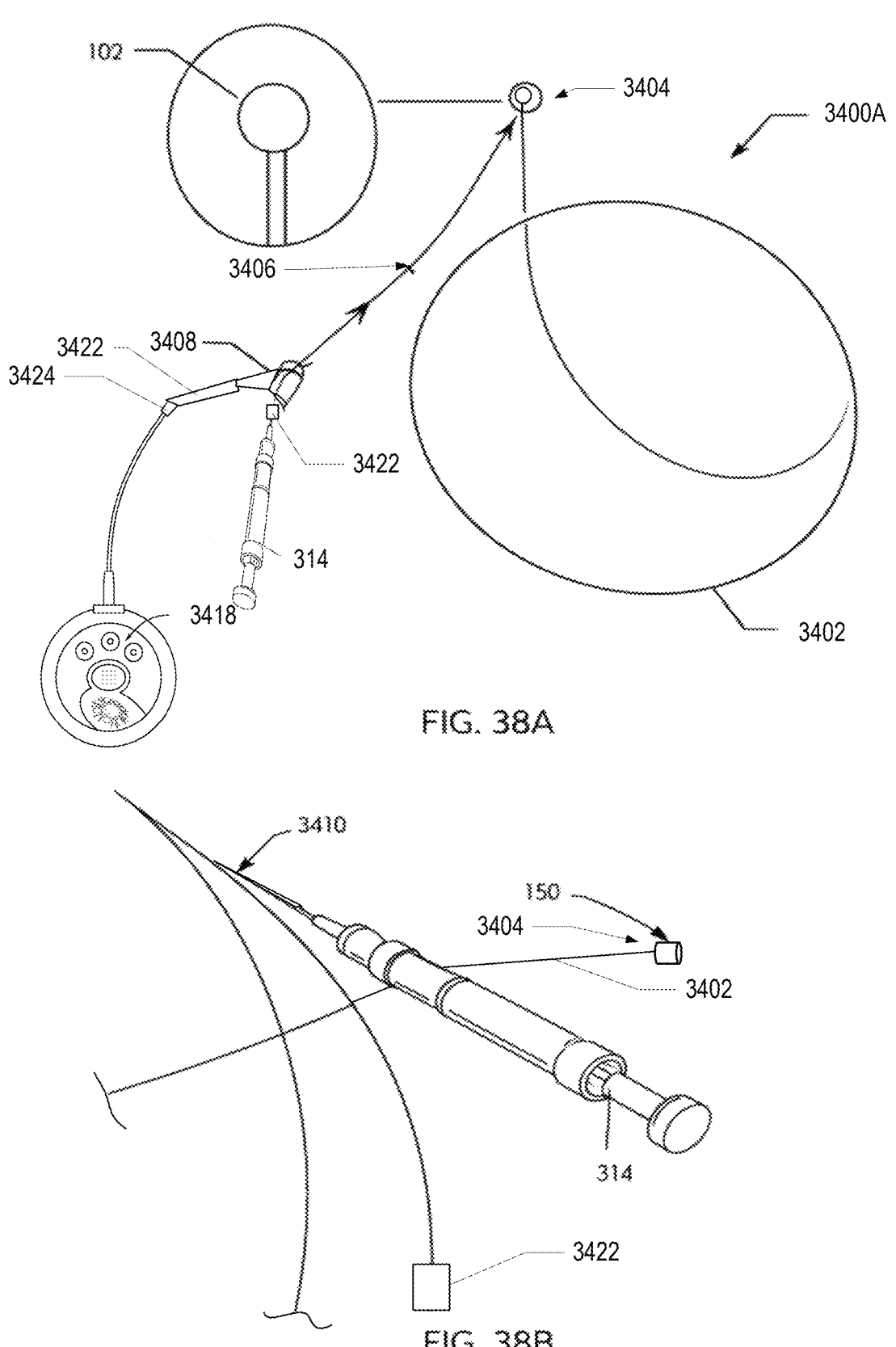

FIGS. 38A-B are plan views of embodiments of the ballstent medical device and the blockstent medical device, respectively.

Figure 39:
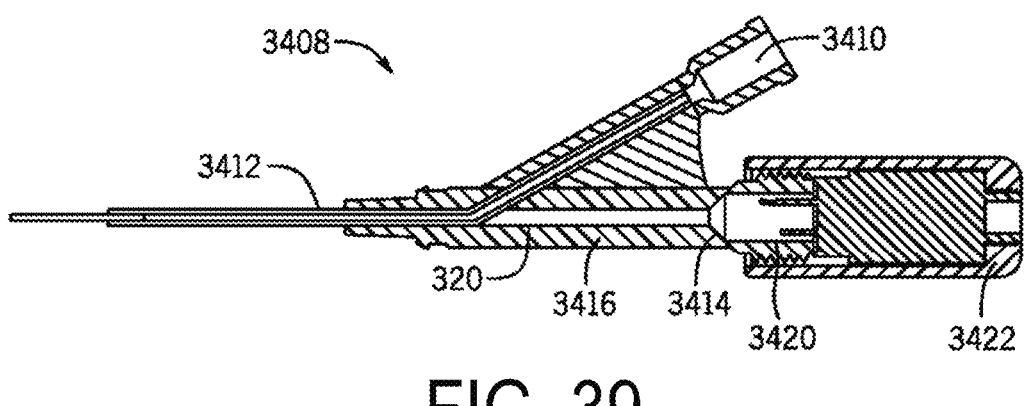

FIG. 39 is a cross-sectional view of a hub for use with a ballstent or blockstent medical device wherein detachment of the expanded body is performed by passing an electrical current into the medical device.

Figure 40:
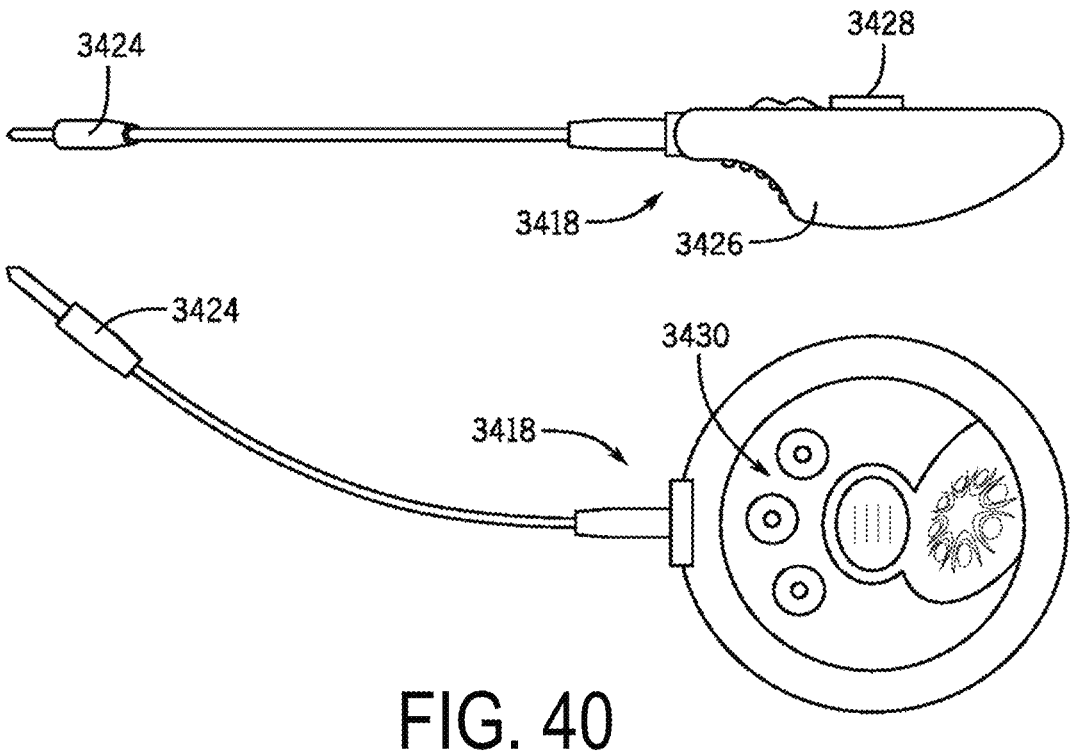

FIG. 40 is a top plan and side plan view of a handheld controller for use with a ballstent or blockstent medical device wherein detachment of the expanded body is performed by passing an electrical current into the medical device.

Figure 41A:
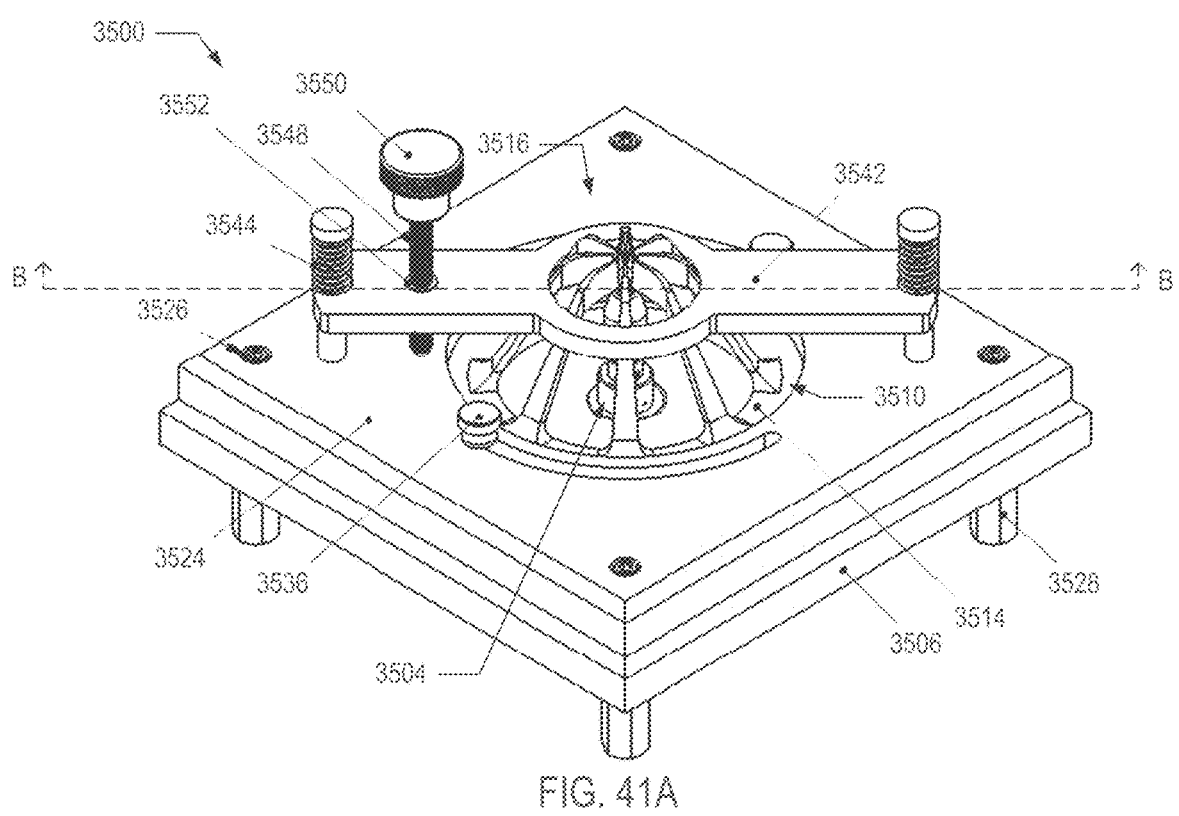
Figure 41B:
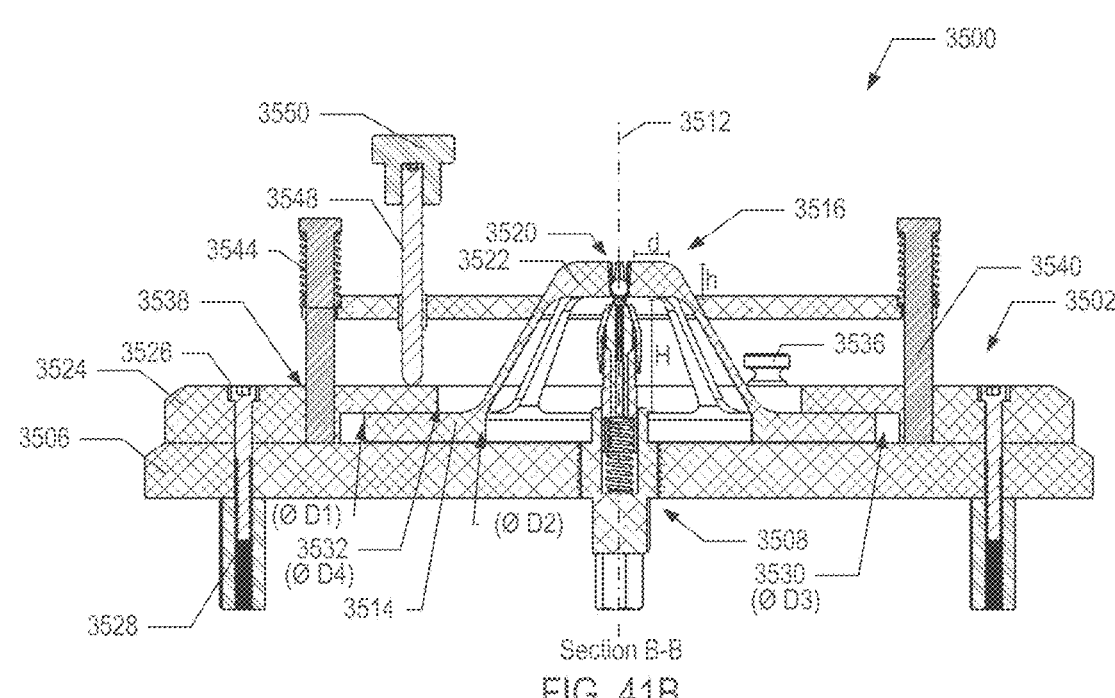

FIGS. 41A-C depict an expandable body folding and wrapping tool.

FIGS. 42A-C depict a collet assembly for use with an expandable body folding and wrapping tool.

Figure 43A:
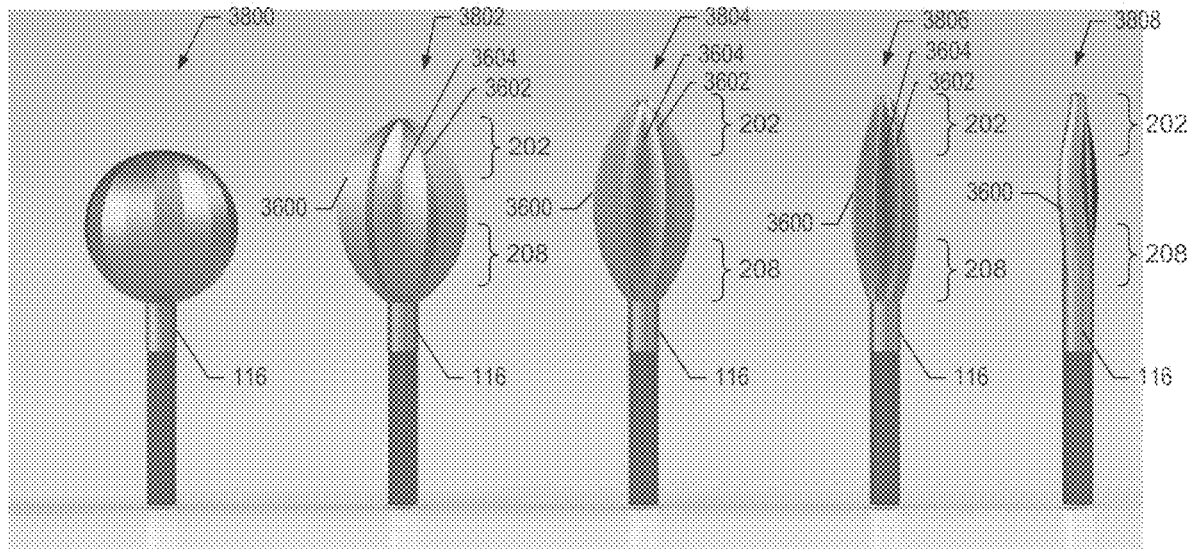
Figure 43B:
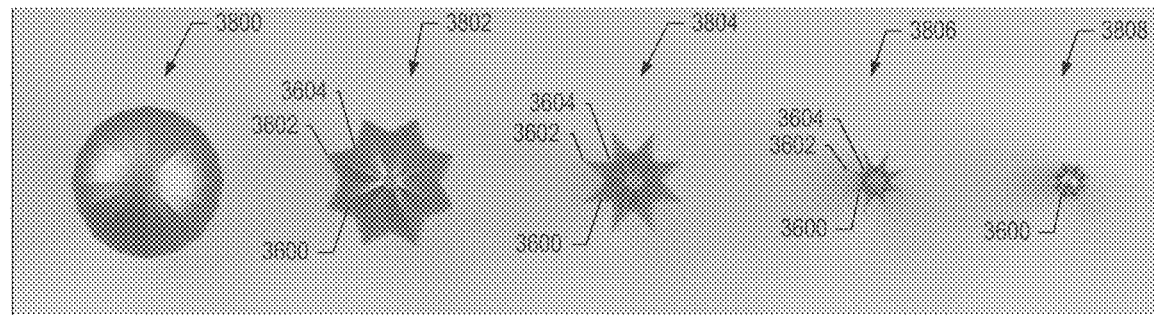

FIGS. 43A-B depict a metal ballstent at various stages of folding and wrapping.

Figure 44A:
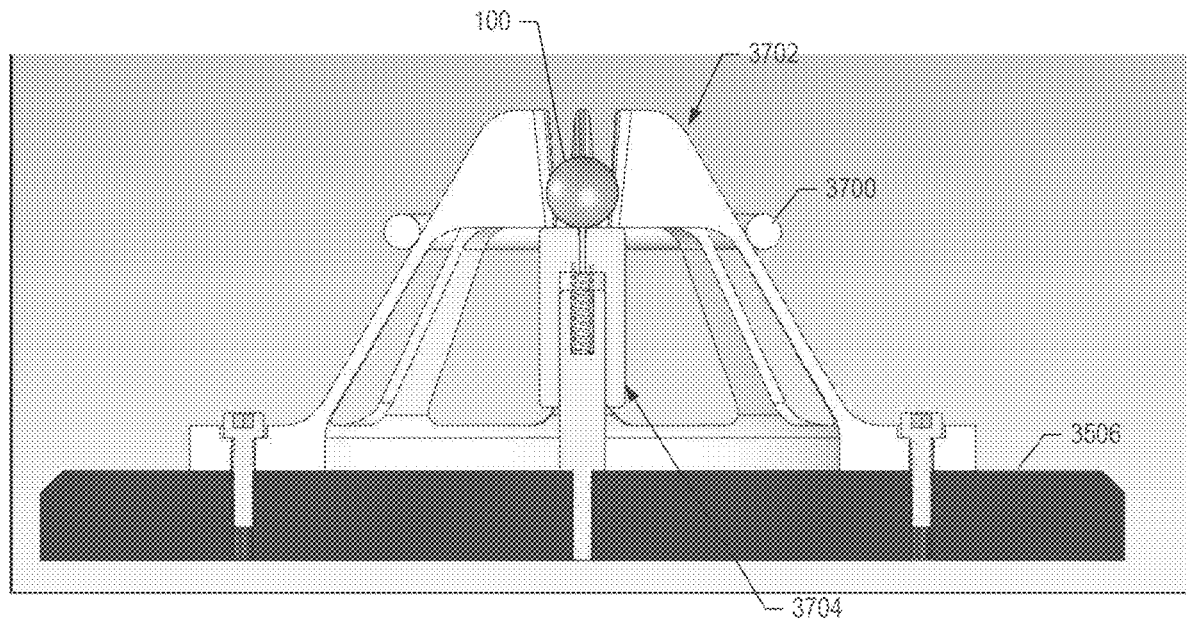
Figure 44B:
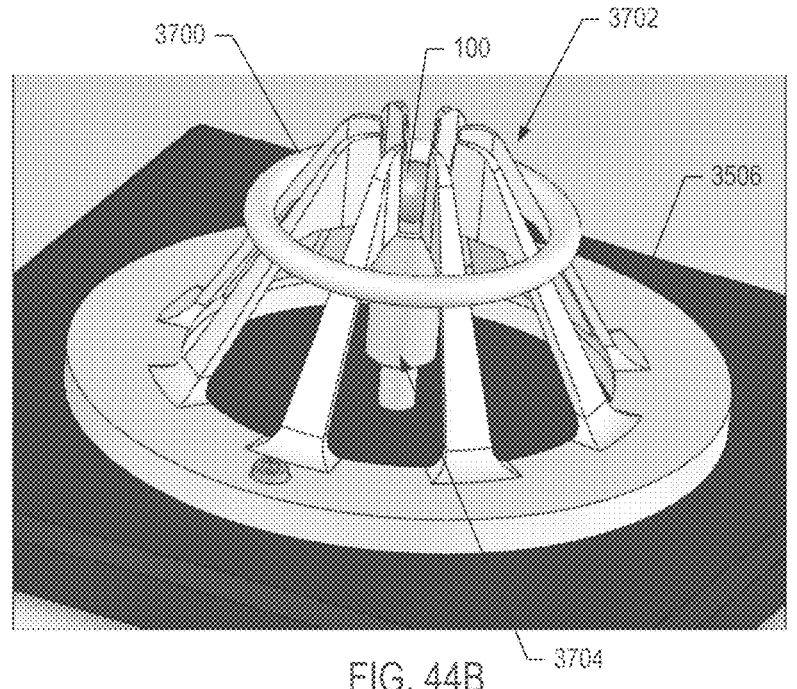

FIGS. 44A-B depict another expandable body folding tool.

Figure 44C:
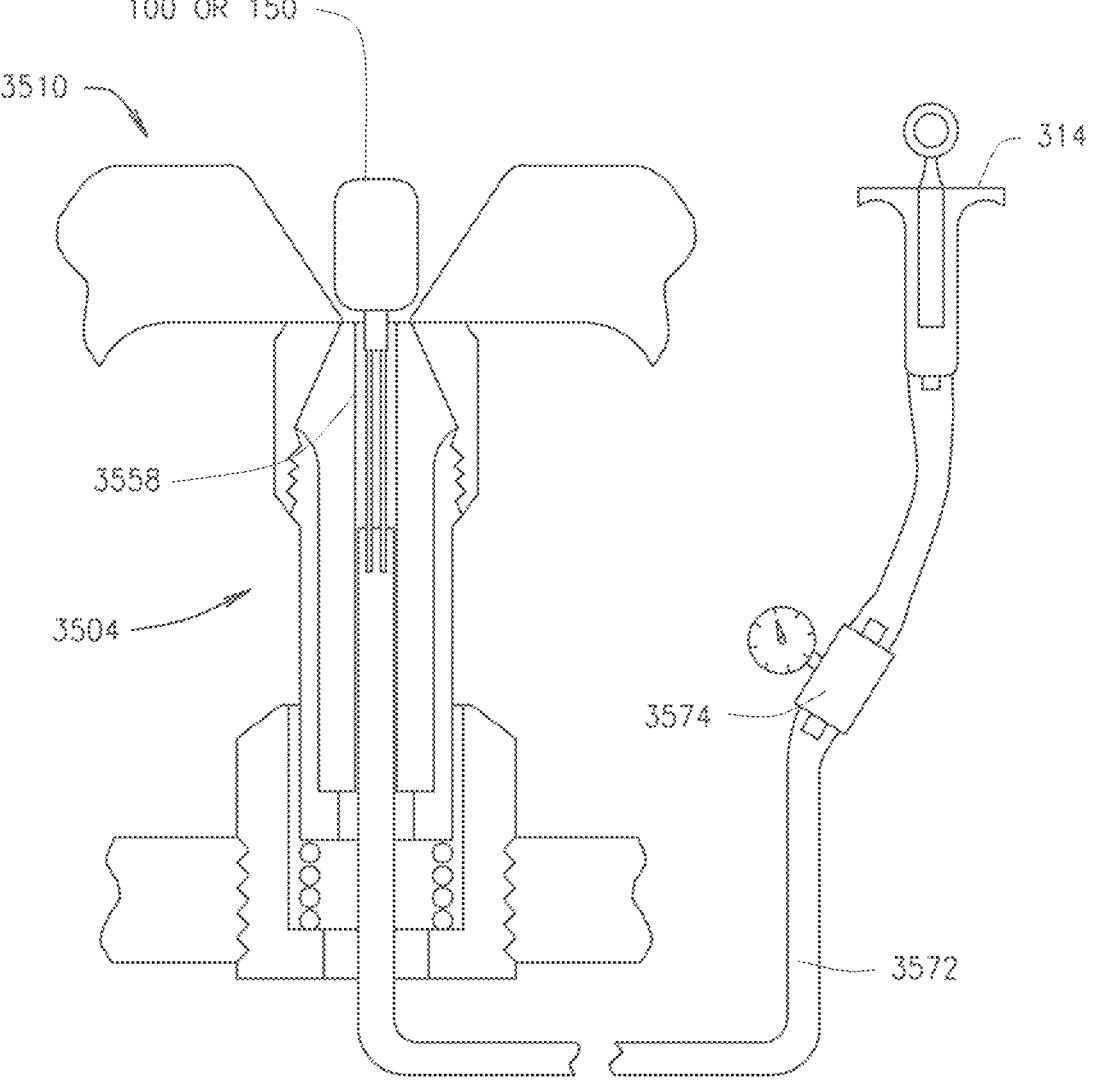

FIG. 44C is a partial cross-sectional view of another expandable body folding tool.

FIGS. 45-47 are flowcharts illustrating the steps for manufacturing the expandable body, a delivery catheter, and a medical kit containing a medical device, respectively.

DETAILED DESCRIPTION

The present disclosure relates to a medical device including a delivery device and an expandable structure or expandable body that may be referred to as a "ballstent" or a "blockstent," depending on the application in which the expandable body is used. The terms expandable body, expandable structure, expandable balloon, ballstent, and blockstent can generally be used interchangeably. Particular embodiments of the expandable body may be referred to a ballstent or a blockstent according to the structure and/or use of the body.

The expandable body is a thin-walled stent-like device that can be expanded into a semi-rigid form that can remain in the body for an extended period. Specifically, the expandable body, when acting as a ballstent, is configured for use in filling and sealing saccular aneurysms of blood vessels, especially saccular cerebral aneurysms and ruptured aneurysms. The expandable body, when acting as a blockstent, is configured for use in blocking or occluding the lumen of segments of arteries, veins, and other biological conduits.

The delivery device is configured to deliver the ballstent to an aneurysm and to provide a pathway, through the lumen of a hollow cylindrical member or lumen, for a fluid medium to move into the void of the ballstent, in order to expand it and fill at least a portion of the volume of the aneurysm sac. Similarly, the delivery catheter can be configured to deliver a blockstent to a blood vessel segment and to provide a pathway, through a cylindrical member or lumen, for fluid to move into the central void of the blockstent, in order to expand it and fill at least a portion of the lumen of the blood vessel segment. Expanding the expandable body, as used herein, can refer to partial or complete expansion of the body using a fluid (i.e., a liquid, gas, gel, or combination thereof) or a solid (i.e., a solid body, a lattice, granular particles, etc., or a combination thereof).

The expandable body can be formed by depositing a metal layer over a mandrel using an electroforming process. During the electroforming process, a metal ring, such as a stainless steel or gold ring, may be incorporated into the metal layer to create a neck for the expandable body. The mandrel may be a sacrificial mandrel that can be eliminated from the expandable body after electroforming, to yield a hollow metallic expandable body.

The hollow metallic expandable body undergoes one or more annealing processes. The interior and exterior surfaces of the metallic expandable body may be coated with a non-metallic material, such as a polymer or an electrically insulating material. The metallic expandable body may be annealed before and after the coated metallic expandable body has been caused to assume a deliverable (i.e., collapsed or non-expanded) folded or pleated configuration.

The metallic expandable body can be folded into a deliverable configuration for introduction into a blood vessel segment or aneurysm. When folded into the deliverable configuration, the metallic expandable body is formed into a pleated configuration, having a number of pleats, which may be wrapped around a central axis of the metallic expandable body.

When used to fill an aneurysm, the delivery device and an attached ballstent are advanced into the lumen of the aneurysm sac. Similarly, when used to occlude a blood vessel or other biological conduit, the delivery device and an attached blockstent are advanced into the lumen of vessel or conduit. The delivery device can also deliver a fluid, a solid, or a combination thereof, to the interior void of the expandable body to expand the body in the lumen of the aneurysm sac or vessel segment, and to help maintain the expansion of the expanded body. The expanded body may be detached from the delivery device by one or more of a variety of arrangements and methods including mechanical, electrical, thermal, chemical, hydraulic, or sonic arrangements and methods.

The medical device can be used as part of various systems, methods, and medical kits. These systems, methods, and medical kits can be used to treat saccular arterial aneurysms, such as a saccular cerebral aneurysm, and to occlude a blood vessel or other biological conduit, such as a ductus arteriosus, bronchus, pancreatic duct, bile duct, ureter, and fallopian tube. Alternatively, these systems, methods, and medical kits can be used to treat a variety of medical conditions.

The Expandable Body

In various embodiments, an expandable body configured for the occlusion of saccular cerebral aneurysms is generally referred to as a ballstent, and can have a spherical, oblong, or cylindrical shape with rounded ends. In various other embodiments, an expandable body configured for the occlusion of the lumen of blood vessel segments is generally referred to as a blockstent, and can take an oblong or cylindrical shape.

A ballstent 100, is shown in FIG. 1A in an expanded state. This embodiment has an external proximal neck 116 that defines an opening 112 for the passage of fluids, liquids, gases, gels, or solids into the void of the ballstent. Another embodiment of the spherical ballstent 100 is shown in FIG. 1B in an expanded state. This embodiment has an internal neck 116 that defines an opening 112, also for the passage of fluids, liquids, gases, gels, or solids into the void of the ballstent. Other embodiments of the expandable body, namely, a blockstent 150 are shown in FIGS. 1C-1F, wherein the blockstent 150 is cylindrical with substantially planar opposed ends and having an external proximal neck 116 (FIG. 1C) or an internal proximal neck 116 (FIG. 1D). FIGS. 1E-1H depict expandable bodies that may be used as ballstents 100 or blockstents 150 with external or internal proximal necks 116.

Figures 5A, 5B:
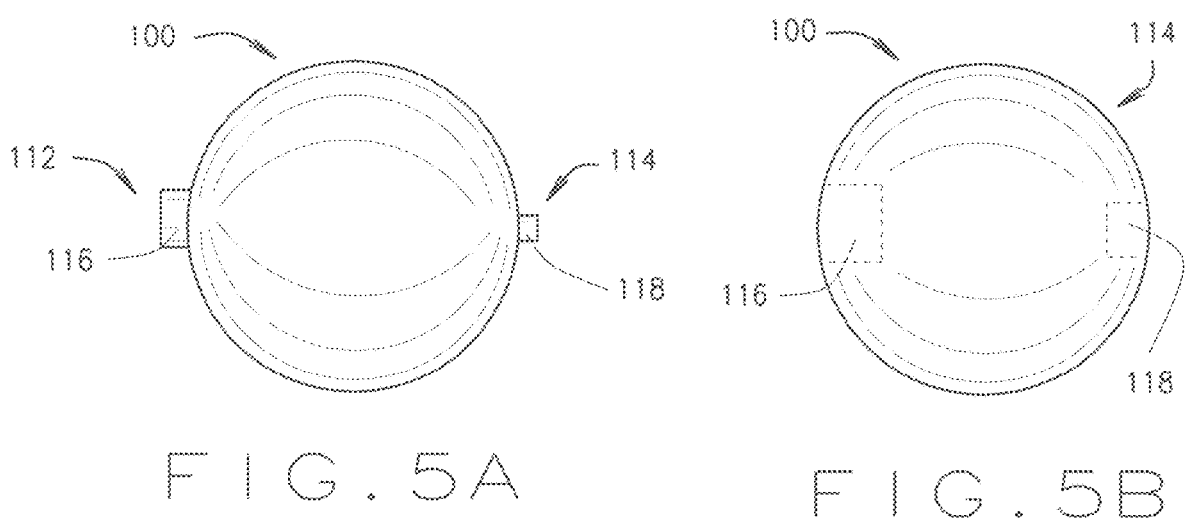
Figure 5C:
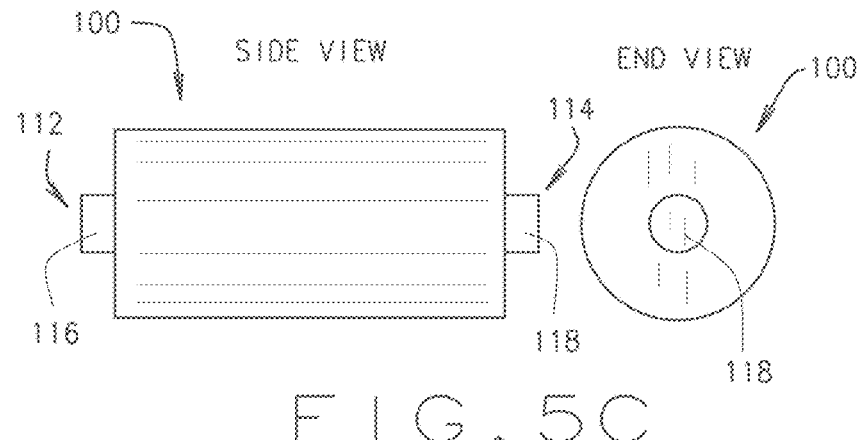
Figure 5D:
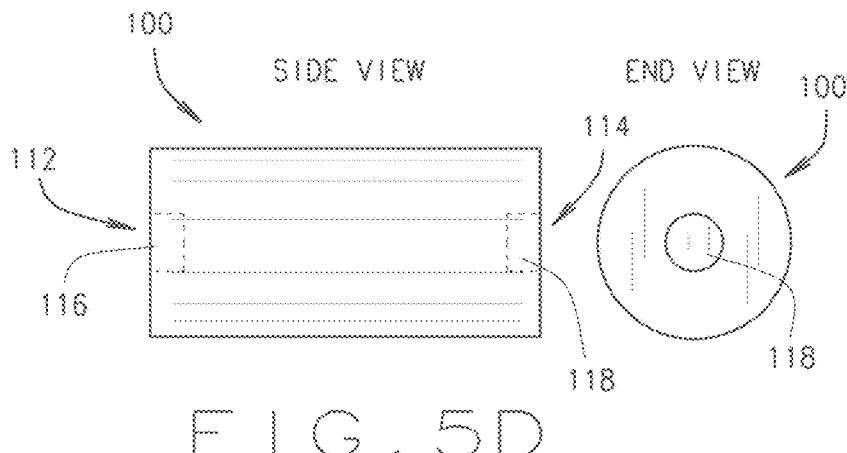

Another spherical embodiment of the ballstent 100 is shown in FIG. 5A in an expanded state. This embodiment has an external proximal neck 116 that defines an opening 112 for the passage of fluids, liquids, gases, gels, or solids into the void of the ballstent. This embodiment also has an external distal neck 118 that defines an opening 114 for the passage of a guide wire 302. Another spherical embodiment of the ballstent 100 is shown in FIG. 5B in an expanded state. This embodiment has an internal proximal neck 116 that defines an opening 112, also for the passage of fluids, liquids, gases, gels, or solids into the void of the ballstent. Further, this embodiment has an internal distal neck 118 that defines an opening 114 for the passage of a guide wire 302. In other embodiments, the ballstent can be constructed without a neck; such that the ballstent has at least one opening 112 or 114 without any wall structures that protrude away from or into the ballstent. FIGS. 5E and 5H depict expandable bodies that may be used as ballstents 100 or blockstents 150 with external or internal proximal necks 116.

Ultimately, the metallic expandable bodies disclosed herein may have a variety of configurations and any of the configurations may be employed for a variety of uses including occluding aneurysms and segments of biological conduits, including arteries and veins. Generally speaking, some configurations may lend themselves more readily or effectively to one application or another. For example, the spherical expandable bodies 100 of FIGS. 1A-B and 5A-B may be advantageous when acting as a ballstent for the filling of the lumen (or void) a saccular aneurysm, and the elongated expandable bodies 150 of FIGS. 1C-F and 5C-F may be advantageous when acting as a blockstent for the occluding the lumen of a segment of a biological conduit.

Figure 9A:
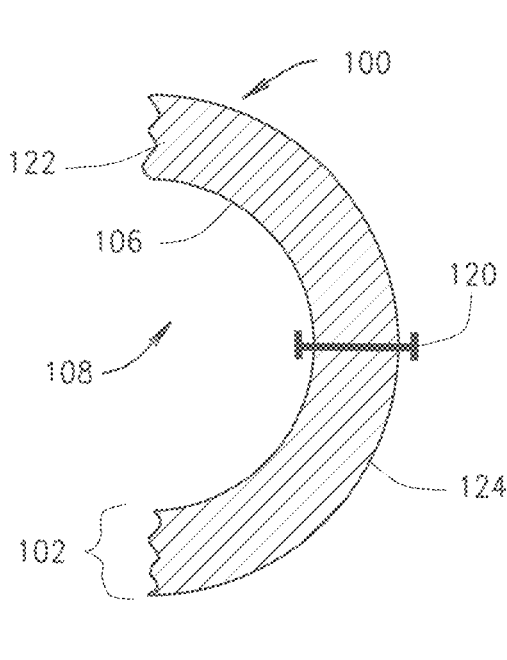
FIGS. 9A-D are hemispherical cross-sectional views taken along a diameter of embodiments of the expandable body.

The metallic expandable body, such as the ballstents 100 or blockstents of FIGS. 1A-F and 5A-F, may be composed of a single continuous layer or wall 102, as shown in FIG. 9A. The wall 102 includes a material, preferably a metal that is biocompatible and ductile, that can form a thin-wall construction, and can assume a variety of shapes after expansion. By way of example and not limitation, the metal can be selected from the group consisting of gold, platinum, silver, nickel, titanium, vanadium, aluminum, tantalum, zirconium, chromium, silver, magnesium, niobium, scandium, cobalt, palladium, manganese, molybdenum, alloys thereof, and combinations thereof. Preferred metals include gold, platinum, and silver, alloys thereof, and combinations thereof. Expandable bodies can also be made from alternative materials that can be formed into thin-walled structures that are sufficiently rigid or semi-rigid to tolerate compression and expansion, and can maintain an expanded state in vivo. Alternative materials include polymers or plastics that are reinforced with metal coils or braids, and other materials with similar properties. The materials forming the wall 102 and the thickness of the wall are selected such that the expandable body 100 or 150 has sufficient rigidity to remain in an expanded state in vivo under typical physiologic conditions after expansion and separation from the delivery catheter, even where the pressure inside and outside the central void or space 108 is the same or similar.

It is desirable that the materials used to form and support the expandable body 100 or 150 have sufficiently mechanical properties of ductility, malleability, and plasticity to be compressed or folded without tearing and later expanded without rupturing. In general, ductility is a measure of a material's ability to be deformed without breaking, while the malleability of the material determines the ease of deforming without breaking when the metal is subjected to pressure or forces. The ductility and malleability of a material factor into the plasticity of the material, which generally refers to a property of the material that permits it to undergo a permanent change in shape without rupture or breakage. As such, the expandable bodies may be composed of any biocompatible materials having sufficient ductility, malleability, and plasticity to undergo one or more compressions, folding processes, and expansions.

Figure 9B:
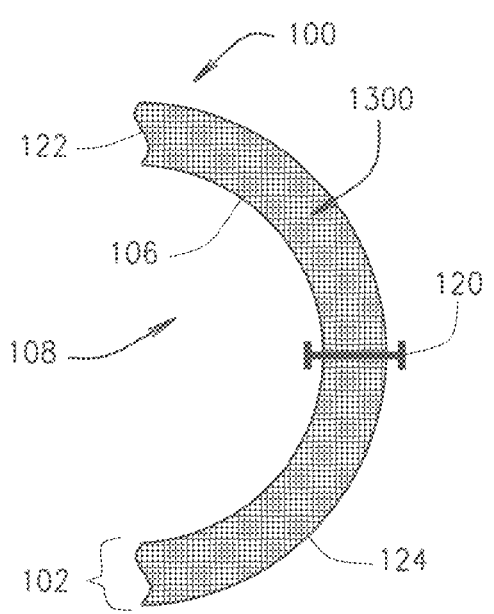

The central layer 122 of the wall 102 has an interior surface 106 and exterior surface 124 that define a wall thickness 120. In particular, for FIGS. 9A and 9B, the distance between the interior surface 106 and the exterior surface 124 is the overall wall thickness 120 of the wall 102. Preferably, the central layer 122 of the wall 102 has a thickness 120 from about 3 μm to about 50 μm and is preferably, approximately 10 μm thick. The wall thickness 120 can be uniform. For example, the wall 102 may have a uniform thickness of 3 μm, 5 μm, 10 μm, 15 μm, 20 μm, 30 μm, 40 μm, or 50 μm. Alternatively, the thickness of the wall 102 at different locations may vary in thickness. Alternatively, the expandable body 100 or 150 may be composed of a single porous layer or wall 122, as shown in FIG. 9B, with pores or microperforations 1300 wherein at least some or all of the microperforations extend all the way from the internal surface 106 to the external surface 124. For this embodiment, the wall 102 may be of a uniform thickness or a varied thickness. During expansion of the ballstent 100 of this embodiment, the fluid medium may travel under pressure from the void or space 108, through the wall 102 and leave the ballstent at the exterior surface 124. Preferably, for this embodiment, the microperforations 1300 may range from 1 μm-500 μm in diameter.

Figure 9C:
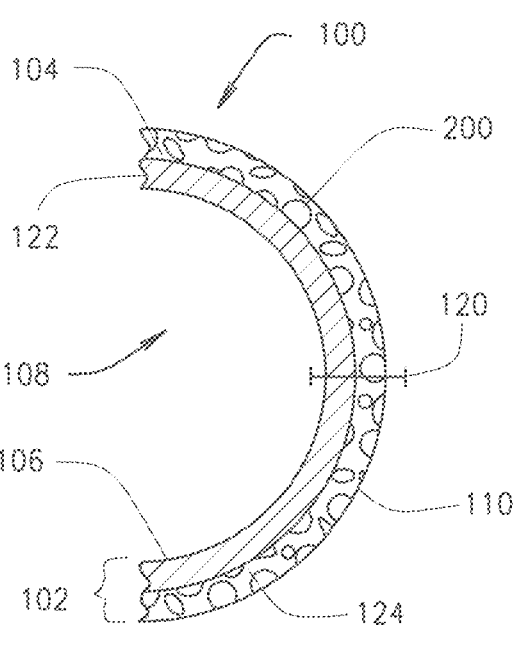

The expandable body 100 or 150 includes a central wall or layer 122, optionally with an exterior wall or layer 104, and optionally with an interior wall or layer 214, as shown in FIG. 9C. As mentioned, the construct of the central layer or wall 122 and the layers 104 and 214 can be uniform, porous, or combinations thereof. In one embodiment of the ballstent 100 used to treat an aneurysm, the wall 102 includes a plurality of microperforations 1300 that extend completely through the thickness 120 of the wall 102.

In one construction, the central layer or wall 122 is continuous and formed of gold. Optionally, to this preferred construction, an exterior layer 104 formed of porous gold can be added. Optionally, an interior layer 214 formed of Parylene™ may be present. Optionally, an exterior layer 104 formed of Parylene™ may be present. In certain embodiments where electrolysis is used to separate the expanded expandable body 100 or 150 from the delivery catheter, certain portions of the ballstent or the blockstent (such as the neck or body) are coated with an insulator or polymer, such as Parylene™. These portions include the external surface, the internal surface, or both the internal and external surfaces, while a portion of the neck or body remains uncoated or non-insulated. In this instance, the uncoated or non-insulated portion of the wall is dissolved (corroded) by the passage of an electrical current into the uncoated or non-insulated region of the wall during electrolysis. In certain embodiments, the uncoated or non-insulated portions of the wall are created by masking during the coating process. In other embodiments, the coating or insulation is removed from the uncoated or non-insulated portions of the wall, as through etching or ablation, such as with laser etching or laser ablation.

The Expandable Body Exterior

As discussed, the expandable body 100 or 150 may have one or more additional coating or layer(s) 104 on the exterior surface 124 of the central layer 122, as shown in FIG. 9C. The wall 102 and any additional exterior layers define an exterior surface 110 that, when expanded, contacts the internal wall of the aneurysm or blood vessel. The exterior layer 104 can be of a uniform or varied thickness, preferably between about 1 μm and about 59 μm. In one embodiment, the exterior layer 124 has a thickness between 0.1 μm and 10 μm. In a specific embodiment, the exterior layer 124 has a thickness of about 1 μm.

Figure 9D:
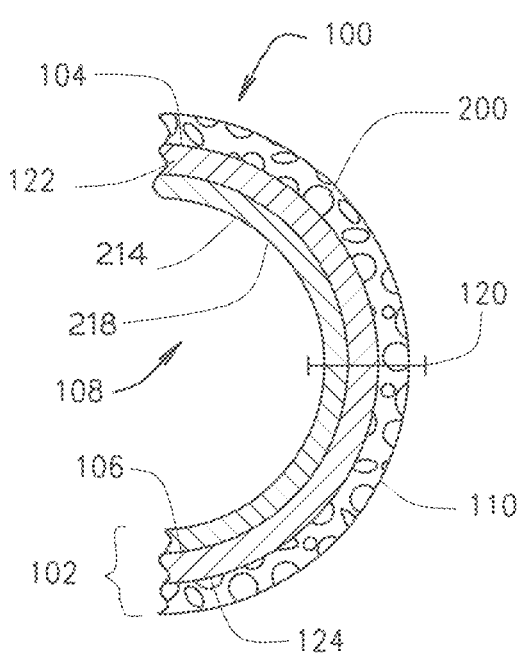
Figures 36A, 36B, 36C, 36D, 36E:
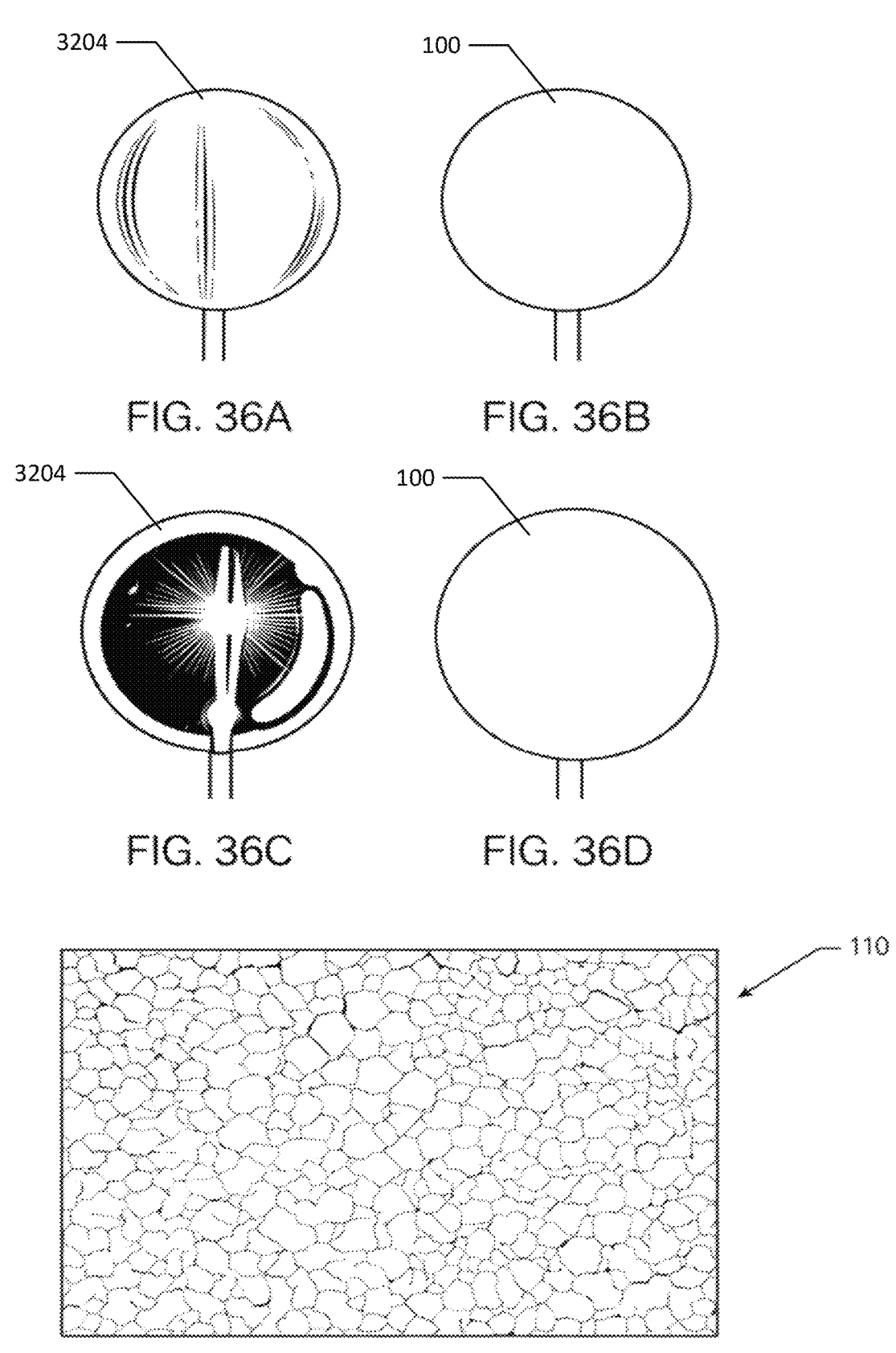
FIGS. 36A-D are photographs of various embodiments of mandrel models and metal expandable bodies formed thereon.
FIG. 36E shows an external surface of a metal expandable body according to one embodiment.

The exterior layer 124 can be formed of polymers, latex, elastomers, or metals. The exterior layer 124 may be an electric insulator, and in a preferred embodiment, the exterior layer 124 is formed of a Parylene™ coating. The exterior coating or layer 104 of the expandable body 100 or 150 may be porous and contain a plurality of pores 200, as shown in FIGS. 9C and 9D. Alternatively, the exterior layer 104 can be smooth, with limited porosity or projections. For example, the exterior layer 104 may be a polished metal surface. In one embodiment, portions of the exterior layer 104 can be smooth, while other portions can be porous or contain projections. In one embodiment, the surface variations can include a pattern. FIG. 36E depicts structures of the exterior surface 110 after electroforming. As shown, the exterior surface 110 of the wall 102 may have rounded, pebbled, or granular structures. In various embodiments, the rounded, pebbled, or granular surface structures have a height of approximately 0.1 μm to approximately 10 μm.

When configured as a porous or spongy layer, the exterior layer 104 can contain (or be configured to contain) solutions that include pharmaceutical drugs, pharmacologically active molecules, or pharmaceutical compositions within the pores 200. As such, solutions such as pharmaceutical drugs, pharmacologically active molecules, or pharmaceutical compositions can be delivered to the treatment site. Drugs, pharmacologically active molecules, or pharmaceutical compositions that promote thrombosis, stimulate cell proliferation or extracellular matrix production, or tissue growth are examples of agents that can be placed in the pores 200 of the exterior layer 104. The pharmaceutical drugs, pharmacologically active molecules, or pharmaceutical compositions are incorporated into the pores 200 of the wall or the exterior layer 104 prior to positioning the expandable body 100 or 150 at the desired location. The drug compositions may be delivered into the pores 200 via capillary or wicking action. The pores 200 range from about 0.01 μm to about 500 μm in diameter. Pore diameters for each expandable body may vary according to the specific drugs, pharmacologically active molecules, or pharmaceutical compositions to be incorporated and the desired rate of release in vivo. By way of example and not limitation, the expandable body 100 or 150 may have a porous exterior layer 104 where the pore diameter averages from about 0.01 μm to about 0.05 μm, about 0.05 μm to about 0.5 μm, 0.5 μm to about 5 μm, about 5 μm to about 25 μm, about 25 μm to about 500 μm, about 0.05 μm to about 500 μm, or about 0.01 μm to about 500 μm.

The pharmaceutical drugs, pharmacologically active molecules, or pharmaceutical compositions may include thrombin, platelet-derived growth factor, Ethiodol®, Sotradecol®, or combinations thereof. Other pharmaceutical compounds and compositions that promote thrombosis, stimulate cell proliferation, stimulate the synthesis of extracellular matrix, or the growth of tissue into the porous external wall of the expandable body 100 or 150 may also be used. Such drugs or pharmaceutical compositions may include molecules to promote cell proliferation, extracellular matrix production, or tissue growth, such that the expanded expandable body 100 or 150 will become more firmly attached to the tissue at the treatment location. The dosages and manner in which the pharmaceutical drugs, pharmacologically active molecules, or pharmaceutical compositions are incorporated into the wall 102 or exterior layer 104 are a matter of choice depending on the treatment performed. Other compounds may be used to promote blood clotting or thrombosis around the expandable body. For embodiments of the expandable body 100 or 150 with a porous layer 104, over time, the ballstent or the blockstent remains expanded with the expanded body eventually becoming affixed to the surrounding tissue.

As can be understood from FIGS. 12A-D, the exterior surface 110 of the expandable body 100 or 150 may also include one or more projections (which may be generally tubular or have other configurations) that can increase the strength of the attachment of the expanded body to the adjacent tissue, and thereby reduce the risk of movement or migration. The projections may have a length that ranges between about 0.01 μm to about 167 μm. Some projections can have a branched construction, while others may be joined on both ends to the exterior surface 110 to form loops. In some embodiments, the projections are rigid, or semi-rigid. In other embodiments, the projections are flexible and hair-like, and may further comprise globular ends, similar to the projections on the surface of the footpad of the gecko. The projections may be attached to the expandable body 100 or 150 after formation. Alternatively or additionally, the projections may be incorporated into the expandable body during electroformation.

The projections are features designed to secure the expandable body 100 or 150 in place once it has been expanded in the lumen of an aneurysm sac or blood vessel segment. These features can be biological or physical, or a combination thereof. In one embodiment, the exterior surface 110 of the expandable body 100 or 150 may be coated with molecules that can bind to adjacent thrombus or tissue. These molecules can be affixed to the expandable body 100 or 150 through a variety of methods, including chemical bonds such as with hydrogen bonding or covalent bonding. Alternatively, these molecules can be affixed through encapsulation of the porous layer or encapsulation of various projections. Representative molecules that can be affixed to the wall of the ballstent 100 or the blockstent 150 include fibrin, and molecules that can link to fibrin through covalent and non-covalent bonding. With such a coating, the expandable body 100 or 150 can be anchored to the fibrin-rich clot that forms between the wall of an aneurysm and the ballstent 100 or between the wall of a blood vessel segment and the blockstent 150.

In another embodiment, the ballstent 100 may comprise a porous external layer or wall 104 or a wall with external projections to promote thrombus formation on the external surface 110 or in the pores 200 and promote cell proliferation, extracellular matrix production, or tissue growth into or around the wall 102 of the ballstent 100 such that the ballstent 100 will, over time, become more strongly attached to the tissue in the adjacent aneurysm wall.

Figures 12A, 12B, 12C, 12D:
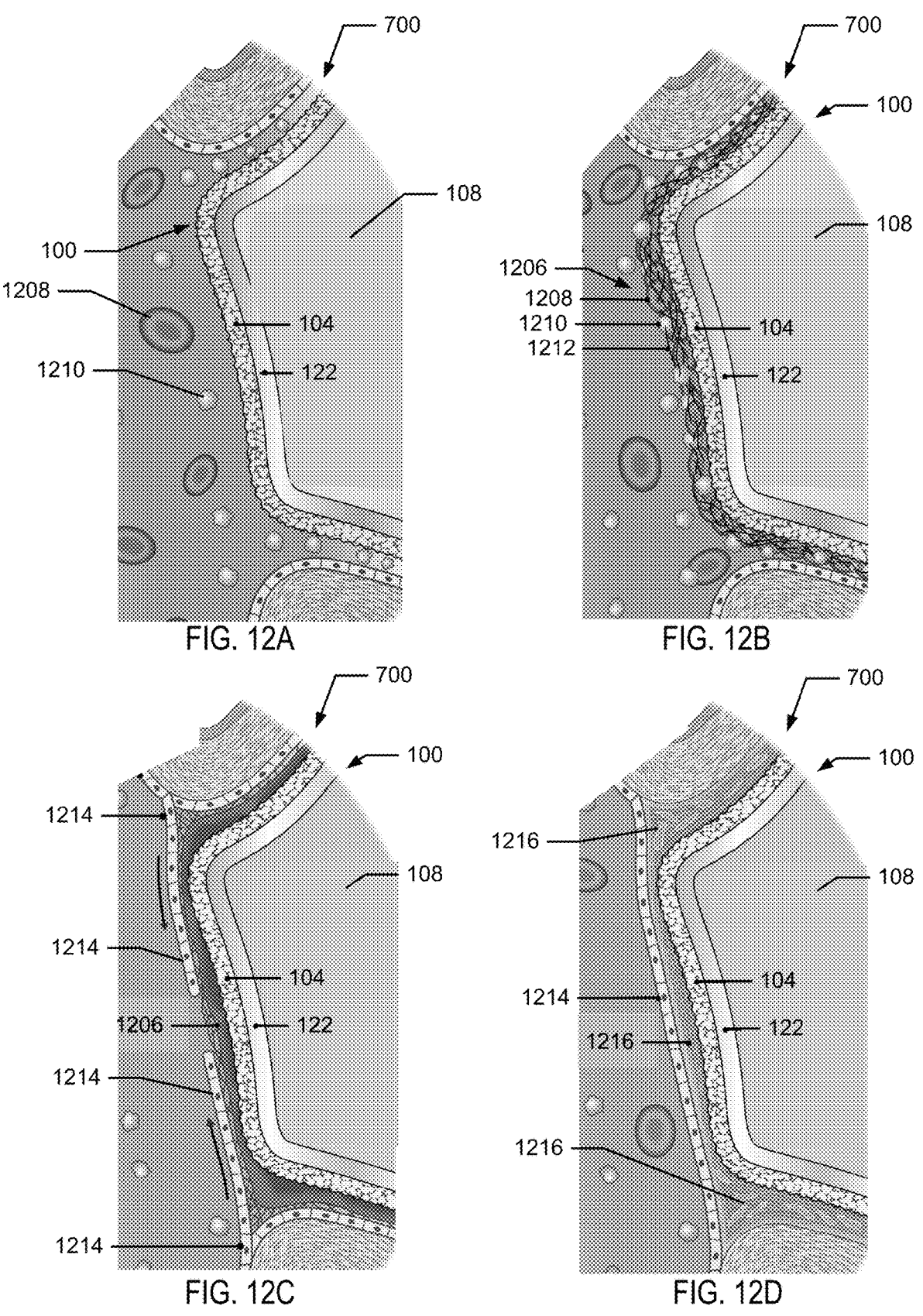
FIGS. 12A-E are plan views of embodiments of a ballstent and blockstent with a porous surface layer facilitating tissue ingrowths in an aneurysm.
Figure 12E:
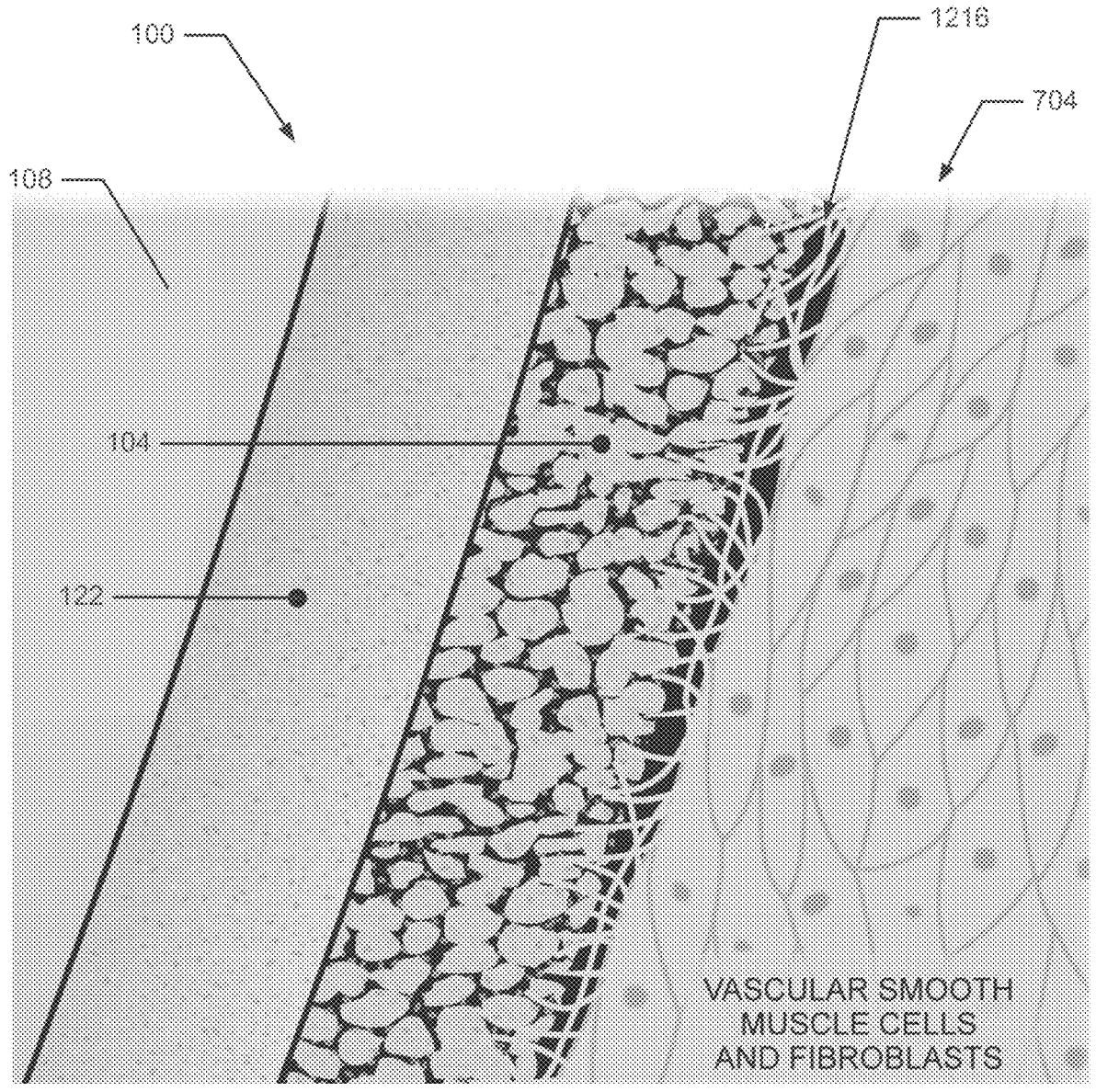

As shown in FIGS. 12A-D, the central layer 122 and the porous exterior layer 104 of the ballstent 100 placed into the aneurysm 700 may be configured to promote thrombus 1206 formation on the exterior layer. The thrombus may be comprised of red blood cells 1208, platelets 1210, and fibrin 1212. Overtime, the thrombus 1206 may be partially absorbed into the exterior layer 104, as new endothelial cells 1214 are formed over the thrombus. The new endothelial cells may form a seal of connective tissue 1216 across the opening of aneurysm 700. In addition to sealing the opening of the aneurysm 700, connective tissue 1216 from the wall 704 of the aneurysm may grow into the porous exterior layer 104 of the ballstent 100 to adhere the ballstent to the wall of the aneurysm, as shown in FIG. 12E.

In other embodiments, the projections may be generally tubular, straight, curved, hook-shaped, or configured as pigtail hooks 1800 as shown in FIGS. 12F-G. The projections may improve the attachment of the blockstent 150 within a blood vessel, as illustrated in FIGS. 12H-I. In another embodiment, the exterior surface 124 or 110 of the expandable body 100 or 150 further comprises one or more projections therefrom, which can be used to anchor the expandable body 100 or 150 to the surrounding tissue, specifically the wall a saccular aneurysm or a biological conduit such as an artery or vein, and hold the expandable body in the desired location. In a macroscopic form, the projections may be composed of nitinol or any other suitable biocompatible material.

FIG. 12G depicts an expanded ballstent 100 that is anchored to the wall 704 of an aneurysm 700. The size and shape of the projections may be selected based upon the condition being treated, and may be designed and dimensioned to provide sufficient anchoring support without causing excessive damage to the wall of the aneurysm or the surrounding tissue. Alternatively, microscopic projections or filaments may be used to anchor the ballstent. For some embodiments, these microscopic projections range in length from 0.01 μm to about 57 μm, and can be straight or branching. In various embodiments, both ends of one or more of the projections may be joined to the exterior surface 110 of the ballstent 100 and/or the exterior surface 216 of the wall 102 to form a loop. Similarly, FIG. 12H depicts an expanded blockstent 150 having pigtail hooks 1800, while FIG. 12I depicts an expanded blockstent 150 that is anchored to the wall 1802 of a blood vessel 1804.

The Expandable Body Interior

In some embodiments, the expandable body 100 or 150 may include an additional layer or liner 214 on the interior surface 106 of the central layer 122, as shown in FIGS. 9D, 9F, 9H, 9J, and 9L. The interior layer may be made from the same materials as the central layer, or can be made of different materials. The interior layer may be formed of gold, platinum, silver, alloys thereof, or combinations thereof. The additional layer 214 on the interior surface 106 of the central layer 122 of the expandable body 100 or 150 may also be formed of a polymer, plastic, latex, rubber, woven or knitted fiber material, metal, or another material, or combinations thereof. Preferably, the interior layer 214 is an elastomeric coating that is bonded to the interior surface 106 of the central layer 122. The interior layer 214 can be a variety of thicknesses, preferably ranging between about 0.1 μm and about 59 μm. In one embodiment, the interior layer 214 has a thickness between about 0.1 μm and about 10 μm. The total thickness of the wall 102, including the central layer 122, the exterior layer 104, and the interior layer 214 is preferably between about 2 μm and about 50 μm, regardless if the wall contains one, two, three, or more layers. The interior layer 214 can be comprised of polymers, latex, or elastomers. In a preferred embodiment, the interior layer 214 is comprised of Parylene™. The interior layer 214 also adds mechanical properties (such as strength) to the wall 102. Further, the interior layer 214, optionally, can form a seal that prevents the escape of a fluid medium from the expandable body 100 or 150, should the central layer 122 contain a defect or hole. The central layer 122 and any additional layers define an interior surface 106 or 218, respectively, such that when the ballstent or the blockstent is expanded, with a fluid, liquid, gas, or solid, a central void or space 108 is defined. As shown in FIG. 9D, the distance between the interior surface 218 and the exterior surface 110 is the overall wall thickness 120 of the wall 102.

The Expandable Body Neck(s) and Opening(s)

As illustrated in FIGS. 1A-H, and FIGS. 5A-H, the ballstent 100 and the blockstent 150 have one or more openings 112 and 114 defined by the wall 102 or by one or more necks 116 and 118. In various embodiments, the ballstent or blockstent have one or more openings 112 and 114 defined by necks 116 or 118 (see FIGS. 1A, 1C, 1E, 1G, 5A, 5C, 5E, and 5G) or one or more openings 112 and 114 but do not have necks 116 or 118 (see FIGS. 1B, 1D, 1F, 1H, 5B, 5D, 5F, and 5H). In all embodiments, a fluid medium can enter the opening 112 and move into the central void or space 108 defined by the interior surface 106 or 218, thereby expanding the expandable body. In various embodiments, one or both of the necks 116 and 118 may extend outwardly from its respective end region of the ballstent 100 and blockstent 150 as shown in FIGS. 1A, 1C, 1E, 1G, 5A, 5C, 5E, and 5G. Alternately, one or both of the necks 116 and 118 may extend inwardly from its respective end region and into the interior void 108, as illustrated in FIGS. 1B, 1D, 1F, 1H, 5B, 5D, 5F, and 5H. The proximal necks 116 can be used for attaching the expandable body 100 or 150 to the delivery catheter and may function in separating the ballstent or the blockstent from the delivery catheter. In various embodiments, the necks 116 and 118 and the wall 102 may be formed by different metals. For example, in one embodiment, the neck(s) 116 and 118 and the wall 102 may be formed by gold. In other embodiments, the neck 116 and 118 may comprise stainless steel and the wall 102 may be formed by gold, platinum, or another malleable metal. The neck 116 and 118 may comprise multiple metals, such as stainless steel and another metal such as gold or platinum, including embodiments wherein the various regions of the expandable bodies 100 and 150 are distinct in their metal content and embodiments wherein the different metals are formed in layers in the various regions.

Figures 37E, 37F, 37G, 37H:
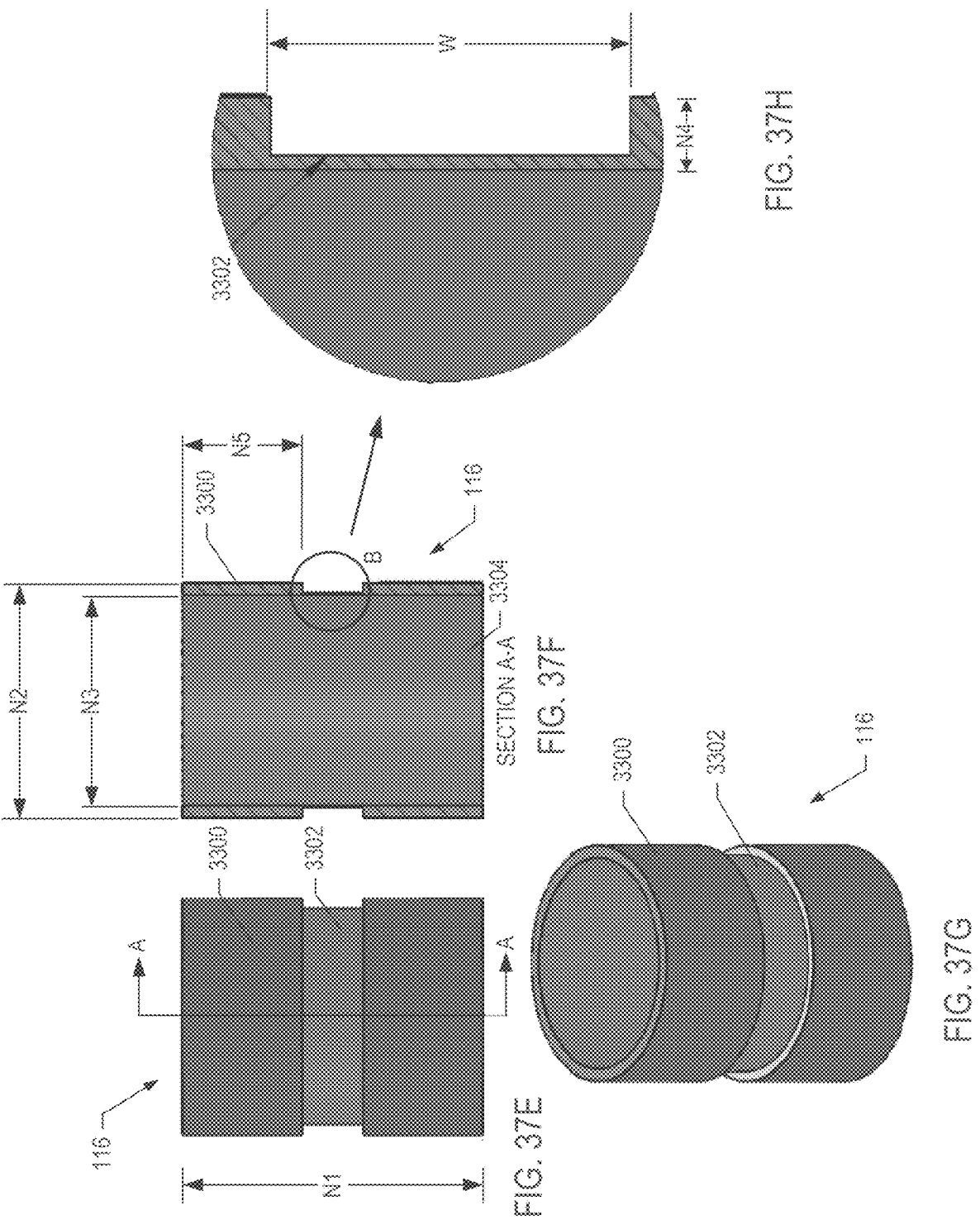

Additionally, the necks 116 and 118 can be designed and dimensioned such that the opening 112 or 114 can be closed or partially closed before, during, or after separation of the expanded body from the delivery catheter. One or more openings 112 or 114 may remain open. Optionally, before, during, or after separation, the necks 116 and 118 may be folded, pinched, or closed to form a seal. The necks 116 and 118 have a length N1, as shown in FIGS. 31A and 37E, ranging between about 0.5 mm and about 20 mm, preferably a length between about 0.5 mm and about 5 mm. In one embodiment, the neck length N1 is approximately 1.27 mm±0.08 mm.

The necks 116 and 118 have an outer diameter N2 and an inner diameter N3 that defines the openings 112 and 114, respectively. The outer diameter N2 is in a range between about 0.25 mm and about 2 mm and the inner diameter N3 is in a range between about 0.24 mm and about 1.95 mm as shown in FIG. 37F. In one embodiment, the neck outer diameter N2 is approximately 0.99 mm+0.01 mm and the neck inner diameter N3 is approximately 0.89 mm+0.01 mm.

The thickness of the walls of either or both of the necks 116 and 118 may be the same as the main body of the ballstent or the blockstent or may be thinner or thicker than the wall of main body. Preferably, either or both of the necks 116 and 118 have a wall thickness N4 between about 3.0 μm and about 60.0 μm, as shown in FIG. 37H, which is a close-up view of region B from FIG. 37F. In one particular embodiment, the neck has a thickness of approximately 50.0 μm. In one embodiment of the ballstent 100 where the neck(s) 116 and 118 extend into the central void space 108 as indicated in FIGS. 1B and 5B, the external surface 110 of the expanded ballstent retains a more rounded surface contour, to increase the strength of the expanded ballstent and to reduce risk of damage to the aneurysm wall or the adjacent tissue during placement of the ballstent.

Figure 29A:
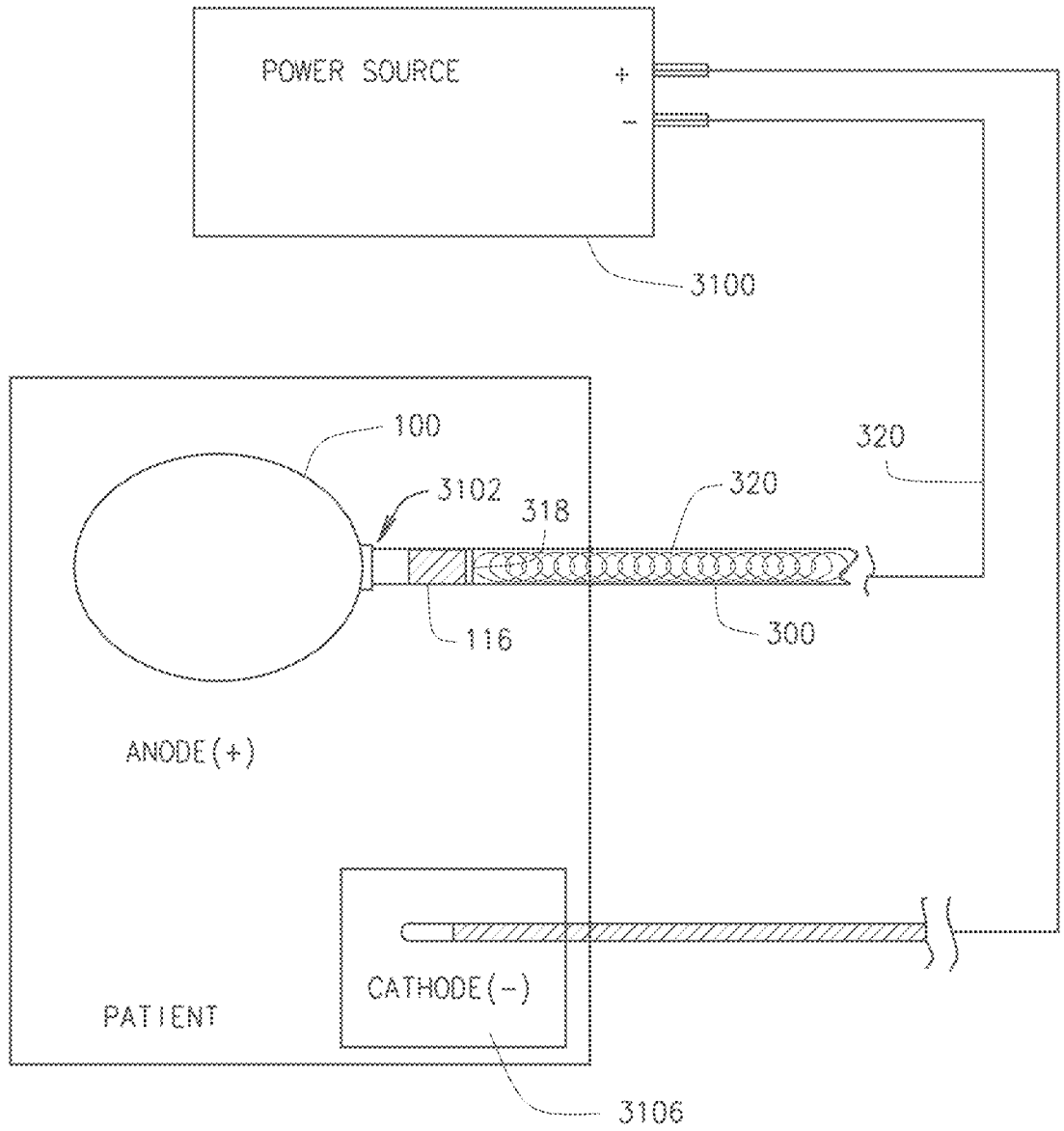
FIG. 29A is a plan view an embodiment of the medical device wherein the expandable body is attached to the delivery catheter with an adhesive and separated from the delivery catheter by electrolysis of a portion of the neck of the expandable body.

One or both of the necks 116 or 118 can be coated or insulated on the inner wall, outer wall, or both. In some embodiments, a strip of conductive material, including an uncoated or non-insulated section of a weld or solder, or portion of the ballstent or the blockstent itself, is left exposed, uncoated, or non-insulated or later exposed after coating to form a ring-shaped exposed surface of metal or conductive materials that can be subjected to electrolysis to achieve separation between the expanded expandable body and the distal end of the delivery device. For example, as can be understood from FIGS. 9E, 9G, 9I, 9K, 35, and 37A-37D, in one embodiment, at least a portion of an inner surface of the metal layer of the neck of the metallic expandable body is electrically insulated by having an outer surface of a distal portion of the delivery device extending along the inner surface of the metal layer of the neck of the metallic expandable body. For the inner surface of the neck 116, a proximal boundary of the ring-shaped exposed metal surface may be defined by a distal boundary of the delivery device in the neck region and a distal boundary of the ring-shaped exposed metal surface may be defined by a boundary of the inner insulation layer in the neck region. For the outer surface of the neck 116, both the proximal and distal boundary of the ring-shaped exposed metal surface may be defined by a boundary of the outer insulation layer in the neck region. In such an embodiment, the distal end of the delivery device may distally terminate near a proximal edge of the ring-shaped exposed metal surface of the neck. As indicated in FIG. 29A, a conductive wire can be engaged in electrical contact with the uncoated or non-insulated portion of the weld or solder, or expandable body 100 or 150 to allow the uncoated or non-insulated portion to be dissolved (corroded) or removed via electrolysis.

Figure 22:
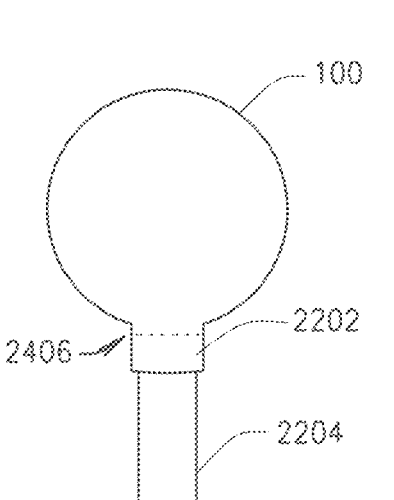
FIG. 22 is a plan view of a component and a method for separating an expandable body from a delivery catheter.

In other embodiments, one or both necks 116 and 118 may be scored to create a number of circumferential perforations 2406, as shown in FIG. 22. The perforations may be torn to detach the expandable body from a delivery device, as explained more fully below regarding methods to detach an expanded expandable body 100 or 150.

Expandable Body Shapes and Dimensions

FIGS. 9E-9F and 9I-9J illustrate a ballstent 100 and a catheter 220 that may be used to deliver the ballstent. The ballstent 100 includes a distal region 202 that includes the distal end 204 of the ballstent. Adjacent to the distal region 202 is an intermediate region 206 where the ballstent transitions from the distal region 202 to a proximal region 208 that includes a proximal end 210 of the ballstent. The proximal region 208 is generally opposite the distal region 202. A center axis 212 extends proximal-distal between the proximal region 208 and the distal region 202. The ballstent wall 102 extends generally continuously through the intermediate region 206 from the distal region 202 to the proximal region 208. The ballstent 100 is in the form of a single lobed metallic expandable body.

In one embodiment, when the ballstent 100 is expanded, the intermediate region 206, the proximal region 208, and the distal region 202 combine to form a generally spherical shape. In various embodiments, the dimensions of the ballstents 100 are selected based upon the size and shape of the saccular aneurysm being treated. Preferred shapes of the ballstent 100 include round, oblong, and irregular. The diameter of the round expanded ballstent 100 ranges from about 2 mm to about 30 mm, and preferably has an expanded diameter ranging from about 2 mm to about 20 mm. The expanded length of oblong ballstents preferably ranges between about 2 mm to about 30 mm. The ballstent 100 may have an expanded volume that ranges between about 0.001 cc to about 65 cc. In preferred embodiments, the expanded diameter of the spherical ballstent 100 ranges from about 2 mm to about 10 mm, while the preferred expanded volume ranges from about 0.004 cc to about 40 cc. In preferred embodiments, the expanded length of the oblong ballstent 100 ranges between about 2 mm to about 30 mm. By way of example and not limitation, FIG. 30A provides exemplary dimensions for an embodiment of the spherical ballstent 100.

FIGS. 9G-9H and 9K-9L illustrate a block stent 150 and a catheter 220 that may be used to deliver the blockstent. In such an embodiment, the blockstent 150 includes a generally cylindrical intermediate region 206, a generally hemispherical proximal region 208 and, a generally hemispherical distal region 208. In this embodiment, the intermediate region 206 may have a radius R1 that is equal to the radius R2 of both the proximal region 208 and the distal region 208, as shown in FIG. 31A. In various embodiments, the catheter 220 is typically engaged to the proximal region 208 of the expandable body.

In other embodiments, one or more portions of the expandable body wall 102 may be thicker than the remaining portions of the wall. By way of example and not limitation, the wall in the middle of the body of the expandable body may be thicker or thinner than the wall in the proximal and distal portions of the expandable body, or the wall of a neck may be thicker or thinner than the main body of the expandable body. In various embodiments, the wall thickness 120, as shown in FIGS. 9A-D, may be scaled relative to the overall diameter of the expandable body to avoid undesired increases in wall stress with increases in diameter. In various embodiments of the expandable body 100 or 150, a balance should be stuck between a wall thickness 120 that is thin enough to enable the various small compressed forms of the delivery configuration and to permit expansion of the expandable body at lower pressures and a wall thickness that is thick enough to resist compression after delivery and detachment. Therefore, the average wall thickness 120 is preferably in a range between about 10.0 μm and about 50.0 μm. By way of example and not limitation, the wall thickness 120 for an expandable body 100 or 150 having an expanded diameter of about 4.0 mm may be about 10.0 μm, while the wall thickness for an expandable body having an expanded diameter of about 10.0 mm may be about 25.0 μm.

Figures 9E, 9F, 9G, 9H:
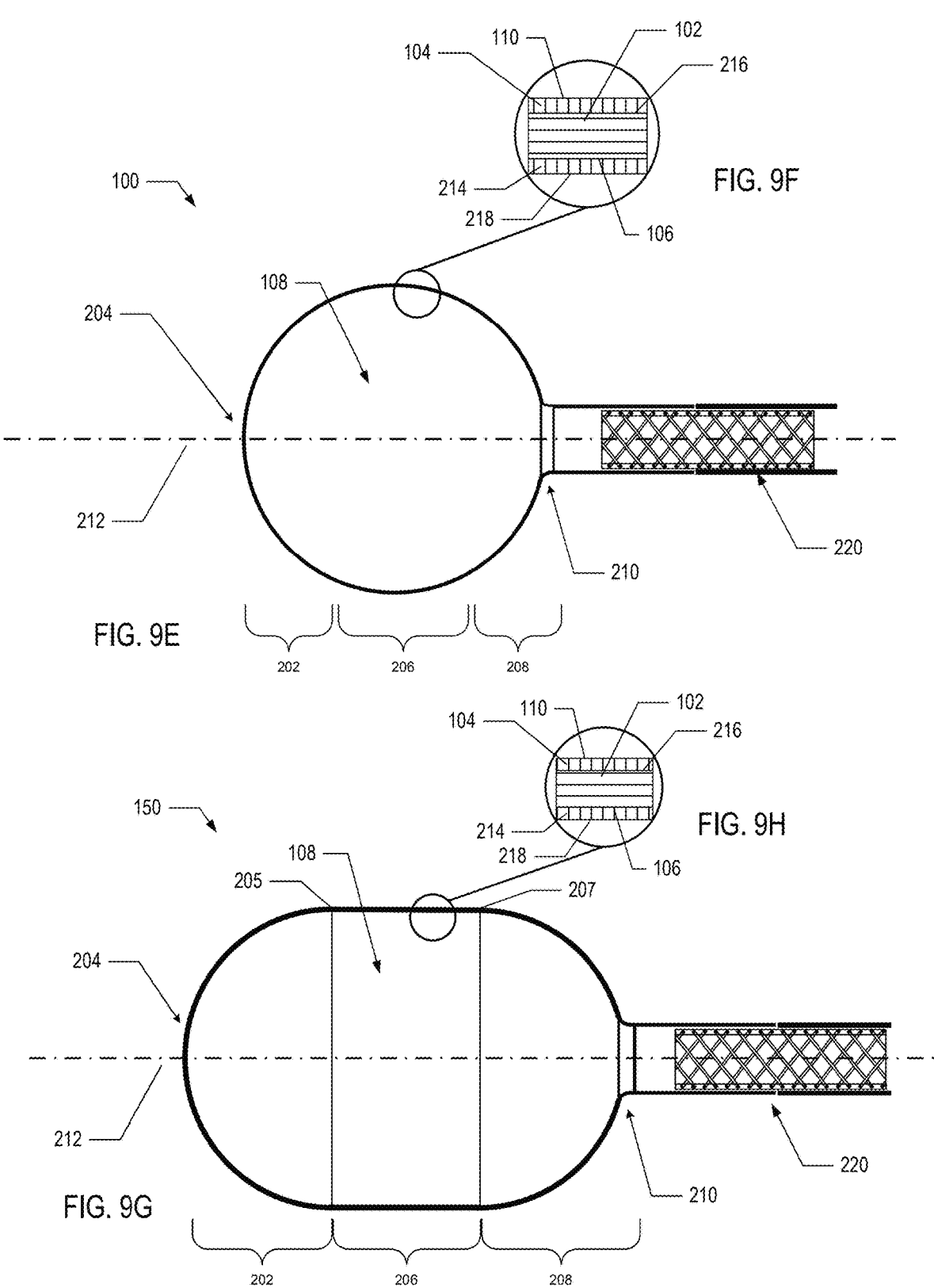
FIG. 9E is a longitudinal cross-section of the expandable body supported on a distal end of a delivery catheter, wherein the expandable body is spherical and may be employed as an embodiment of a ballstent.
FIG. 9F is a partial cross-section through the wall of the ballstent of FIG. 9E.
FIG. 9G is a longitudinal cross-section of the expandable body supported on a distal end of a delivery catheter, wherein the expandable body is cylindrical with hemispherical ends and may be employed as an embodiment of a ballstent or blockstent.
FIG. 9H is a partial cross-section through the wall of the expandable body of FIG. 9G.
Figures 9I, 9J, 9K, 9L:
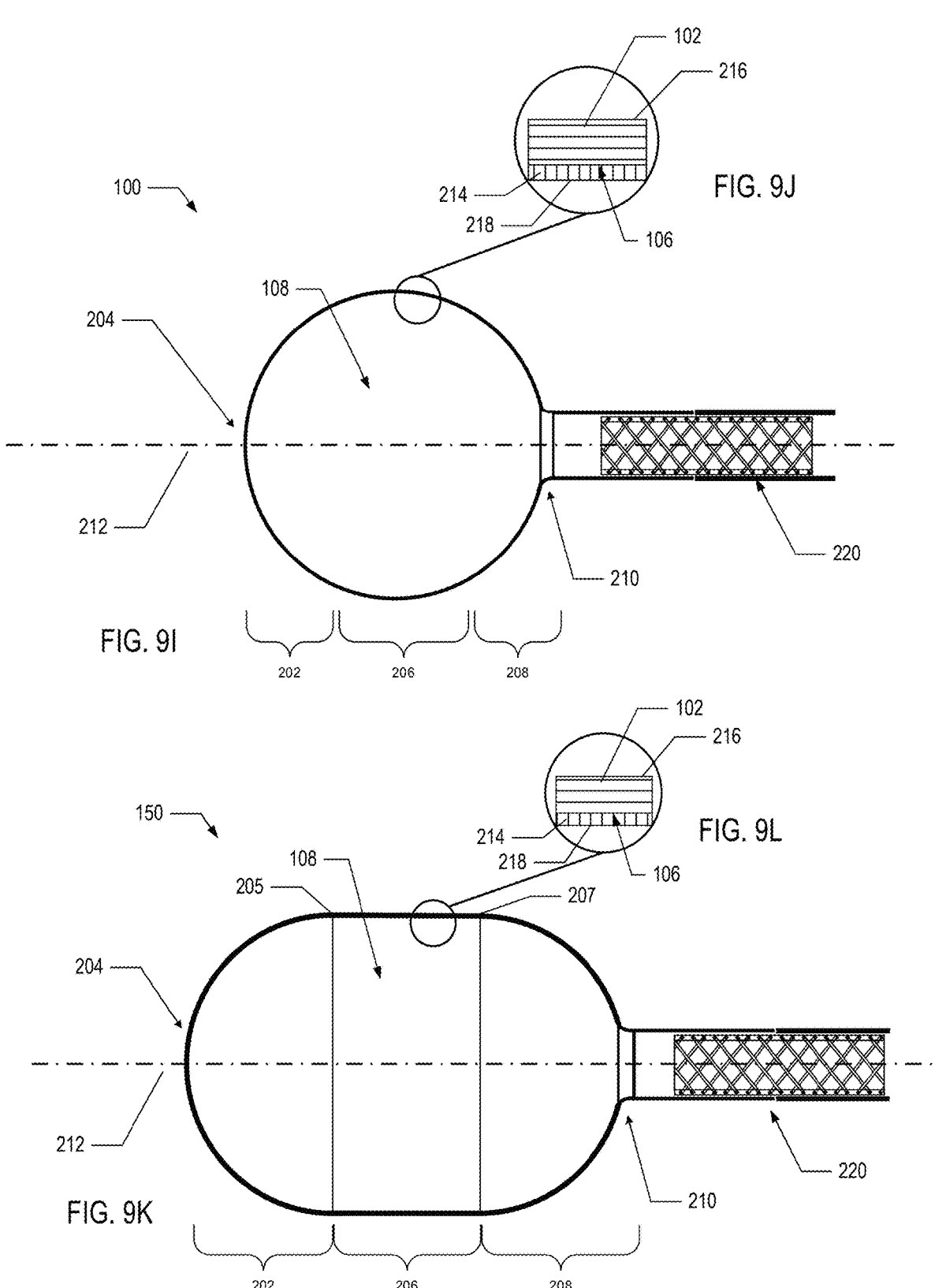
FIG. 9I is a longitudinal cross-section of the expandable body supported on a distal end of a delivery catheter, wherein the expandable body is spherical and may be employed as an embodiment of a ballstent.
FIG. 9J is a partial cross-section through the wall of the ballstent of FIG. 9I.
FIG. 9K is a longitudinal cross-section of the expandable body supported on a distal end of a delivery catheter, wherein the expandable body is cylindrical with hemispherical ends and may be employed as an embodiment of a ballstent or blockstent.
FIG. 9L is a partial cross-section through the wall of the expandable body of FIG. 9K.

As shown in FIG. 31A, the blockstent 150 may have a generally cylindrical shape with rounded or hemispherical ends. In other embodiments, the blockstent 150 may have a generally cylindrical shape with flattened or flat ends as shown in FIGS. 9H and 9K, such that the total length of the blockstent is approximately equal to the length of the intermediate region 206. The blockstent 150 is in the form of a single lobed metallic expandable body.

The near right angles formed between the intermediate region 206 and the distal end 204 and between the intermediate region 206 and the proximal end 210 may create a concentration of stresses that may affect the overall structural strength of the blockstent. To reduce this stress concentration, the intersections 205 and 207 of the intermediate region 206 with the distal and proximal ends 204 and 210, respectively, has as a radius R3, (see FIG. 31A). As R3 increases, the concentration of stress at the intersections 205 and 207 is reduced. Conversely, if R3 is too large, the subsequent changes to the geometry of the hemispherical distal and proximal ends 202 and 208, respectively, may compromise the structural strength of the blockstent. Therefore, an optimal configuration of the blockstent 150 includes intersections 205 and 207 having a radius R3 that is limited to less than approximately 10-20% of the radius R2 (see FIG. 31A) of the hemispherical distal and proximal ends 202 and 208.

Figure 31D:
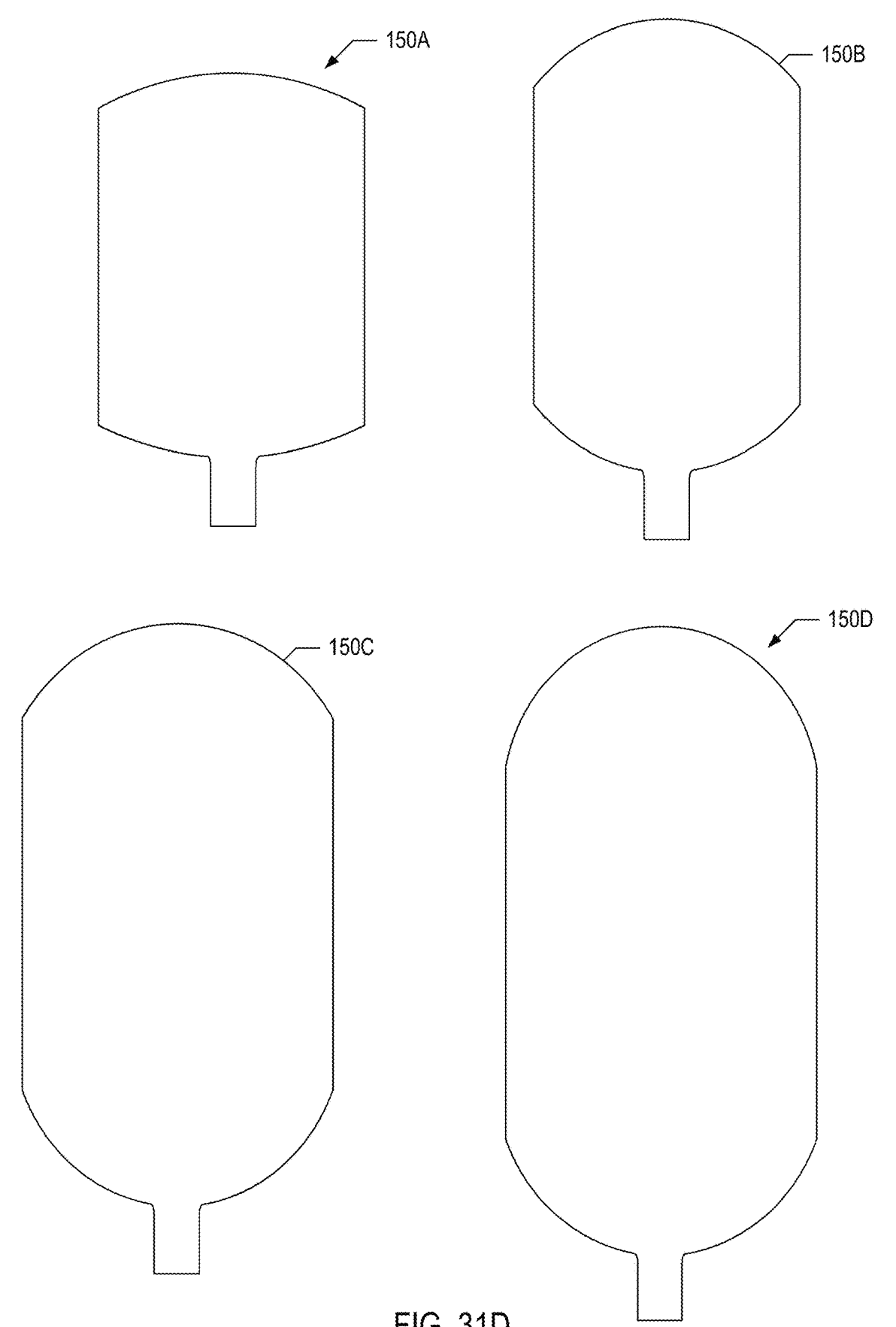
FIG. 31D depicts various shapes for expandable bodies when in the form having a cylindrical intermediate portion and hemispherical ends.

In various embodiments, the blockstent 150 has an expanded diameter ranging from about 2 mm to about 30 mm. Assuming no change in wall thickness 120, the stress in the wall of expandable body 100 or 150 will increase, as the radius R1 (see FIG. 31A) of the intermediate region 206 increases. Therefore, in some embodiments, the diameter of the blockstent 150 is limited by the ultimate tensile strength of the material (e.g. gold) used to form the blockstent and by the pressure required to expand the compressed blockstent. As can be understood from FIG. 31A, the blockstent 150 may have an expanded length L1 of between about 2 mm to about 120 mm. Preferably, the length is between about 5 mm to about 60 mm, and in a particular embodiment the expanded length L1 is approximately 40 mm+0.03 mm and the length L2 of the intermediate region 206 may be approximately 24 mm+0.03 mm. FIG. 31D depicts a variety of oblong blockstents 150A-D representative of various embodiments.

The concentration of stress between the neck 116 and the proximal end 208 of the expandable body 100 or 150 may be reduced or offset by increasing the radius R4 between the neck and the proximal end, as shown in FIGS. 31B-C. For example, the stress experienced by the wall 102 in FIG. 31B having a radius of R4 is greater than the stress experienced by the wall in FIG. 31C having a radius of R4', where R4' is greater than R4. In addition, stress may be concentrated at the point where the neck 116 transitions to the wall of the proximal end 208 of the expandable body 100 or 150 due to a metallic ring incorporated into the neck 116 during formation of the expandable body. This stress concentration may be mitigated by reducing the overall wall thickness N4 of the neck 116. By way of example and not limitation, the neck 116 shown in FIG. 31B may have a wall thickness N4 of approximately 25.0 μm, while the neck shown in FIG. 31C may have a wall thickness N4' of approximately 12.5 μm.

Expansion of the Expandable Body

The central void or space 108 of the expandable body 100 or 150 can be filled with fluids, gels, solids, or combinations thereof to expand or inflate the expandable body 100 or 150. The terms expand, inflate, and forms thereof may be used interchangeable to refer to the action of changing the expandable body from the delivery configuration to an expanded or at least partially expanded configuration. A fluid medium is a substance having particles that easily move and change their relative position without a separation of the mass. Fluid media that may be used to expand the expandable body 100 or 150 include liquids, gases, gels, and combinations thereof. By way of example and not limitation, the fluid medium may be water, a saline solution, a radiographic contrast solution, or a mixture thereof. In one embodiment, the fluid medium may further include a solution or suspension of a drug, pharmacologically active molecules, or a pharmaceutical preparation.

In various embodiments, the shape and multi-layer construction of the expandable body 100 or 150 permits the expandable body to remain in an inflated or expanded configuration without the use of any support structures not derived from the patient. For example, the fluid medium used to inflate the expandable body 100 or 150, and optionally blood from the patient, will fill the interior void 108 and cause the ballstent or the blockstent to remain in an expanded configuration. In addition, support structures derived from the patient, including but not limited to blood clots and tissue ingrowths, may support and maintain the structural integrity of the expanded ballstent 100 or the blockstent 150.

In one embodiment, the microperforations 1300 also aid in maintaining the structural integrity of the expanded expandable body 100 or 150 when treating an aneurysm by permitting fluid to traverse the wall 102 of the expandable body, thereby maintaining a pressure equilibrium between the interior void 108 and the exterior environment of the expandable body. The microperforations 1300 may also aid in maintaining the structural integrity of the expanded expandable body 100 or 150 when treating an aneurysm by permitting the growth of tissue to traverse the wall 102 of the expandable body, thereby maintaining a firm attachment between the expandable body and the adjacent tissue. Such microperforations may be advantageous in some embodiments of the ballstent 100. Conversely, in some embodiments of the blockstent 150, the microperforations 1300 may be disadvantageous as permitting fluid components of the blood to traverse the wall 102 of the blockstent may prevent the blockstent 150 from completely occluding the desired blood vessel or conduit.

Figures 10A, 10B:
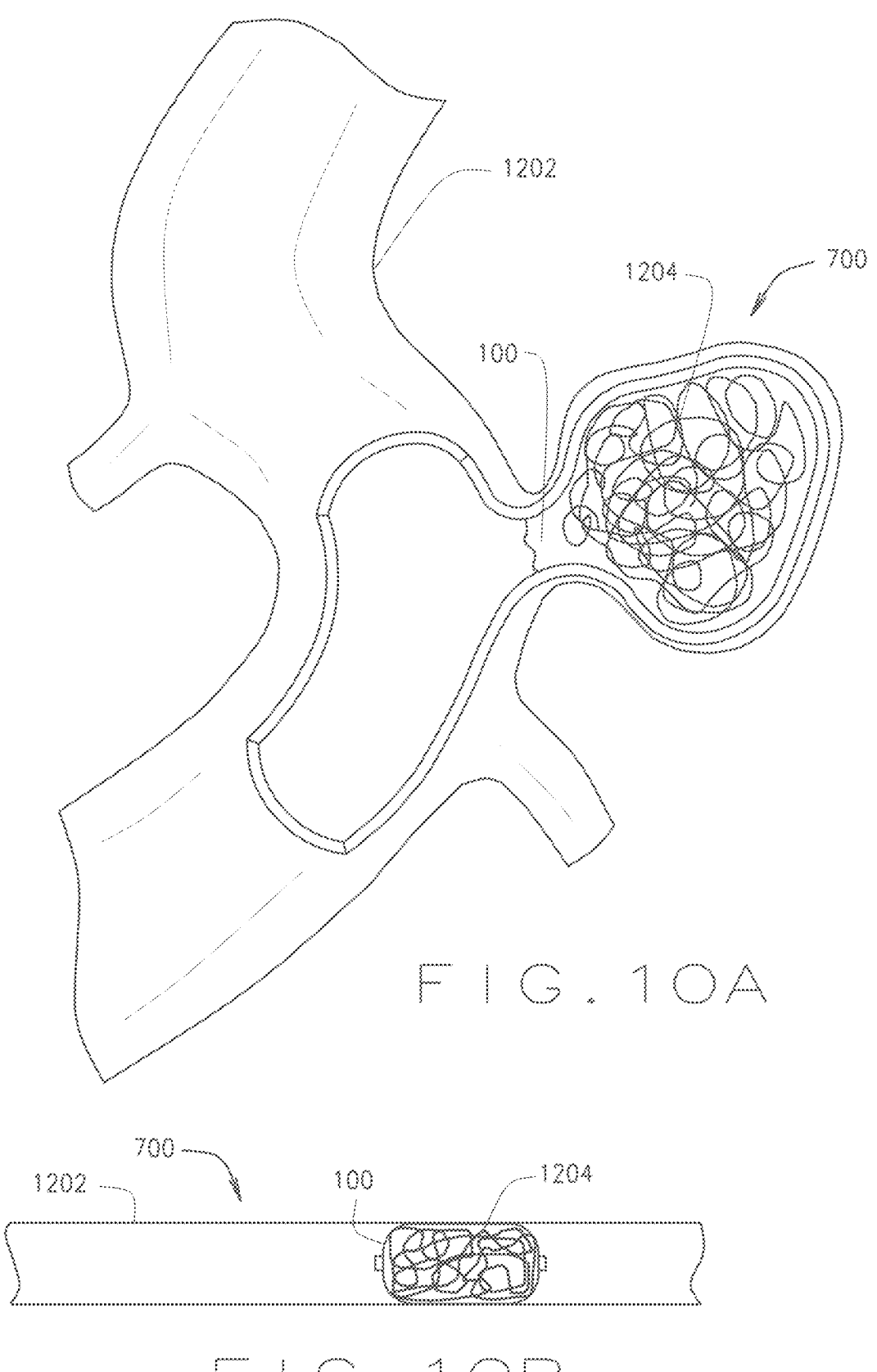
FIGS. 10A-B are plan views of the ballstent and blockstent, respectively, after the insertion of an internal support structure.

In another embodiment, the shape of an expanded expandable body 100 or 150 is maintained by placing solid material or support structures into the central void or space 108. Examples of this solid material include metal or polymeric coils or wires, metal or polymeric solid support structures, bioresorbable materials, radially expansile materials, beads, particles, granules, spheres, or microspheres. In certain embodiments, these solid materials can also be used to help expand the expandable body 100 or 150. In other embodiments, these solid materials are added after expansion. In one embodiment, as shown in FIG. 10A, the aneurysm 700 within the blood vessel 1202 is filled with a ballstent 100 containing at least one coil or expansile wire 1204. In another embodiment, as shown in FIG. 10B, the lumen 1202 of the blood vessel segment 720 is filled with a blockstent 150 containing at least one coil or expansile wire 1204. In one aspect, the expandable body 100 or 150 may be expanded by the coil or expansile wire 1204 only. In other aspects, the expandable body 100 or 150 may be expanded by a fluid medium, and the solid materials may be added later to provide support to maintain the expanded shape of the expandable body, or vice versa. Other suitable biocompatible solid materials may also be used. The solid fill members can function as a lattice to insure the structural integrity of the expandable body 100 or 150. For example, the coil 1204 can promote the structural integrity of the expandable body 100 or 150 and reduce compression of the expandable body 100 or 150. In one embodiment, solid material may be designed and manufactured to match an expandable body of a particular size or shape, and may be packaged as part of the medical device for use with the packaged expandable body.

In the event that the expandable body 100 or 150 is not appropriately sized or positioned for the desired treatment, the expandable body may be intentionally collapsed and recaptured. In one embodiment, where the expandable body 100 or 150 is still attached to the delivery catheter, a negative pressure can be generated within the delivery catheter to assist in the collapse of the expandable body. In this embodiment, the expandable body 100 or 150 may re-collapse due to the vacuum pressure alone.

In other embodiments, additional efforts are necessary to collapse the expandable body 100 or 150 after deployment due to the inherently stable geometry of expandable body. Additionally, structural features may be incorporated into the expandable body 100 or 150 to facilitate an intentional collapse. For example, a series of vertical grooves may be created in expandable body 100 or 150 during the electro-formation process to create geometric stress concentrations that encourage collapse under sufficient vacuum pressure. Another example is to coat the expandable body 100 or 150 with a thick polymer coating and then remove a majority of the thick polymer coating by laser etching to leave a series of "ribs" along exterior surface 110 of the expandable body 100 or 150. The ribs may be formed laterally or longitudinally around the expandable body 100 or 150.

In other embodiments, one or more tools designed to collapse the expandable body 100 or 150 may be used. In one example, an elongated tubular collapsing tool having a number of outwardly biased or splayed "fingers" may be inserted into a guide catheter. The fingers are collapsed inward when the collapsing tool is inserted into the guide catheter and over the delivery catheter. When the collapsing tool exits the distal end of the guide catheter, the fingers spring out radially and encircle the expanded expandable body 100 or 150. The collapsing tool is the retracted back into the guide catheter such that the fingers engage and compress and deflate the expanded expandable body 100 or 150. A vacuum may also be applied throughout the process to encourage collapse of the expandable body 100 or 150.

The Expandable Body in Use

Advantageously, as illustrated in FIG. 11A, the ballstent 100 can be delivered into the lumen 701 of a saccular aneurysm 700, expanded, and then separated from the delivery catheter 300, such that the delivery catheter can be removed while the expanded ballstent remains in place filling a portion, substantially all, or all of the lumen of the aneurysm in an expanded state. The expanded ballstent 100 will typically conform to the shape of the saccular aneurysm cavity in which it is placed. The expanded ballstent 100 can also be shaped with external force, such as a physical force applied by the inflated balloon portion 1102 of an adjacent balloon catheter 1100, as shown in FIG. 11A. With precise placement and shaping, the ballstent 100 can be positioned such that the aneurysm lumen 701 or cavity is completely or substantially filled and sealed, and further with none of the ballstent, or a minimal amount of the ballstent, extending into the lumen of the parent vessel 1202 from which the aneurysm has formed. In another embodiment, the expanded blockstent 150 can also be shaped with external force, such as a physical force applied by the inflated balloon portion 1102 of an adjacent balloon catheter 1100, as shown in FIG. 11B.

In one embodiment of treating a saccular aneurysm, various expanded ballstent shapes are acceptable as required to treat saccular aneurysms of various shapes, including circular, oblong, and irregular, so long as the shape is generally rounded and the expanded ballstent including a single lobe. Regardless of the formed shape, when a ballstent is expanded in the lumen or cavity 701 of an aneurysm sac 700, in one embodiment, the ballstent is designed to conform, at least partially, to the shape of the cavity.

Research suggests that the presence of an intact endothelium correlates with expansion of the lumen of blood vessels and aneurysms in certain clinical situations. In these settings, endothelial cells sense changes in the lumen of blood vessels or aneurysms and stimulate biological processes that lead to an increase in cellular and enzyme activity in the wall of blood vessel segments or aneurysms associated with changes in the extracellular and cellular components of the wall and expansion or enlargement of the lumen. Research has also shown that endothelial cells require flowing blood on their luminal surface to remain healthy and viable. Therefore, a medical device, system, or method that could reduce or eliminate flowing blood over the luminal surface of endothelial cells lining an aneurysm or blood vessel segment could thereby reduce endothelial cell viability, biochemical signaling from endothelial cells, and increases in cellular and enzymatic activity associated with blood vessel or aneurysm expansion or enlargement, which is an important goal in preventing or treating aneurysms. Given this, in certain embodiments, the ballstent 100 is fully expanded to treat a saccular aneurysm. In addition to the physical nature of the filling and blocking effect of the expanded ballstent in the aneurysm sac, this treatment also reduces endothelial viability in the aneurysm sac. In other embodiments, the ballstent 100 need not be fully expanded to treat a saccular aneurysm, but may successfully seal the aneurysm or reduce endothelial cell viability while partially expanded. In all embodiments, the ballstent remains in an expanded state (partially or completely) after detachment from the delivery catheter. An expanded state refers to the at least partial distention of the ballstent 100, such as at least 20%, 50%, 75%, or 90% and up to 100% of the maximum ballstent volume.

In various embodiments, the blockstent 150 need not be fully expanded to occlude a blood vessel segment. For example, the blockstent 150 may be partially expanded, or may be completely expanded. In all embodiments, the blockstent remains in an expanded state (partially or completely) after detachment from the delivery catheter. An expanded state refers to the at least partial distention of the blockstent 150, such as at least 10%, 20%, 50%, 75%, or 90% and up to 100% of the maximum blockstent volume.

Forming the Expandable Body

In an exemplary method of forming the expandable body 100 or 150, the central layer 122 of the wall 102 of the ballstent 100 or the blockstent 150 may be formed by vapor deposition, wherein vapors from one or more polymers, pure metals, or metal alloys are condensed upon a substrate or mold (e.g., mandrel). The mold may be removed to provide a hollow shell formed of the pure metal or metal alloy.

Figures 32A, 32B, 32C, 33, 34, 35:
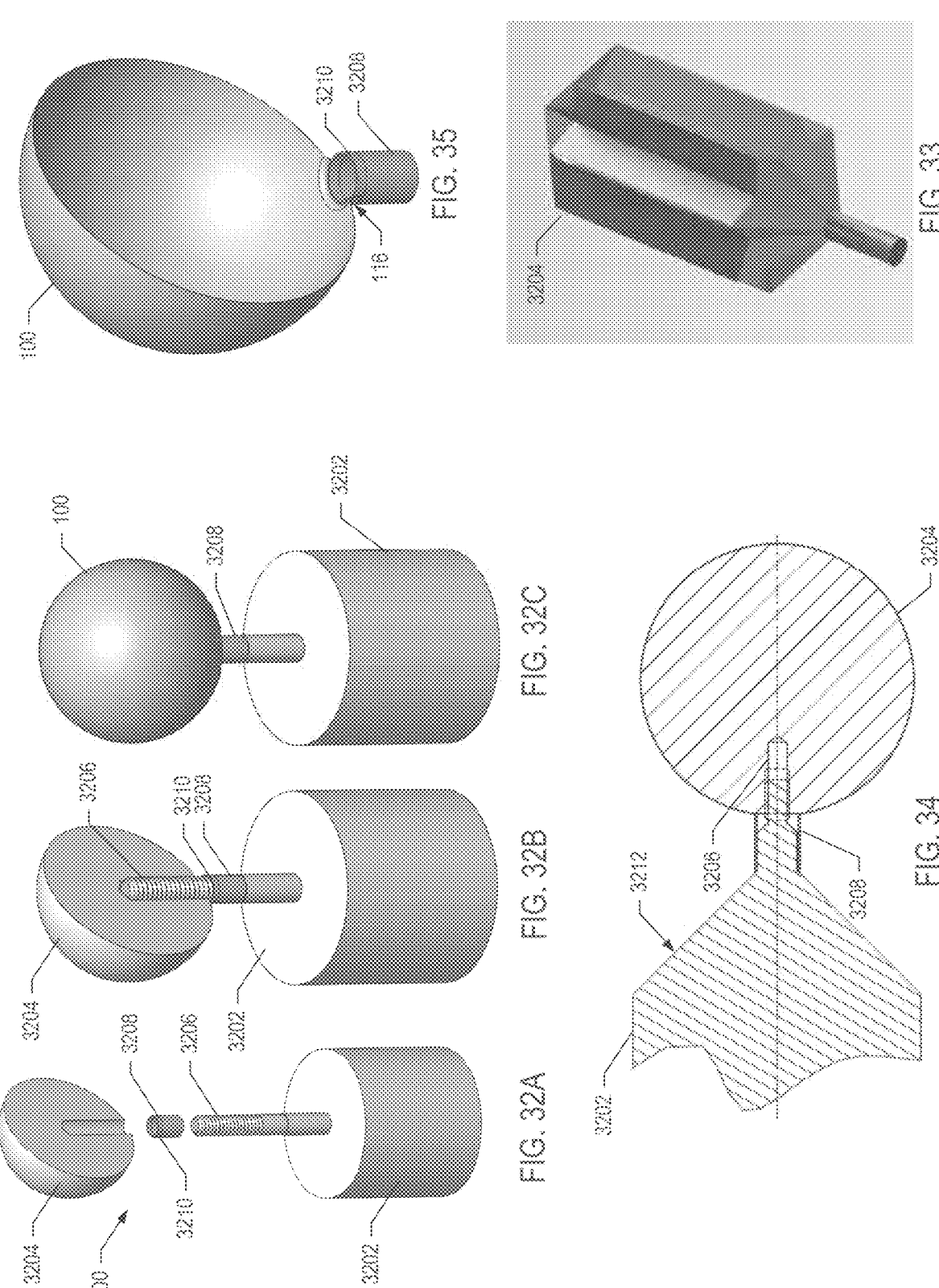
FIGS. 32A-C depict a sequence for electroforming an expandable body on a mandrel.
FIG. 33 depicts an embodiment of a mandrel for electroforming a metal expandable body.
FIG. 34 depicts another embodiment of a mandrel for electroforming a metal expandable body.
FIG. 35 is a partial cross-section of metal expandable body produced by electroforming.

In a preferred embodiment, the central layer 122 of the wall 102 is formed by electroforming or electroplating a metallic shell over a removable form or mold (e.g., mandrel). For example, as shown in FIGS. 32A-C, a multi-part mandrel 3200 for electroforming the expandable body 100 or 150 is shown in partial cross-section. The mandrel 3200 includes a steel base 3202 and form member 3204 that is removable from the base. Preferably, the form member 3204 is composed of a rigid material, including but not limited to aluminum or stainless steel. Although shown as a sphere, other embodiments of the form member 3204 may be other shapes, including but not limited to the shape of a partially pleated or partially folded body 3204 that results in an expandable body 100 or 150 having a configuration intermediate to the deliverable (i.e., fully collapsed or pleated and folded) configuration and the fully expanded configuration, such a partially pleated mandrel 3204 being depicted in FIG. 33. In addition, the protrusions, as shown in FIGS. 12F-I, may be fashioned onto the form member 3204, such that the protrusions are formed during the electroforming or electroplating process. The form member 3204 may be spherical as shown in FIGS. 32A-B and 34 to generate a spherical expandable body 100 or 150. The form member 3204 may be a cylindrical body having hemispherical ends to generate similarly shaped expandable bodies 100. In various embodiments, the mandrel 3200 or at least the removable form 3204 is sacrificial, such that it is consumed during the process of forming the expandable body 100 or 150.

To form a metal expandable body, the form member 3204 is removed from the base 3202. A portion of the form member 3204 may be threaded so that it can engage a threaded spindle 3206 extending from the base 3202. After the form member 3204 is detached from the base 3202, a metallic ring 3208 is positioned on the threaded spindle 3206. In one embodiment shown in FIG. 34, the threaded spindle 3206 includes a shoulder 3212 that has a diameter greater than that of the threaded spindle 3206, such that the metallic ring 3208 can be seated in a desired position.

The metallic ring 3208 is a non-sacrificial component of the mandrel 3200. In one embodiment, the metallic ring 3208 is any biocompatible metal that is reactive to electrolysis. For example, the metallic ring 3208 may be composed of gold, 316L stainless steel, or 304 stainless steel. Preferably, the metallic ring is composed of 304 stainless steel, as 304 stainless steel has a lower nickel content than 316L stainless steel and will minimize the risk of cytotoxicity during electrolysis. In some embodiments, 304 stainless steel is preferred as it has a pitting potential (approximately 0.18 V-0.38 V) that is lower than the hydrolysis potential of water (approximately 0.82 V). Therefore, electrolysis with 304 stainless steel may be performed under more controlled conditions with more repeatable results than electrolysis performed with 316L stainless steel or gold, whose pitting potentials (approximately 0.98 V-1.18 V and approximately 0.7 V-0.9 V, respectively) exceed the hydrolysis potential of water.

In various embodiments, the metallic ring 3208 is between approximately 0.025 inches and approximately 0.150 inches in length, with a wall that is between approximately 25.4 μm and approximately 254.0 μm thick. In one embodiment, the metallic ring 3208 is 0.05 inches in length. A gold plating or coating may optionally be applied to at least a portion 3210 of the metallic ring 3208 to encourage the deposition of gold that will be used to form a gold expandable body. Similarly, a plating or coating composed of another metal, including but not limited to platinum, may be used to encourage the deposit of the other metal. As such, the metallic ring 3208 will be integrated into the expandable body 100 or 150 and form a portion of the neck 116 of the expandable body.

Once the metallic ring 3208 and the form member 3204 are positioned on the threaded spindle 3206, the mandrel 3200 is placed in an electrolytic bath (not shown) containing metallic ions, such as gold, where the gold ions are deposited on the form member and at least a portion of the metallic ring 3208. In particular, the mandrel 3200 is positioned such that the expandable body 100 or 150 is electroformed over the form member 3204 and the portion of the metallic ring 3208 having the gold flash, thereby bonding the metallic ring to the expandable body. Preferably, the remaining portion of the metallic ring 3208 is not coated by gold.

In various embodiments and as can be understood from FIGS. 9A-D, the thickness 120 of the ballstent wall 102 can be controlled by varying the electroforming process. For example, by adjusting the duration of the electroforming process walls of greater or lesser thickness may be formed. Similarly, the wall thickness 120 may be varied in certain locations by applying one or more masks to the mandrel 3200. In addition, the location of the mandrel 3200 relative to the anode in the solution bath will also affect the thickness of the wall. For example, an internal feature at the neck of the expandable body 100 or 150 may have a thinner wall than the rounded spherical portion of the expandable body. The expandable body 100 or 150 may be formed intentionally with a thinner, and therefore weaker, neck region that can be severed to separate the expandable body from the neck 116, including a neck that includes the metallic ring 3208. Alternatively or additionally, a stress concentration ring in the form of a line or strip may be defined in the neck or in the proximal portion 208 of the expandable body 100 or 150, more specifically, a ring-shaped region of exposed metal (e.g., stainless steel portion of the ring 3208 or a gold portion of the neck 116) to help facilitate separation of the delivery tool from the expandable body at the ring-shaped region of the exposed metal. Such a stress concentration line may be formed into the ring-shaped region of the exposed metal via laser etching, various mechanical operations such as sawing or grinding, or by electrolysis.

After formation, the expandable body 100 or 150 and the form member 3204 are removed from the mandrel base 3202, where the form member is removed to leave only the metallic ring 3208 and the expandable body, shown in a partial cross-section in FIG. 35. In one embodiment, the aluminum form member 3204 is removed though the neck 116 by chemical and/or thermal leaching. In another embodiment, a hole is drilled into the aluminum form member 3204 though the neck 116 by mechanical operations, such as, but not limited to, drilling with an auger bit. The hole may be used to accelerate and regulate the chemical leaching or etching process to remove the aluminum form member 3204 from the expandable body 100 or 150. Preferably, combinations of mechanical, chemical, and thermal methods are used to ensure that all of the constituents of the form member 3204 are removed. It is desirable to completely remove the form member 3204 from the expandable body 100 or 150 to ensure sufficient plasticity or malleability of the expandable body and to minimize any toxic effects after implantation, such as may be the case specifically when the expandable body comprises residual aluminum.

To reduce the presence of stress concentrations regions or surface variations of the expandable body 100 or 150 and to eliminate the transfer of concentric machine marks from the form member 3204, the mandrel 3200 and in particular the form member may be polished or lapped before electroforming the expandable body. An unpolished form member 3204 and a resulting gold expandable body 100 or 150 are shown in FIGS. 36A and 36B, respectively. Conversely, a polished form member 3204 having a lapped finish and the resulting gold expandable body 100 or 150 are shown in FIGS. 36C and 36D, respectively. In one embodiment, polishing the form member 3204 reduces the distance between the highest and lowest points of surface imperfections or features to approximately 0.1 µm or less.

Once the form member 3204 has been removed from the expandable body 100 or 150, the expandable body may undergo an annealing process to improve the pliability of the expandable body. In one embodiment, the expandable body is heated to approximately 300° C. for approximately 1 hour and then immediately quenched in a bath of distilled water at room temperature. In other embodiments, the expandable body 100 or 150 is folded or otherwise deformed after a first annealing process and then subjected to one or more additional annealing processes. In further embodiments, the expandable body 100 or 150 is folded or otherwise deformed and then subjected to one or more annealing processes.

The interior and exterior surfaces of the expandable body 100 or 150 may be cleaned to remove any contaminants remaining from manufacture. For example, in one embodiment, the expandable body 100 or 150 is placed in an ultrasonic cleaner that contains an isopropyl alcohol bath for approximately 10 minutes. The expandable body 100 or 150 is then removed from the bath and injected with distilled water to remove any contaminants remaining in the interior of the expandable body. Optionally, the expandable body 100 or 150 may be dried in a vacuum oven held at approximately 90° C.

As shown in FIGS. 37A and 37B, the exterior surface 110 of the ballstent 100, the interior surface 106, or both are coated with a polymer such as Parylene™ or an acrylic polymer. The polymer can be added by incorporating a pre-formed material into the desired orientation, by vapor deposition, or other methods. In some embodiments, at least a portion of the neck 116 or the interior surface 3304 of the metallic ring 3208 is not coated. In one embodiment, the ballstent 100 may be annealed, as previously described, at least once after the application of the non-metallic coating. FIGS. 37C and 37D show a similarly coated blockstent 150.

In embodiments of the expandable body 100 or 150 where the wall 102 is composed of a material that his highly non-reactive during electrolysis, such as platinum, the interior and exterior of the neck 116 may be coated, while the remaining surfaces are not coated. Similarly, in some embodiments where the expandable body 100 or 150 will be detached by an operation other than electrolysis, only the interior surface 106 may be coated with the non-metallic coating.

In some embodiments, after coating, a portion of the polymer coating is removed from the exterior surface 3300 to expose the metal surface in a strip or ring configuration, as shown in FIGS. 37E-H. In other embodiments the exposed metal surface may be formed by masking this region before coating, and then removing the masking material. Electrolysis can be used to separate the expanded expandable body from the remainder of the neck 3300 and the delivery catheter at the region comprising the exposed metal surface. The width W of the detachment site (i.e. the exposed metal surface in a strip or ring configuration) 3302 may be in a range between about 0.1 mm and about 0.4 mm. The detachment site W may be located anywhere along the length N1 of the neck 116. In some embodiments W may be located in the region of the neck formed by the metallic ring 3208. In one particular embodiment, the exposed strip of the detachment site 3302 has a width W of 0.25 mm+0.03 mm and is located at a length N5 of approximately 0.51 mm+0.03 mm from the end of the neck 116. The metallic strip may be exposed by any suitable method, including but not limited to laser etching or laser ablation. In other embodiments, the metallic strip of the detachment site 3302 may be exposed before or after the folding or compression of the expandable body 100 or 150. By way of example and not limitation, in one embodiment, the exposed metal in the region 3302 is gold, while in other embodiments the exposed metal is stainless steel.

In various embodiments, the wall 102 of the expandable body 100 or 150 is perforated to create a plurality of microperforations 1300, as shown in FIG. 9B. By way of example and not limitation, the microperforations 1300 may be created by laser perforating the wall 102. The microperforations 1300 or pores may range from approximately 1 µm to approximately 500 µm in diameter and may extend completely through the thickness of the wall 1022 from the interior void 108 to the exterior surface 110. Alternatively, a microperforated expandable body 100 or 150 may be formed during the electroforming process, such as with the use of a masking pattern.

After perforating, the expandable body surfaces 110 and 106 may be coated with a polymer that does not completely cover the microperforations 1300, thereby leaving channels between the inner and outer surfaces. Alternately, the expandable body 100 or 150 may be laser perforated after coating. The microperforations 1300 permit the exchange of fluid between the interior void 108 of the expandable body 100 or 150 and the environment exterior to the expandable body.

In various embodiments, the exterior layer 104 may be formed on the outside of the central layer 122 of the expandable body 100 or 150 by additional electroplating or electroforming, by vapor deposition, or by sputter deposition, wherein material is eroded from a target (e.g., a metal or metal alloy) and is then deposited onto a substrate (e.g., a mandrel or mold) forming a thin layer on the substrate. Similarly, an interior layer 214 may be formed on the inside of the central layer 122 of the expandable body 100 or 150 by additional electroplating or electroforming, or by vapor deposition, or by sputter deposition.

In various embodiments, an additional polymer coating is applied to the expandable body 100 or 150 to tune the strength and flexibility characteristics of the wall 102. For example, the additional reinforcement polymer may be applied via dip, spin, or spray coating, or through deposition processes specialized for the specific polymer. The additional coating may be Parylene, biocompatible polyurethanes, PTFE, and silicone, among others. In one embodiment, this coating can be limited to the neck 116 of the expandable body 100 or 150 by using a mechanical or chemical template. In various embodiments, detailed geometries and designs can be laser etched into the reinforcement coating to further optimize the wall properties with the folding geometry. Further, the removal of the reinforcement coating in regions where it in not needed would also remove unnecessary material from the final diameter of the collapsed and wrapped expandable body 100 or 150.

The wall 102 of the main body of the expandable body 100 or 150 may be formed by different methods than the neck 116. The central layer 122 of the expandable body 100 or 150 may be formed by different methods than the exterior layer or coating 104 or the interior layer or coating 214. In various other embodiments, the expandable body 100 or 150 may be formed by manipulating and securing one or more sheets of metal in the desired configuration to form the wall 102 and/or the exterior layer 104. These two-dimensional sheets may further comprise rubber, plastic, polymer, woven or knitted fiber materials, or other materials, or combinations thereof. By way of example and not limitation, one or more two-dimensional sheets of a metal may be folded into an expandable body shape and welded, soldered, glued, or bonded together. Similarly, two-dimensional sheets of material may be manipulated and secured to form the exterior layer 104 or the interior layer 214.

The Delivery Device

The expandable body 100 or 150 is advanced and positioned within human body by an elongated portion of the medical device known as the "delivery device" or "delivery catheter". In one embodiment, a delivery device is an elongated surgical instrument that defines at least one lumen, or potential lumen. The delivery device has a proximal and a distal end and is dimensioned to deliver a fluid medium from a fluid medium source at the proximal end of the device into the central void or space 108 of the expandable body 100 or 150, which is attached to the distal end of the delivery device. Further, any medical device or component of a medical device that can position the expandable body 100 or 150 at a desired location in the vascular system, such as the lumen of a saccular aneurysm or lumen of a target blood vessel, facilitate the expansion of the expandable body, and then facilitate the separation of the expandable body from the delivery device is generally acceptable as a delivery device. Typically, the delivery device is a catheter (a "delivery catheter"). Preferably, the delivery catheter may be any flexible catheter, hollow wire, removable core wire, or combinations thereof, suitable for accessing locations with the vascular system including the delivery catheters 300 and 400, shown in FIGS. 2 and 6. The delivery device may also be any other type of catheter, hollow wire, or removable core wire, or alternatively a needle or trochar, a stylet, or combinations thereof, suitable for accessing locations within the vascular system or in other biological conduits. In various embodiments, the delivery device is a catheter 300 or 400 that can carry an attached compressed expandable body 100 or 150 to the lumen of a saccular aneurysm or the lumen of a target blood vessel. Preferably, the delivery device or delivery catheter extends only into the neck of the expandable body 100 or 150, such that no portion or component of the delivery device, including but not limited to a guidewire or an obturator, extends into the interior void 108 of the expandable body.

Figures 2, 3A:
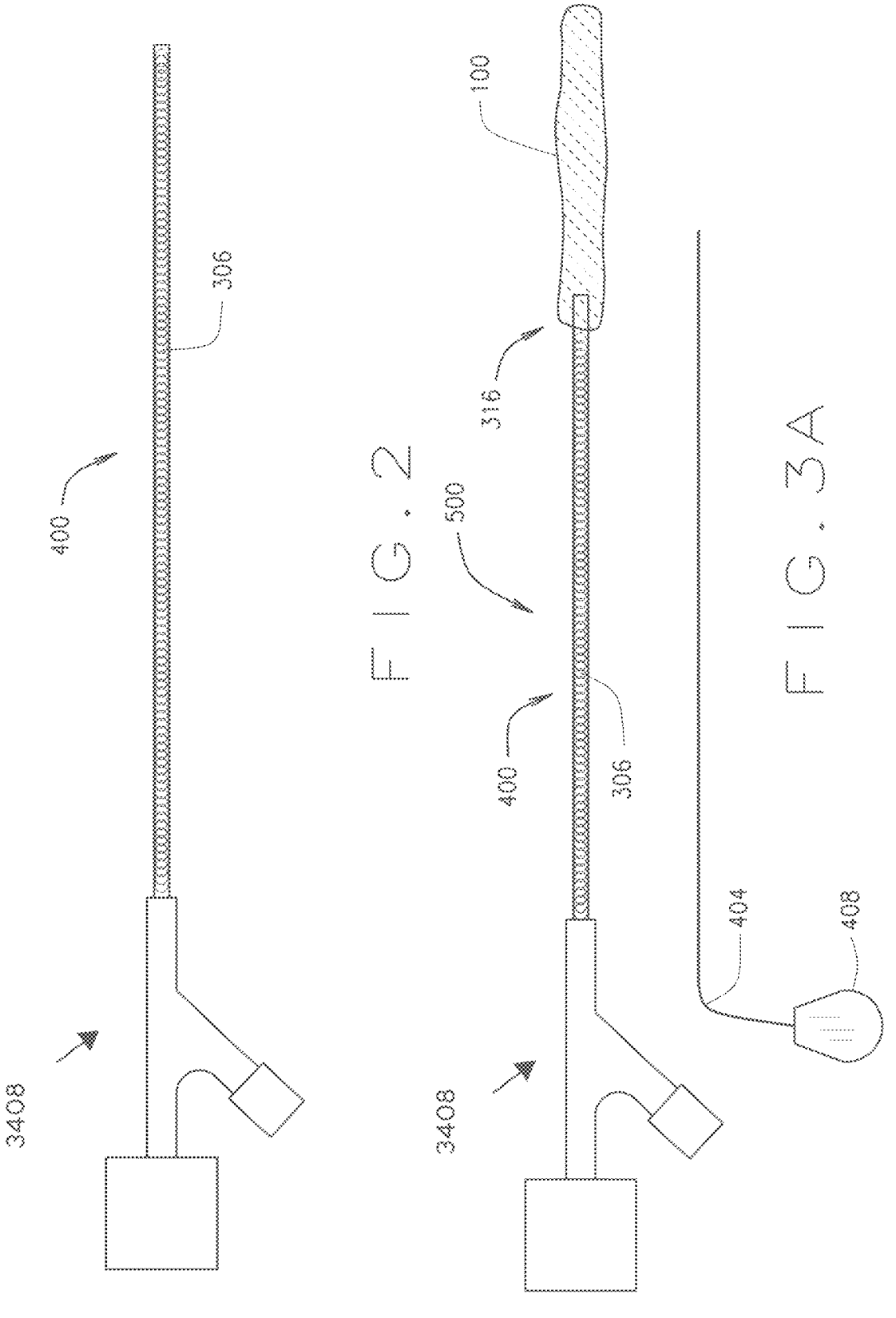
FIG. 2 is a plan view of an embodiment of the delivery catheter of the medical device.
FIGS. 3A-C are plan views of an embodiment of the medical device.
Figures 6, 7A:
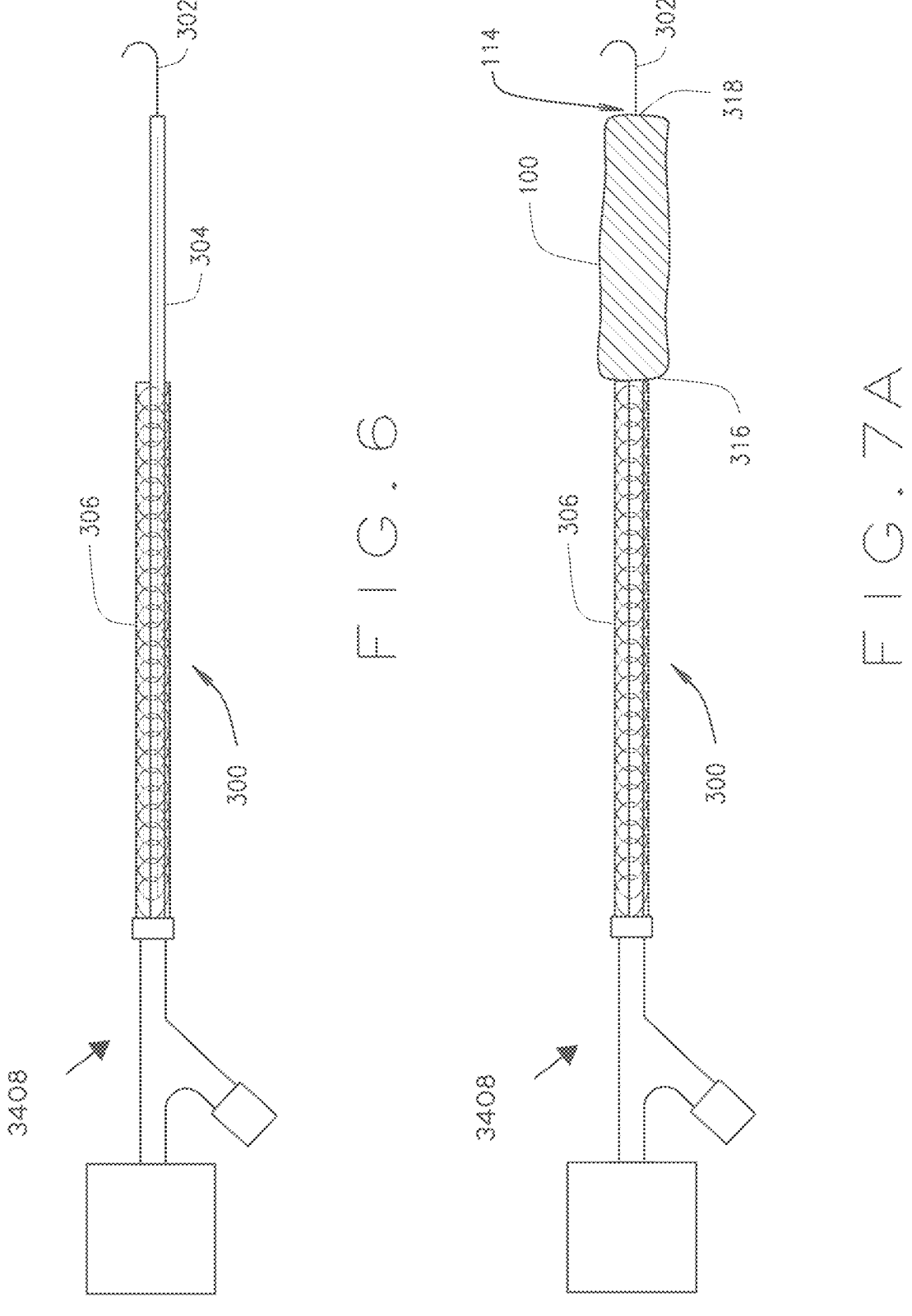
FIG. 6 is a plan view of an embodiment of the delivery catheter of the medical device.
FIGS. 7A-C are plan views of an embodiment of the medical device.

A catheter is a flexible, tubular, elongate medical device configured for insertion into bodily compartments, including blood vessels, to permit the injection or the withdrawal of fluids, amongst other functions. Catheters are often formed of polymers or plastics and optionally further include metal, such as in a coil or braid configuration for reinforcement. Catheters can be configured to enable attachment to expandable bodies 100 or 150, facilitate the delivery of compressed expandable bodies to the lumen of an aneurysm sac or lumen of a target blood vessel or other biological conduit, facilitate the expansion of compressed expandable bodies, and separate from expanded expandable bodies. In some embodiments, the delivery catheter 300 or 400 can be configured to pass through the vascular system with the attached expandable body 100 or 150 in a compressed form, as shown in FIGS. 3A and 7A. After expansion, the expandable body 100 or 150 is separated from the delivery catheter 300, thereby allowing the expanded expandable body to remain in place while the delivery catheter is removed from the body. In this way, delivery catheters are similar to angioplasty balloon catheters, which are configured to enable attachment to traditional tubular stents, to facilitate the delivery of attached compressed traditional tubular stents to the lumen of a specific segment of a blood vessel or other biological conduit, enable expansion of compressed traditional tubular stents, and separate from expanded traditional tubular stents.

The delivery catheter 300 and 400 is composed of a biocompatible material. By way of example and not limitation, the delivery catheter 300 and 400 and various components thereof may be formed of silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations thereof. In one embodiment, the wall of the delivery catheter 300 and 400 may be reinforced with a metal, such as coiled or braided stainless steel or nitinol, to enhance control and reduce kinking of the delivery catheter 300 and 400 during use. Metals suitable for delivery catheter reinforcement include stainless steel and nitinol.

As shown in FIG. 2, 3A-B, 6, 7A-B and 16A-B, the delivery catheter 300 and 400 will have a hollow, or potentially hollow, cylindrical member that defines a lumen to allow for passage of a fluid medium from the proximal end of the delivery catheter to the distal end of the delivery catheter and into the central void 108 of the expandable body. The delivery catheter 300 or 400 is designed and dimensioned such that it can be inserted in the body to deliver the compressed expandable body 100 or 150 to a desired location, facilitate the expansion of the expandable body, and facilitate the separation of the expanded expandable body from the delivery catheter. When a single lumen delivery catheter 400 is used, the compressed expandable body may be positioned in the lumen of a saccular aneurysm or lumen of the target blood vessel after being advanced through a separate larger guide catheter that is positioned with its distal end within or near the aneurysm or target location within the target blood vessel. Once in the lumen of the aneurysm sac or lumen of the target blood vessel and out of the guide catheter, the compressed expandable body 100 or 150 can be expanded, and then the expanded expandable body and the delivery catheter can be separated, and the delivery catheter and the guide catheter can be removed from the body, while the expanded expandable body remains in place. The hollow, or potentially hollow, cylindrical member 306 of delivery catheter 400 has a wall thickness ranging from about 0.05 mm to about 0.25 mm. Preferably, wall thickness of the hollow cylindrical member 306 ranges from about 0.1 mm to about 0.2 mm. The lumen 312 defined by the hollow cylindrical member 306 for the purpose of enabling the passage of a fluid medium into the central void or space of the expandable body 108 has a diameter ranging from about 0.4 mm to about 1.0 mm. The proximal end of the hollow cylindrical member 306 includes a port or hub 3408 to communicate with a pressurized fluid medium source, such as a syringe 314 or a pump (not shown) containing, for example, water, saline or a radiographic contrast solution. The fluid media for expanding the expandable body are received into the delivery catheter 300 or 400 through the hub or port 3408.

Single Lumen Catheters

Figures 16A, 16B, 17A, 17B:
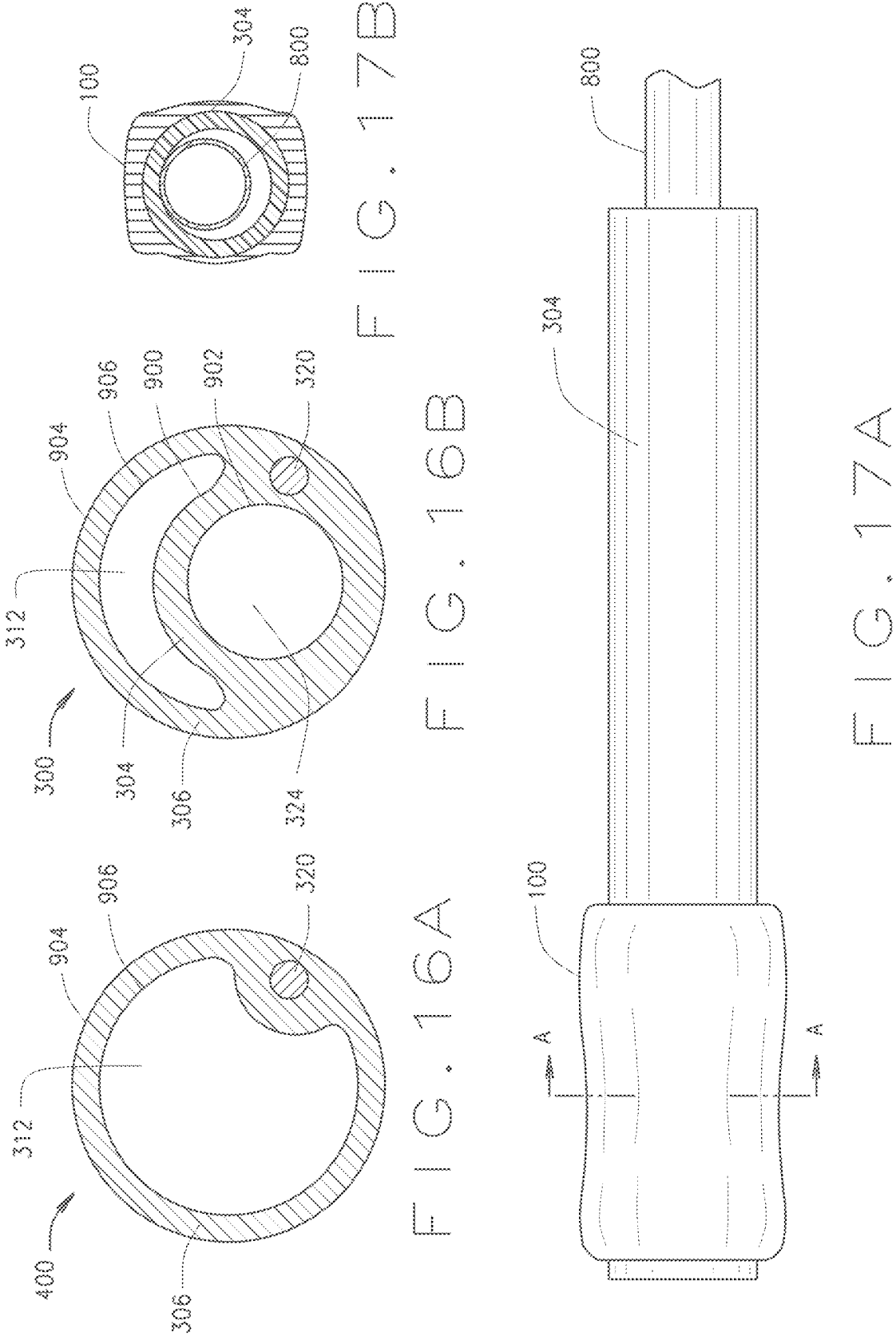
FIGS. 16A-B are transverse cross-sections of embodiments of the delivery catheter of the medical device.
FIG. 17A is a plan view of an embodiment of the medical device with a lumen configured to accept a guide catheter, rather than a guide wire.
FIG. 17B is a transverse cross section of the device as taken along section line A-A in FIG. 17A.
Figure 18:
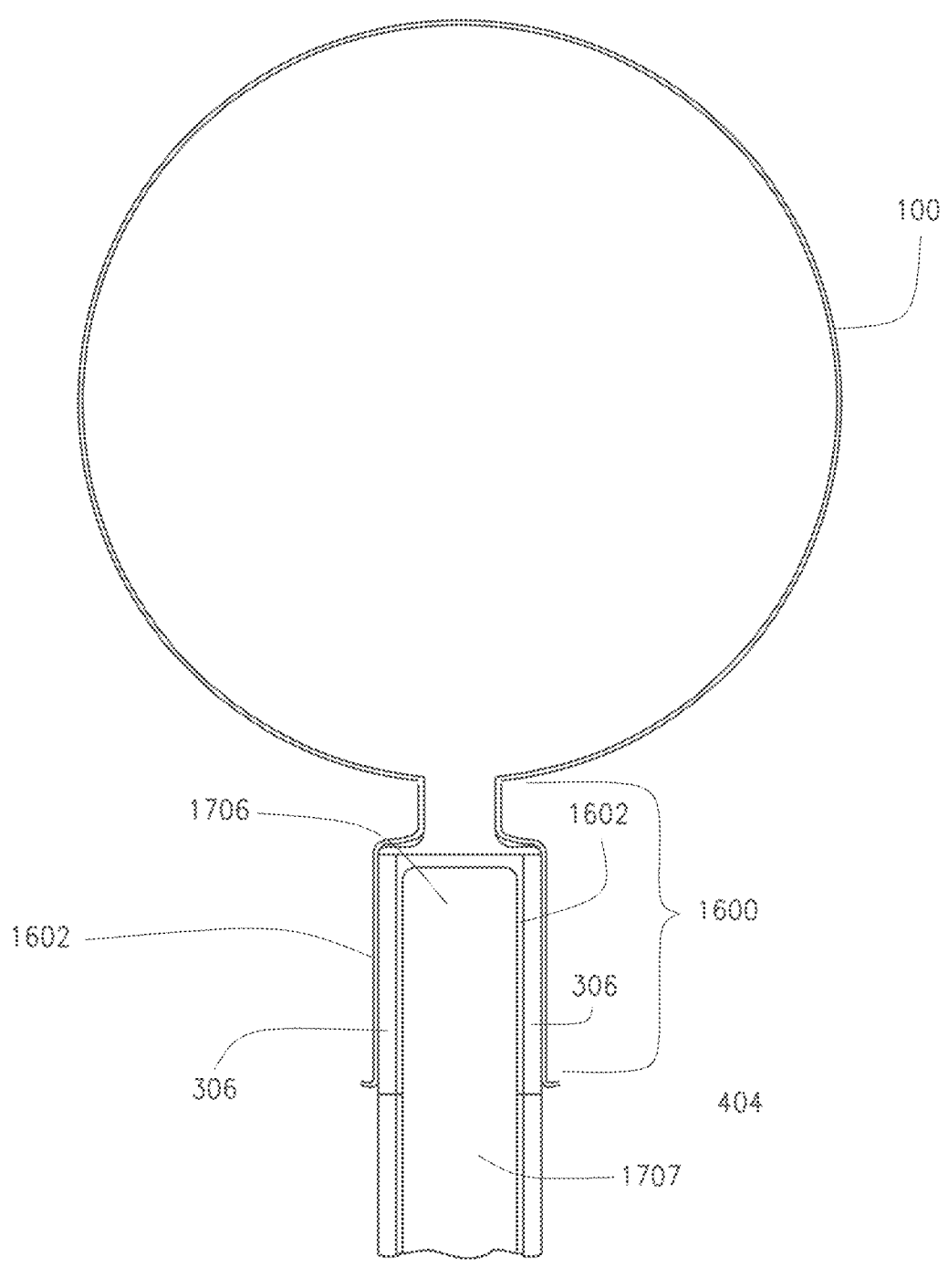
FIG. 18 depicts a hemispherical cross-sectional view taken along a diameter of an embodiment of the expandable body and a portion of the delivery catheter.

FIG. 2 depicts a longitudinal view of a single lumen embodiment of the delivery catheter portion 400 of the medical device 500, and FIG. 16A depicts a transverse cross-section of the single lumen catheter. As shown in FIGS. 4A-E, for the single lumen embodiment, the delivery catheter 300 moves through the lumen of a guide catheter 800 to deliver the compressed ballstent 100 to the lumen 701 of a saccular aneurysm 700. For this single lumen embodiment, the delivery catheter 400 does not include a hollow cylindrical member that defines a lumen that is dimensioned to allow for the passage of a guidance member, or guide wire.

The dimensions of the delivery catheter 300 or 400 are a matter of design choice depending upon the size of aneurysm to be treated and the location of the aneurysm in the vascular system. The distance between the aneurysm to be treated and the site of insertion of the medical device into the vascular system, will determine, in part, the length of the delivery catheter 300 or 400. Delivery catheter lengths range between about 5 cm and about 300 cm, with preferable ranges between about 75 cm and about 225 cm. The smallest diameter blood vessel segment in the path between the site of insertion of the medical device into the vascular system and the aneurysm to be treated will determine, in part, the diameter of the delivery catheter. Delivery catheter diameters range between 2 Fr and 7 Fr, with preferable ranges between 2 Fr and 5 Fr. Similarly, when occluding a blood vessel as illustrated in FIGS. 4F-J, the smallest diameter blood vessel segment in the path between the site of insertion of the medical device into the vascular system and the blood vessel to be treated, will determine, in part, the diameter of the delivery catheter. As such, delivery catheter diameters for delivering a blockstent 150 range between 2 Fr and 12 Fr, with preferable ranges between 2 Fr and 5 Fr.

Figures 3B, 3C:
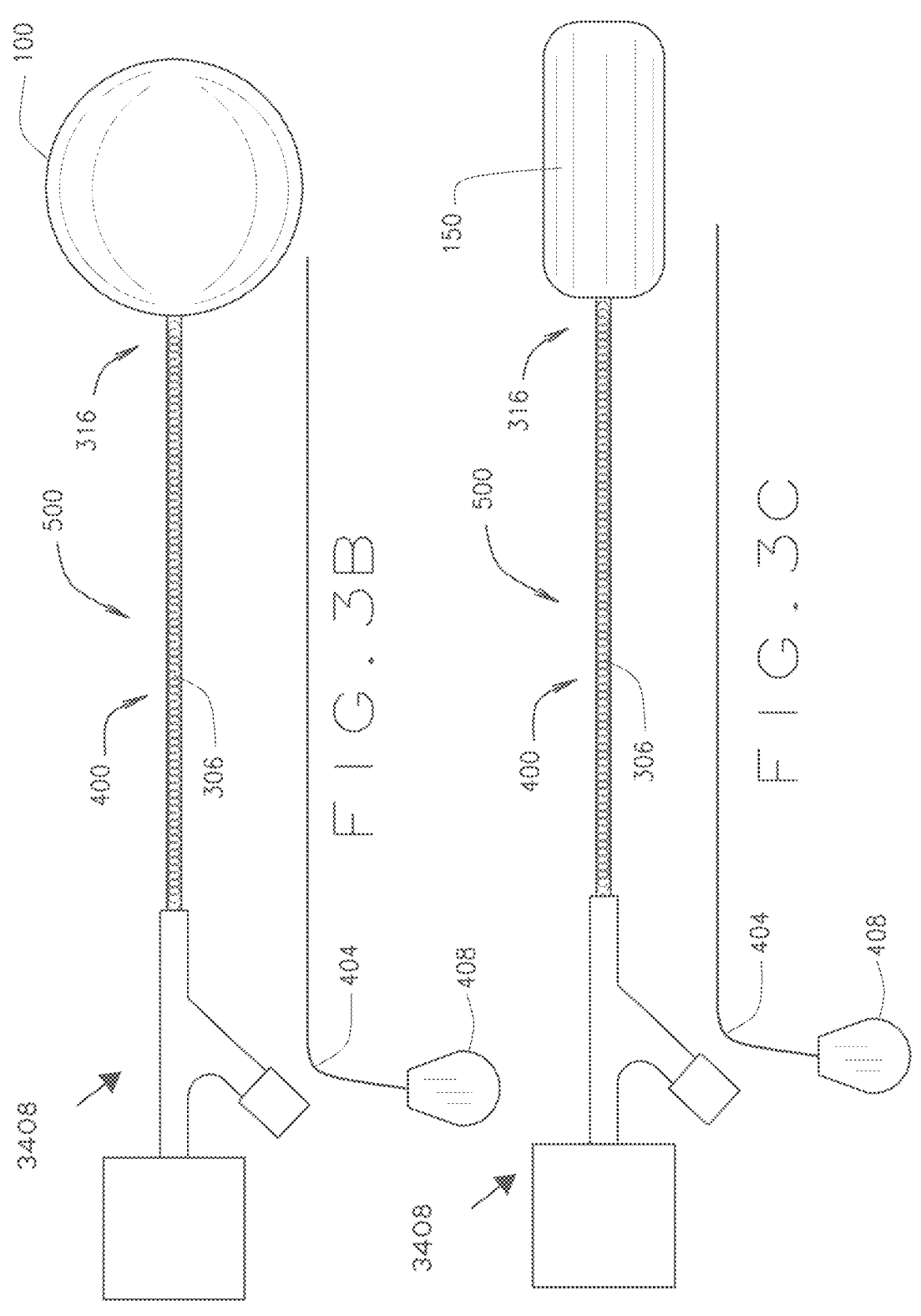

FIGS. 3A-C depict longitudinal views of a single lumen embodiment of the delivery catheter portion of a medical device 500. FIG. 3A depicts a longitudinal view of a single lumen embodiment of the medical device 500 with the ballstent 100 in a compressed form. FIG. 3B depicts a longitudinal view of a single lumen embodiment of the medical device 500 with the ballstent 100 in an expanded form, while FIG. 3C depicts the medical device with the blockstent 150 in an expanded form.

Figure 28:
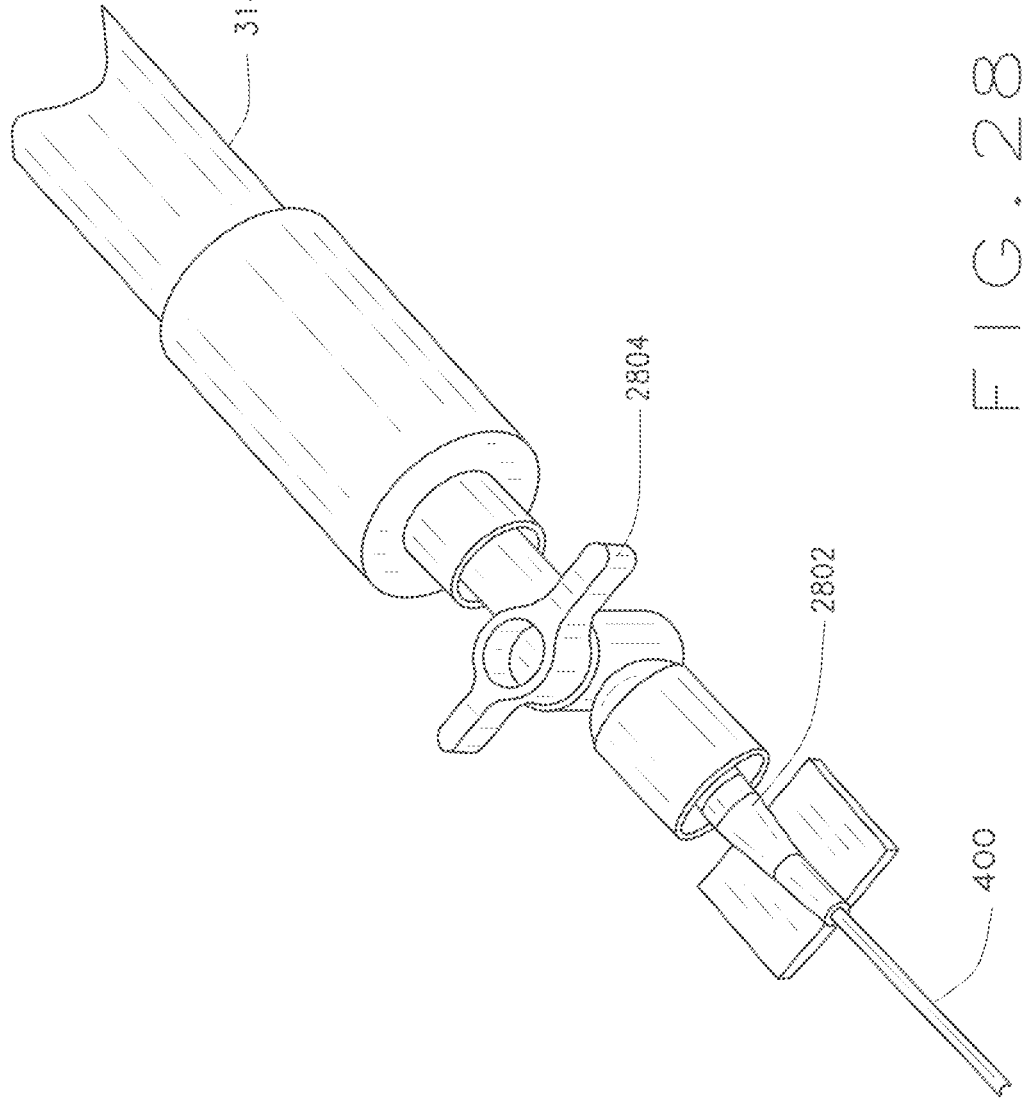
FIG. 28 is a perspective view of an arrangement for inflating or deflating an expandable body.

In some embodiments, the proximal end of the delivery catheter 400 is configured with a hub 3408 that may facilitate a Luer-Lok™ or Luer-Slip™ type connection for connecting a fluid medium source, such as a syringe 314, to the lumen 312 of a hollow cylindrical member configured to transmit the fluid medium from the proximal end of the delivery catheter to the central void or space of the expandable body 100 or 150. As shown, in FIG. 28, the lumen 312 of a delivery catheter 400 is connected to a fluid medium source, such as the syringe 314, through a female Luer fitting 2802. A stopcock 2804 or flow switch may be positioned between the fluid medium source and the delivery catheter 400 to enable greater control over the movement of the fluid medium into and out of the delivery catheter.

As shown in FIGS. 3A-B and 4A-E, in one embodiment of the medical device 500, the delivery catheter 400 advances the attached compressed ballstent 100 through the lumen of a larger guide catheter 800, beyond the distal end of the guide catheter, and into the lumen 701 of the aneurysm sac 700. Once the compressed ballstent 100 has been placed in the lumen 701 of the aneurysm sac 700, a removable wire or obturator 404 is removed from the delivery catheter. The removable wire or obturator 404 may include a handle 408 or other device to facilitate insertion and removal. Then, a fluid medium source, such as the syringe 314 can be connected to the hub 3408 and a fluid medium can be moved from the syringe 314 into the central void or space 108 of the ballstent 100, resulting in expansion of the ballstent within the lumen 701 of the aneurysm sac 700 and filling at least a portion of the aneurysm sac. Fluid media such as water, saline, solutions of radiographic contrast agents, or solutions of drugs, such as thrombin, can be used to expand the compressed ballstent 100. As shown in FIG. 4E, after the ballstent 100 is expanded, the delivery catheter 400 and the ballstent 100 are separated and the delivery catheter and guide catheter 800 are removed while leaving the expanded ballstent in the lumen 701 of the aneurysm sac 700. A variety of methods and devices can be used to separate the delivery catheter from the ballstent 100. In one embodiment as indicated in FIGS. 2, 3A and 3B, the delivery catheter 400 comprises an electrolysis wire 320 or the insulated conductor wire. For this embodiment, after the ballstent 100 is expanded, a DC current is applied to the electrolysis wire 320 or the insulated conductor wire to dissolve a portion of the weld or solder 316 between the ballstent 100 and the delivery catheter 400, or alternatively to dissolve a portion of the ballstent 100 by electrolysis. Once the weld or solder 316 is dissolved or corroded, or alternatively a portion of the ballstent 100 is dissolved or corroded, the delivery catheter 400 is separated from the ballstent and the delivery catheter and the guide catheter 800 are removed.

A similar method may be used to occlude a blood vessel with a blockstent 150. As shown in FIGS. 3A, 3C, and 4F-J, in one embodiment of the medical device 500, the delivery catheter 400 advances the attached compressed blockstent 150 through the lumen of a larger guide catheter 800, beyond the distal end of the guide catheter, and into the lumen 721 of the target blood vessel segment 720. Once the compressed blockstent 150 has been placed in the lumen 721 of the target blood vessel segment 720, the removable wire or obturator 404 is removed from the delivery catheter. The removable wire or obturator 404 may include a handle 408 or other device to facilitate insertion and removal. Then, a fluid source, such as the syringe 314 can be connected to the hub 3408 and fluid can be moved from the syringe 314 into the central void or space 108 of the blockstent 150, resulting in expansion of the blockstent within the lumen 721 of the blood vessel segment 720 and filling of the blood vessel. As shown in FIG. 4J, after the blockstent 150 is expanded, the delivery catheter 400 and the blockstent 150 are separated and the delivery catheter and guide catheter 800 are removed while leaving the expanded blockstent in the lumen 721 of the blood vessel segment 720. A variety of methods and devices can be used to separate the catheter from the blockstent 150. In one embodiment as indicated in FIGS. 2, 3A and 3C, the delivery catheter 400 comprises an electrolysis wire 320 or an insulated conductor wire. For this embodiment, after the blockstent 150 is expanded, a DC current is applied to the electrolysis wire 320 or the insulated conductor wire to dissolve a portion of the weld or solder 316 between the blockstent 150 and the delivery catheter 400 or alternatively to dissolve a portion of the blockstent 150. Once the weld or solder 316 is dissolved, or alternatively a portion of the blockstent 150 is dissolved, the delivery catheter 400 is separated from the blockstent and the delivery catheter and the guide catheter 800 are removed.

Single Lumen Catheters

Figures 29B, 29C, 29D, 29E, 29F:
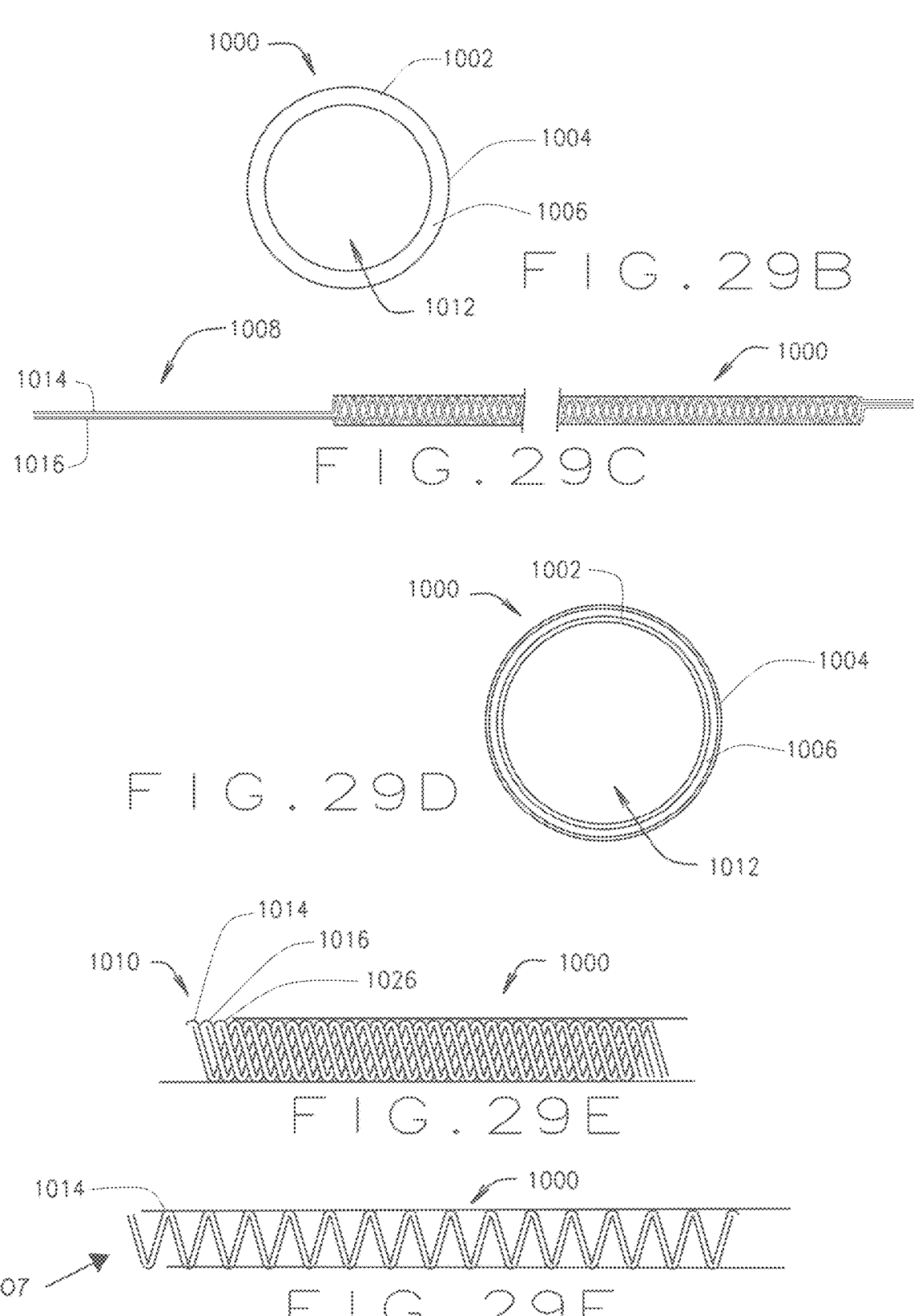
FIGS. 29B-F are transverse cross-sectional and plan views of various delivery catheters.

In various embodiment as illustrated in FIGS. 29B-C, a single lumen catheter 1000 has a coil-reinforced wall 1002 consisting of one, two, or three electrical conductor (e.g., wires, cables or etc.) to provide conductive path(s) for performing electrolysis, as explained more fully below. In one embodiment, the external surface 1004 of the wall 1002 is composed of polyimide and has a hydrophilic or lubricious coating, while the conductive path(s) includes 0.001 inch×0.003 inch flat 304V stainless steel coils 1006. The conductor coils 1006 can be configured in a one, two, or three conductor arrangement 1008 as shown in FIGS. 29B-C and FIGS. 29D-F, as discussed below with regard to performing electrolysis. The conductors of the coil 1006 and any other conductors may be straight, braided, or coiled. The conductive path defined by the conductor coils 1006 can be coated in an insulating polymer such as Parylene™, while the interior lumen 1012 can be lined with a PTFE composite.

In certain embodiments, a modified infusion wire having a removable core can be used as a single lumen delivery catheter. An infusion wire is a modified guide wire wherein the solid metal core can be removed to leave a lumen that can be used to inject the fluid media. An infusion wire with a removable core can be modified such that an expandable body 100 or 150 can be attached to the distal end and expanded through the wire lumen, after the removal of the core wire.

In some embodiments all or a portion of the interior and exterior surfaces of the delivery device can be further coated with a hydrophilic or lubricious coating. In other embodiments, all or a portion of the expandable body 100 or 150 can also be coated with a hydrophilic or lubricious coating.

Dual Lumen Catheters

As shown in FIG. 6 and FIG. 16B, the delivery catheter 300 may include an additional hollow cylindrical member that defines a second lumen 324 to receive a guidance member, such as a guide wire 302, to assist in the guidance of the ballstent 100 component of the medical device to the desired location, as can be understood from FIGS. 7A-B and 8A-E. This second lumen 324 is generally adjacent and parallel to the first lumen 312. As shown in FIG. 6 and FIG. 16B the delivery catheter may be a double lumen catheter, with one lumen 312 configured to enable the passage of the fluid medium from a fluid medium source at the proximal end of the delivery catheter to the central void or space 108 of the ballstent at the distal end of the delivery catheter, and the other lumen 324 configured to accept a guidance member, such as a guide wire 302, to facilitate advancement and positioning of the medical device in the vascular system. As shown in FIG. 16B, the delivery catheter 300 includes two hollow cylindrical members, each with a lumen, wherein the hollow cylindrical members 304 or 306 have a wall thickness ranging from about 0.05 mm to about 0.25 mm. Preferably, the hollow cylindrical member 304 or 306 wall thickness ranges from about 0.1 mm to about 0.2 mm. The lumen defined by the hollow cylindrical member 304 for the accepting a guide wire 302 has a diameter ranging from about 0.25 mm to about 0.5 mm. The diameter of the lumen for the passage of the fluid medium into the ballstent 100 and the diameter of the lumen for accepting a guidance member 324 may be similarly dimensioned. Alternatively, the diameter of the lumen for the passage of the fluid medium into the ballstent may be larger or smaller than the diameter of the lumen for accepting a guidance member, such as the guide wire 302.

For a delivery catheter with two lumens, the first and second hollow cylindrical members may be similarly dimensioned. Alternatively, the second hollow cylindrical member may have a larger diameter to accept the guidance member, or a smaller diameter. The proximal end of the second hollow cylindrical member 304 is engaged to the hub 3408. The hub 3408 facilitates the insertion of the guide wire 302 into the second hollow cylindrical member 304. As can be understood from FIGS. 6, 7A-B, 8A-E, and 16B, the guide wire 302 is fed through the second hollow cylindrical member 304 and extended out of the distal end of the delivery catheter 300. In this embodiment, the delivery catheter 300 is advanced over the guide wire 302 until the compressed ballstent 100 is positioned in the lumen of a saccular aneurysm. Once the compressed ballstent 100 is in the desired position, the ballstent 100 is expanded by the fluid medium provided to the first hollow cylindrical member 306 by the syringe 314 connected to the ballstent expansion hub 3408. Fluid media such as water, saline, solutions of radiographic contrast agents, or solutions of drugs, such as thrombin, can be used to expand the compressed ballstent. The guide wire 302 is preferably an angiographic wire of sufficient length for the distal tip of the guide wire to reach the aneurysm, and a proximal end extending out and away from the point of entry into the vascular system. In some embodiments, the guide wire 302 has a straight or angled distal tip, while in other embodiments, the guide wire 302 has a curved J-shaped distal tip, typically constructed from a shape-memory alloy or a braided metal that causes the tip to return to the J-shape after any applied stress is removed. The materials and dimensions of the guide wire 302 may be selected based upon the diameter, length, and tortuosity of the blood vessels being traversed. Typically, the guide wire 302 may be composed of any suitable biocompatible materials and have an outer diameter ranging between about 0.3 mm to about 0.95 mm.

Figures 7B, 7C:
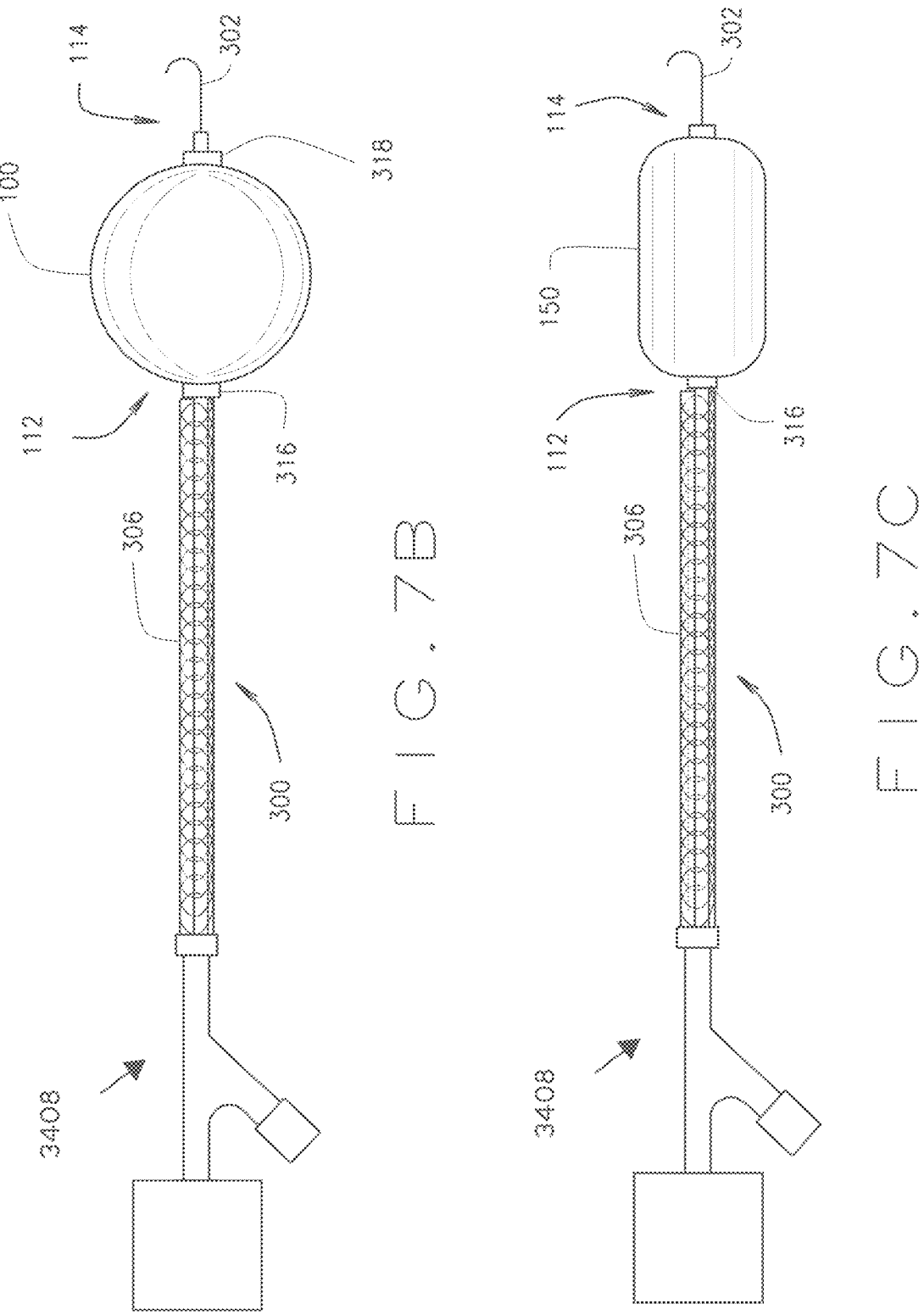

FIGS. 7A-C depict longitudinal views of a double lumen embodiment of the delivery catheter portion 300 of the medical device 500. FIG. 7A depicts a longitudinal view of a double lumen embodiment of the medical device 500 with the expandable body 100 or 150 in a compressed form, while FIG. 7B depicts a longitudinal view of a double lumen embodiment of the medical device 500 with the ballstent 100 in an expanded form. FIG. 7C depicts the medical device with the blockstent 150 in an expanded form. The delivery catheter 300 is used to advance the ballstent 100 over a guide wire 302 and into the lumen of the aneurysm sac. The delivery catheter 300 is also used to deliver a fluid, liquid, gas, solid, or a combination thereof, to expand the ballstent 100 in the lumen 701 of the aneurysm sac 700. In one embodiment, an electrolysis wire 320 or an insulated conductor wire is connected or electrically coupled to either a weld or solder joining the ballstent or blockstent to the delivery catheter. In another embodiment, an electrolysis wire 320 or an insulated conductor wire is connected or electrically coupled to a portion of the ballstent 100 at an exposed metal surface 3302.

As shown in FIGS. 6, 7A-B, and 8A-E, in one embodiment of the medical device 500, the delivery catheter 300 advances the attached compressed ballstent 100 over a guide wire 302 and into the lumen 701 of the aneurysm sac 700. Once the compressed ballstent 100 has been placed in the lumen 701 of the aneurysm sac 700, the guide wire 302 is removed. Then the wire or obturator 404 is removed from the delivery catheter 300. The wire or obturator 404 may include a handle 408 or other device to facilitate insertion and removal. Then, a fluid medium source, such as the syringe 314 is connected to the hub 3408 and a fluid medium is moved from the syringe 314 into the central void or space 108 of the ballstent 100 resulting in expansion of the ballstent until it fills at least a portion of the lumen of the aneurysm sac 701. As shown in FIG. 8E, after the ballstent 100 is expanded, the delivery catheter 300 and the ballstent 100 are separated and the delivery catheter is removed while leaving the expanded ballstent 100 within the lumen 701 of the aneurysm sac 700. In one embodiment, an electrolysis wire 320 or an insulated conductor wire is connected or electrically coupled to either a weld or solder joining the ballstent 100 and the delivery catheter, or to an exposed metal surface 3302 of the ballstent. For this embodiment, after the ballstent 100 is expanded, a DC current is applied to the electrolysis wire 320 or the insulated conductor wire to dissolve or corrode a portion of the weld or solder 316 between the ballstent 100 and the delivery catheter 300, or alternatively to dissolve or corrode the exposed metal surface 3302 of the ballstent 100 by electrolysis. Once the weld or solder 316 is dissolved or corroded, or alternatively the exposed metal surface portion of the ballstent 100 is dissolved or corroded, the delivery catheter 300 is separated from the ballstent 100 and the delivery catheter 100 and the guide catheter 800 are removed.

A similar method may be used to occlude a blood vessel with a blockstent 150. As shown in FIGS. 6, 7A, 7C, and 8F-J, the delivery catheter 300 advances the attached compressed blockstent 150 over a guide wire 302 and into the lumen 721 of the blood vessel segment 720. Once the compressed blockstent 150 has been placed in the lumen 721 of the blood vessel segment 720, the guide wire 302 is removed. Then the wire or obturator 404 is removed from the delivery catheter 300. The wire or obturator 404 may include a handle 408 or other device to facilitate insertion and removal. Then, a fluid source, such as the syringe 314 is connected to the hub 3408 and fluid is moved from the syringe 314 into the central void or space 108 of the blockstent 150 resulting in expansion of the blockstent until it fills at least a portion of the lumen of the blood vessel 721. As shown in FIG. 8J, after the blockstent 150 is expanded, the delivery catheter 300 and the blockstent 150 are separated and the delivery catheter is removed while leaving the expanded blockstent 150 within the lumen 721 of the blood vessel segment 720. In one embodiment, the delivery catheter comprises an electrolysis wire or an insulated conductor wire is connected or electrically coupled to either a weld or solder joining the blockstent 150 and the delivery catheter, or to the exposed metal surface 3302 of the blockstent. For this embodiment, after the blockstent 150 is expanded, a DC current is applied to the electrolysis wire 320 or insulated conductor wire to dissolve or corrode a portion of the weld or solder 316 between the blockstent 150 and the delivery catheter 300 or alternatively to dissolve or corrode the exposed metal surface 3302 of the blockstent 150. Once the weld or solder 316 is dissolved or corroded, or alternatively, the exposed metal surface portion of the blockstent 150 is dissolved or corroded, the delivery catheter 300 is separated from the blockstent 150 and the delivery catheter 150 and the guide catheter 800 are removed.

Guidance Members

As shown in FIGS. 8A-E, for an embodiment using a double lumen catheter, the delivery catheter 300 moves over a guidance member or guide wire 302 to deliver the compressed ballstent 100 to the lumen 701 of a saccular aneurysm 700. Examples of a guidance member include a flexible guide wire. The guide wire 302 can comprise metal in the form of a flexible thread, coil, or slender rod. For example, the basic angiography guide wire consists of a fixed solid metal core covered by a metal spring coil. In other situations, a delivery catheter is advanced over a needle or trochar. The guide wire 302 occupies a lumen in the delivery catheter, with such lumen defined by the tubular portion of the delivery catheter. Once located in place, the guide wire 302 can be removed in order to allow the injection or withdrawal of a fluid medium.

As shown in FIGS. 17A-B, in another embodiment, the delivery catheter of the medical device can be configured with a lumen that can accept a guide catheter 800 as a guidance member. With this configuration, the medical device can be advanced in a tri-axial configuration, with the medical device 500 advanced over a guide catheter 800, which is advanced over a guide wire. In certain embodiments, the proximal hub on the guide catheter can be removed to allow the lumen of the hollow cylindrical member 304 of delivery catheter 300 of the medical device 500 to accept the guide catheter 800. In certain instances, this embodiment of the medical device can result in better control over the delivery of the compressed expandable body to the aneurysm or target blood vessel lumen and better trackability of the compressed expandable body 100 or 150 as it is advanced to the desired location. As shown, in one aspect, the hollow cylindrical member 304 of delivery catheter 300 may be annular shaped and fully encircle the guidance catheter 800, while in other aspects, the delivery catheter may engage 60%, 70%, 80%, 90% or more of the circumference of the guidance catheter.

Exemplary Ballstent Catheter and Blockstent Catheter Medical Devices

FIG. 38A depicts an embodiment of a ballstent catheter medical device 3400A. As shown, the ballstent catheter medical device 3400A includes a delivery catheter 3402 configured at a distal end 3404 for engaging the ballstent 100. The proximal end 3406 of the delivery catheter 3402 is engaged to a hub 3408 that permits electrical and fluid communication with the ballstent 100 through the catheter. A syringe 314 may be used to delivery a fluid medium to the ballstent 100. The device 3400A also includes an electrical connector 3422 for establishing electrical communication from a power source 3418 to the ballstent 100.

FIG. 38B depicts an embodiment of a blockstent catheter medical device 3400B. As shown, the medical device 3400B includes a delivery catheter 3402 configured at the distal end 3404 for engaging the blockstent 150. The proximal end 3406 of the delivery catheter 3402 is engaged to a hub that permits electrical and fluid communication with the blockstent 150 through the catheter. A syringe 314 may be used to delivery a fluid medium to the blockstent 150. The device 3400B also includes an electrical connector 3422 for establishing electrical communication from a power source (not shown) to the blockstent 150.

A cross-section view of the hub 3408 is shown in FIG. 39. The hub 3408 includes a first connection port 3410 that is configured with a Luer hub or taper that may facilitate a Luer-Lok™ or Luer-Slip™ type connection for connecting a fluid medium source, such as a syringe 314, to the lumen 312 of a hollow cylindrical member of the delivery catheter 3402 configured to transmit the fluid medium from the proximal end of the delivery catheter to the central void or space 108 of the expandable body 100 or 150. Optionally, the first connection port 3410 is also configured to engage an obturator wire 404 or a guidewire 302.

The second connection port 3414 is configured to allow for electrical communication with the catheter 3402. For example, one or more electrolysis wire(s) 320 in electrical communication with electrodes mounted on the catheter 3402 and/or the ballstent 100 may extend through a channel 3416 of the hub 3408 and into the second connection port 3414. Alternatively, one or more resistive wires may extend through the channel 3416 of the hub 3408 and into the second connection port 3414. A power source or source of electricity, such as a handheld controller 3418 shown in FIGS. 38A and 40, may communicate with the wire 320 to perform various functions including, but not limited to, electrolysis or heating a heat-sensitive material.

In a preferred embodiment, the second connection port 3414 is bonded to a threaded nut 3420, such that an electrical terminal 3422 may be secured to the nut and the hub 3408.

The electrical terminal 3422 is in electrical communication with the one or more conductive wires and configured to receive an electrical connector from an external power source, such as the handheld controller 3418. By way of example and not limitation, the electrical connector 3424 may be a 3.5 mm audio jack. Other electrical connectors may also be used.

As shown in FIG. 40, the handheld controller 3418 can be connected to the electrical terminal 3422 through a jack 3424 to deliver an electrical current through the catheter 3402 for detaching the expandable body 100 or 150. For example, in one embodiment, the catheter 3402 includes a conductive coil 1006 that may be arranged in a one, two, or three conductor arrangement 1007, 1008, and 1010, respectively, as shown in FIGS. 29C and 29E and 29F. The various conductor arrangements 1008 and 1010 provide both reinforcing strength and a conductive pathway along the length of the catheter 3402. The handheld controller 3418 provides a current or a voltage potential to the electrodes 1014, 1016, and optionally 1026, extending through the catheter 3402 to detach the expandable body 100 or 150 by electrolysis or thermal detachment, as explained below. In one embodiment, the handheld controller 3418 includes a body 3426, a power supply such as a battery, one or more actuation buttons 3428, and one or more indicators 3430 to indicate the status of the controller, the detachment of the expandable body 100 or 150, and the status of the power source, such as the battery.

Folding the Expandable Body

In order to facilitate advancement of the expandable body through the vascular system, some embodiments of the expandable body 100 or 150 comprise two or more metallic portions 1900A-B that are joined by a flexible joint 1902, as shown in FIG. 13. In certain embodiments, this flexible joint can comprise a variety of materials that are flexible and biocompatible, including various polymers or elastomers. The joint 1902 allows for better maneuverability and increased trackability as the compressed expandable body is advanced to the desired location. In other embodiments, the expandable body 100 or 150 may include three or more metallic or rigid portions that are joined through two or more flexible joints.

In order to facilitate advancement of the expandable body through the vascular system, the expandable body 100 or 150 can be compressed into various shapes and dimensions. Optionally, this compression can include various forms and patterns of folding or pleating. For example, one or more pleats can be made in the expandable body 100 or 150 and then the pleats can be wrapped into a cylindrical shape. Alternatively, the expandable body 100 or 150 may be flattened into a planar shape and then rolled into a cylindrical shape. Alternatively, the expandable body 100 or 150 may be compressed into a compact spherical shape. Additionally, the portions of the expandable body 100 or 150 may be twisted during compression. In certain instances, the expandable body may be compressed around the delivery catheter 300, as in FIG. 7A. In other instances, the expandable body may be compressed around the obturator 404, as in FIG. 3A. In other embodiments, the expandable body 100 or 150 may be compressed on itself, without a central catheter or obturator.

In FIG. 14A, the expandable body 100 or 150 has been pleated, folded, and wrapped around the hollow cylindrical member 304 of the delivery catheter 300. In FIG. 14B, the expandable body 100 or 150 is pleated and wrapped without being wrapped around the delivery catheter. In another embodiment, the expandable body 100 or 150 is folded into pleats, then the pleats of the folded expandable body are wrapped around the hollow cylindrical member 304 of the delivery catheter 300, and the expandable body is compressed against the delivery catheter, as shown in FIG. 14C. In another embodiment, the expandable body 100 or 150 is folded into pleats, then the pleated folds of the folded expandable body are wrapped around the removable wire or obturator 404, and then the expandable body is compressed against the removable wire or obturator 404. In another embodiment, the expandable body 100 or 150 is folded into pleats, and then the pleated folds are rolled into a generally cylindrical shape without a removable wire or obturator or catheter acting as central fixation point, as shown in FIG. 14D.

In various embodiments, the expandable body 100 or 150 is attached to the delivery catheter 300, 400, then the pleats are formed, and then the pleated folds are wrapped and compressed onto the delivery catheter 300, or the obturator 404. In another embodiment, the expandable body 100 or 150 is first folded to form pleats, and then attached to the delivery catheter 300, 400, and then the pleated folds are wrapped and compressed onto the outer surface of the delivery catheter 300, or obturator 404. In another embodiment, the expandable body 100 or 150 may be folded and compressed into a variety of shapes in a manner similar to Japanese origami, as shown in FIGS. 15A-D.

The expandable body 100 or 150 may be folded to form one or more pleats, which may be further folded, rolled, and compressed, similar to the folding of non-compliant angioplasty expandable bodies. In various other embodiments, the pleated expandable body is folded and compressed to fit on the end of a flexible guide wire and travel within a hollow cylindrical member of a separate catheter. The expandable body 100 or 150 may be folded and compressed using any suitable arrangements and methods. It is desired that the expandable body 100 or 150 have smooth even folds.

Expandable Body Folding Tool

In one embodiment, the expandable body 100 or 150 may be folded using a folding tool 3500 as shown in FIGS. 41A-C. The folding tool 3500 is configured to form pleats within the expandable body 100 or 150 and to wrap the expandable body to further minimize the cross-sectional area of the collapsed expandable body. The folding tool 3500 includes a folding assembly 3502 and a removable collet assembly 3504.

The folding assembly 3502 includes a base 3506 defining a centrally positioned opening 3508 for receiving the collet assembly 3504. The centrally positioned opening 3508 is threaded such that the collet assembly can be secured to the base 3506. On top of the base 3506, an annular folding die 3510 is positioned coaxially with the opening 3508. The annular folding die 3510 is slidably engaged to the base 3506, such that the annular folding die may rotate about the central axis 3512.

The annular folding die 3510 includes a flat annular ring 3514 having an outer diameter D1, an inner diameter D2, and a plurality of projections 3516 that extend diagonally away from the inner surface 3518 of annular ring towards the axis 3512 and nearly converge at the axis at a height H above the annular ring. The distal end 3520 of each projection 3516 defines a vertical-oriented blade 3522 having a height h and extending radially inwards a distance d towards the axis 3512. In one embodiment, the thickness blade 3522 tapers along d as it approaches the axis 3512, in another embodiment, the blade has a uniform thickness. In one embodiment, the projections 3516 are flexible and integrated with the ring 3514, or alternately, mechanically engaged to the ring.

The annular ring 3514 is held against the base 3506 by a cover plate 3524. The cover plate 3524 is mechanically engaged by fasteners 3526 to the base 3506 and one or more stand-offs 3528. The cover plate 3524 defines a first central recess 3530 having a diameter D3 and a second central recess 3532 that is coaxial with the first central opening and having a diameter D4 that is smaller than D3. The diameter D3 of the first central recess 3530 is greater than the outer diameter D1 of the annular ring 3514, such that the annular ring can rotate within the first central recess. The diameter D4 is greater than the inner diameter D2 of the annular ring, 3514 but less than the outer diameter D1, such that the cover plate 3524 can hold the annular folding die 3510 against the base 3506, but still permit rotation of the annular folding die 3510.

The cover plate 3524 also includes at least one arcuate channel 3534 that receives a bolt (not shown) engaged to the annular ring 3514 and a thumbscrew 3536, such that the thumbscrew can be used to rotate the annular folding die 3510. The cover plate 3524 also defines one or more openings 3538 to receive one or more compression ring slide shafts 3540. The slide shafts 3540 are slidably engaged to a compression ring slide 3542 that engages the annular folding die 3510. In one embodiment, return springs 3544 are engaged to the slide shafts 3540 and the compression ring slide 3542 to apply a biasing force that returns the compression ring slide to a default position.

The compression ring slide 3542 defines an annular opening 3544 that engages the projections 3516 of the annular fold die 3510. The compression ring slide 3542 also defines a drive hole 3546 to receive a drive screw 3548 with a knob 3550, through an optional bushing nut 3552. Rotation of the drive screw 3548 causes the compression ring slide 3542 to translate along the compression ring slide shafts 3540. For example, rotation of the drive screw 3548 may cause the compression ring slide 3542 to translate along the compression ring slide shafts 3540 towards the base 3506. As the compression ring slide shafts 3540 moves towards the base 3506, the annular opening 3544 engages the projections 3516 causing each blade 3522 to translate radially inward towards the axis 3512 and an expandable body 100 or 150 held in the removable collet assembly 3504.

Referring now to FIGS. 42A-C, the removable collet assembly 3504 includes a collet 3554 to compress a compression tube 3556 and a center pin 3558 received within the compression tube. In one embodiment, the compression tube 3556 may compress and hold the neck 116 of an expandable body 100 or 150 that is placed on the center pin 3558. In one embodiment, a tacky elastomeric material (not shown) is placed around the neck to protect the neck from the clamping surfaces of the collet 3554. The collet 3554 is held against a collet piston 3560, by a cap 3562. The collet piston 3560 also receives a piston stop 3564 and one or more anti-rotation pins 3566 that prevent undesired rotation of the piston stop and collet 3554, which prevents rotation of the compression tube 3556 and the center pin 3558. The collet piston 3560 engages a piston spring 3568 within a base 3570, where the piston spring permits longitudinal translation of the collet piston 3560.

By way of example and not limitation, an expandable body 100 or 150 to be folded may be engaged to the removable collet assembly 3504, by placing the center pin 3558 within the neck 116 and positioning the compression tube 3556 to engage the exterior surface of the neck. The collet assembly 3504 is assembled so that the collet 3554 compresses the compression tube 3556 against the neck 116 and the center pin 3558. The collet assembly 3504 is then attached to the folding assembly 3502.

The drive screw 3548 is rotated to translate the compression ring slide 3542 along the slide shafts 3540 towards the base 3506. As the compression ring slide 3542 moves towards the base 3506, the annular opening 3544 engages the projections 3516 causing each blade 3522 to translate radially inward and engage the expandable body 100 or 150. Each blade 3522 deforms the expandable body to form a plurality of pleats 3600, as shown in FIGS. 43A-B. Each pleat 3600 includes a ridge line 3602 extending proximal-distal and radially away from the axis 3512. Each pleat is separated from any immediately adjacent pleat by an interposed trough 3604 extending proximal-distal.

After the plurality of pleats 3600 are formed, the compression ring slide 3542 is raised slightly, causing each blade 3522 to partially disengage with the expandable body 100 or 150 held in the removable collet assembly 3504. The annular folding die 3510 is rotated about the axis 3512 by translation of the bolt and a thumbscrew 3536 along the at least one arcuate channel 3534. In one embodiment, the rotation of the annular folding die 3510 folds each pleat 3600 of the plurality of pleats over an immediately adjacent pleat 3600 in a clockwise direction relative to the center axis 3512 or, alternately, in a counter-clockwise direction.

FIGS. 43A-B are, respectively, side and axial end views of the expandable body 100 or 150 in a progressive series of stages of being collapsed, folded, and wrapped. Starting in an inflated configuration indicated as 3800, the expandable body 100 or 150 is simultaneously compressed and folded by the folding tool 3500, as indicated as 3802-3806. Once the pleats 3600 are fully formed as indicated at 3806, the folding tool 3500 may be used to rotate the formed pleats 3600 and wrap the pleats upon the expandable body 100 or 150 into a fully compressed deliverable configuration, indicated as 3808. Preferably, as can be understood from FIGS. 9E, 9G, and 14B, the expandable body 100 or 150 is wrapped upon itself and not a delivery device. More specifically, the delivery device 220 only extends into the neck of the expandable body 100 or 150; no part of the delivery device 220 extends into folded over region of the expandable body. In other words, the delivery device only extends into the neck of the expandable body 100 or 150 but does not extend into the volume 108 of the expandable portion of the expandable body. In such an embodiment as can be understood from FIGS. 14B-C, the folded region of the expandable portion of the expandable body may define a center channel 1400A or an off-center channel 1400B that can accept a guide wire or other delivery device. Alternately, as can be understood from FIG. 14D, the folded region may not receive a guide wire or other delivery device and therefore does not define a channel. In other embodiments, as can be understood from FIG. 14A, the expandable body is wrapped around a distal region of the delivery device.

The expandable body 100 or 150 is preferably folded such that a distal end portion 202 of the expandable body extends distally away from the interior void of the expandable body, and a proximal end portion 208 of the expandable body extends proximally away from the interior void 108 of the expandable body. In other embodiments, the expandable body 100 or 150 may be folded such that the distal end portion 202 is folded proximally inward towards the interior void 108, and the proximal end portion may also be folded distally inward towards the interior void.

FIGS. 44A-B depict an alternate embodiment of the folding tool 3500. In this embodiment, the compression ring slide 3700 is an annular ring that is manually pushed against a non-rotatable annular folding die 3702. In addition, the collet assembly 3704 is manually rotated to rotate the expandable body 100 or 150 after forming the plurality of pleats 3600 to effect folding of the pleats in either a clockwise or counterclockwise manner.

FIG. 44C depicts a partial cross-sectional view of an expandable body 100 or 150 within the folding tool 3500. In one embodiment, the expandable body 100 or 150 is partially or completely expanded prior to folding. The collet assembly 3504 may be in fluid communication with one or more pressurized fluid or air lines 3572 such that a fluid medium or a gas may be delivered to the expandable body 100 or 150 through the hollow center pin 3558. The pressurized air line 3572 extends from the collet assembly 3504 to a low pressure inflation device, such as an air pump or an endoflator, (not shown) or alternately, a fluid source, such as a syringe 314. In one embodiment, a low pressure check valve 3574 is configured in line with the pressurized air line 3572. In another embodiment, the pressurized air line 3572 is split and connected to the low pressure inflation device and a separate a low pressure check valve 3574. In one embodiment, the check valve 3574 may be configured to split open or otherwise release air under a specific internal air pressure to allow air to bleed out of the check valve and prevent the over inflation of the expandable body 100 or 150 during folding.

After the expandable body 100 or 150 is mounted into the collet assembly 3504, the collet assembly holds the expanded body neck 116 neck tightly around the central pin 3558 to form an air tight seal with the pressurized air line 3572. Approximately 1-5 psi of positive pressure is delivered to the air line 3572 to the expandable body 100 or 150. As the folding die 3510 engages the expandable body 100 or 150, the gradually decreasing internal volume of expandable body increases the internal pressure therein. The increase in pressure is mitigated by the check valve 3574, such that the internal pressure within the expandable body is constant while being folded. Maintaining a constant, positive pressure inside the expandable body 100 or 150 prevents the expandable body from collapsing in areas not in direct contact with the folding die 3510. This allows for a smoother, more regular collapse of the expandable body 100 or 150.

Attaching and Detaching the Expandable Body

The expandable body 100 or 150 may be attached to, or engaged with, the delivery catheter in a variety of ways. For example, the expandable body 100 or 150 may be affixed to the delivery catheter by a friction fit, using an adhesive, or glue, by a weld or solder, by a junction or uniting of components, or by the application of a compressive force from a clamp, ring, elastomer sleeve or wrap, or compressive balloon. Various methods and devices may be used to separate the expanded expandable body from the delivery catheter. By way of example and not limitation, these methods and devices may be broadly categorized as physical or mechanical, electrical, thermal, chemical, hydraulic, and sonic.

Mechanical Attachment by Friction

Figure 23B:
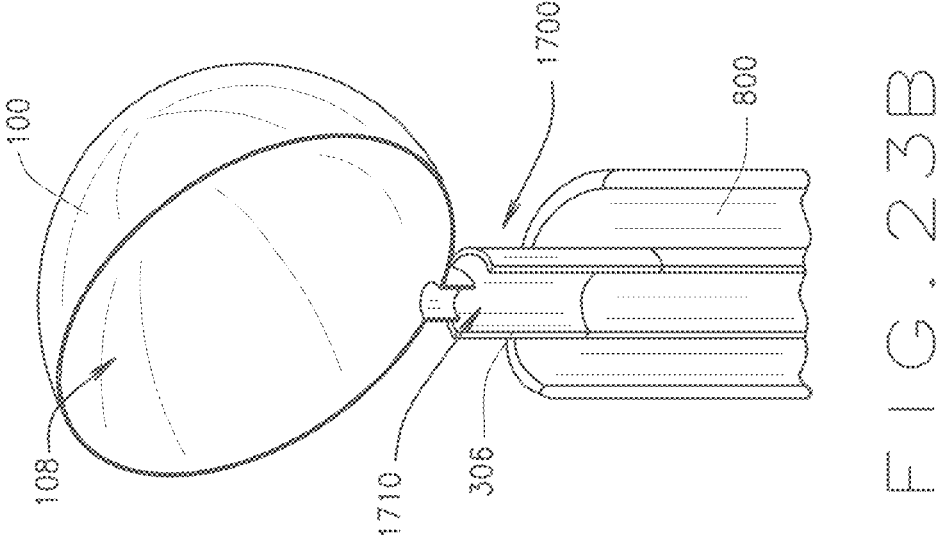
Figure 23A:
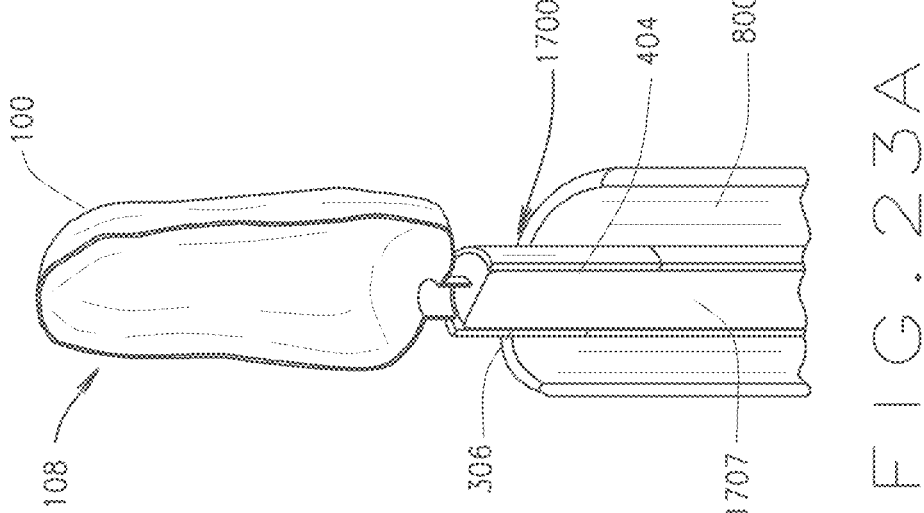
Figures 24A, 24B:
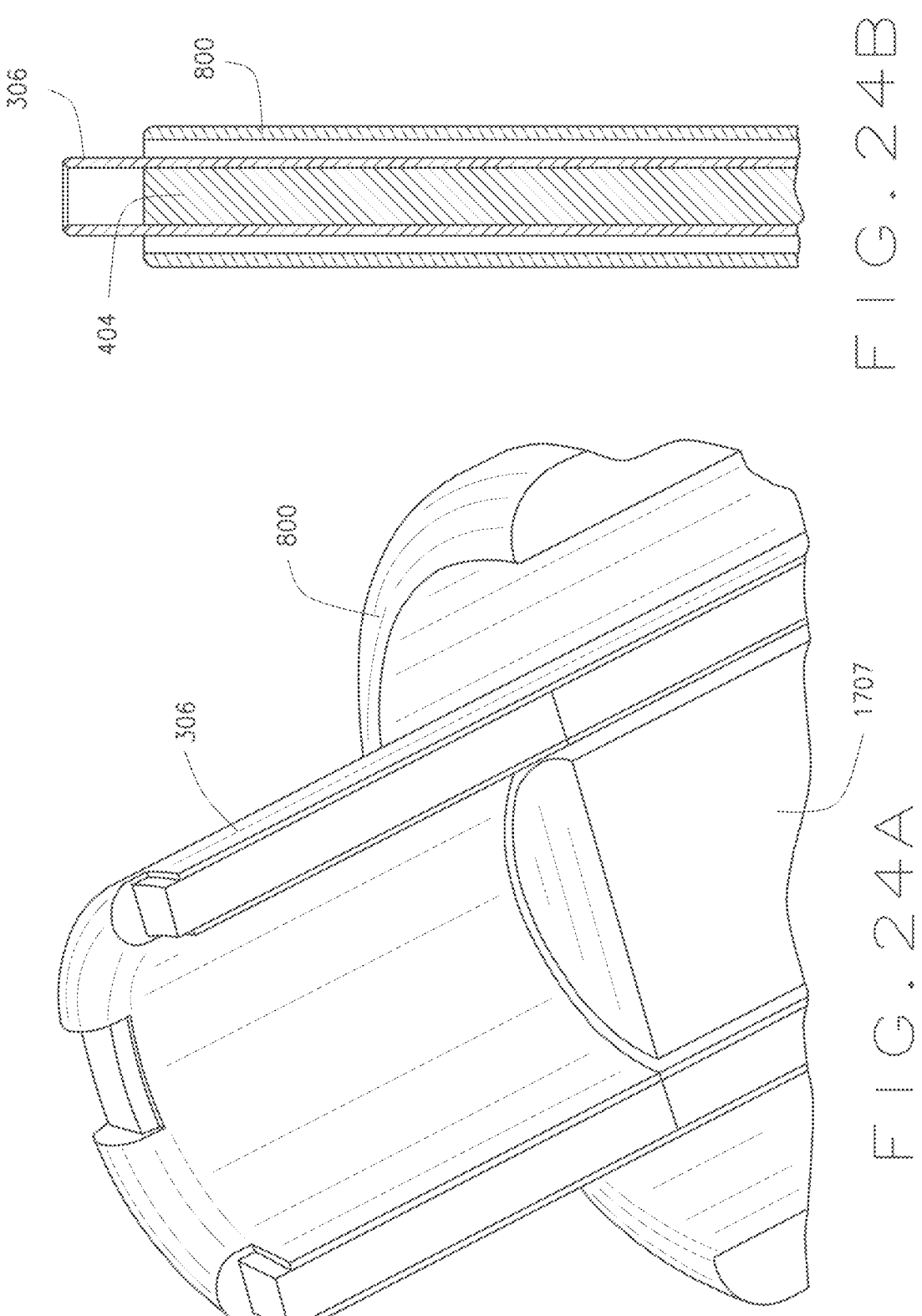
FIGS. 24A-B are a perspective view and a longitudinal cross-sectional view, respectively, of embodiments of the delivery catheter of the medical device wherein the delivery catheter has been advanced through the lumen of a guide catheter.

In one embodiment, a physical or mechanical attachment is made between an expandable body and a delivery catheter, wherein the coupled parts are configured to fit tightly together and remain together by friction. After expansion of the expandable body, the physician slips the distal end of delivery catheter out of the neck of the expandable body to effect separation, a process that may be facilitated by moving a guide catheter 800 forward to abut the expanded expandable body 100 or 150 prior to withdrawing the delivery catheter, as shown in FIG. 23B. In one embodiment shown in FIG. 18, the neck 1600 of the expandable body 100 or 150 engages the distal end 1706 of the core wire or obturator 404 by friction. As shown in FIGS. 18, 23A-B, and 24A-B, the distal portion 1706 of the core wire or obturator 404 of the delivery catheter 400 has a smaller diameter than the more proximal portion 1707. In other embodiments, the distal portion 1706 of the core wire or obturator 404 of the delivery catheter 400 has the same diameter as the more proximal portion 1707. After the compressed expandable body 100 or 150 is positioned in the lumen of a saccular aneurysm, the core wire or obturator 404 is removed. This creates a fluid medium pathway through the lumen 312 of the delivery catheter 400 and into the central void or space 108 of the expandable body 100 or 150. Once the obturator 404 is removed, a fluid medium source 314 can be connected to hub 3408 and the fluid medium can be injected into the void 108 of the expandable body 100 or 150 until it is expanded. After the expandable body 100 or 150 is expanded, the distal end of the guide catheter 800 is advanced forward against the wall of the expanded expandable body 100 or 150 and the distal end of the delivery catheter 400 is withdrawn from the neck of the expandable body 1600 to separate the delivery catheter from the expanded expandable body, allowing the delivery catheter to be removed while leaving the expanded expandable body in the lumen of the saccular aneurysm or the lumen of the target vessel segment. In this way, the guide catheter 800 functions as a buttress against the exterior surface of the expandable body 100 or 150, while the expanded expandable body is separated from the delivery catheter.

Figure 25A:
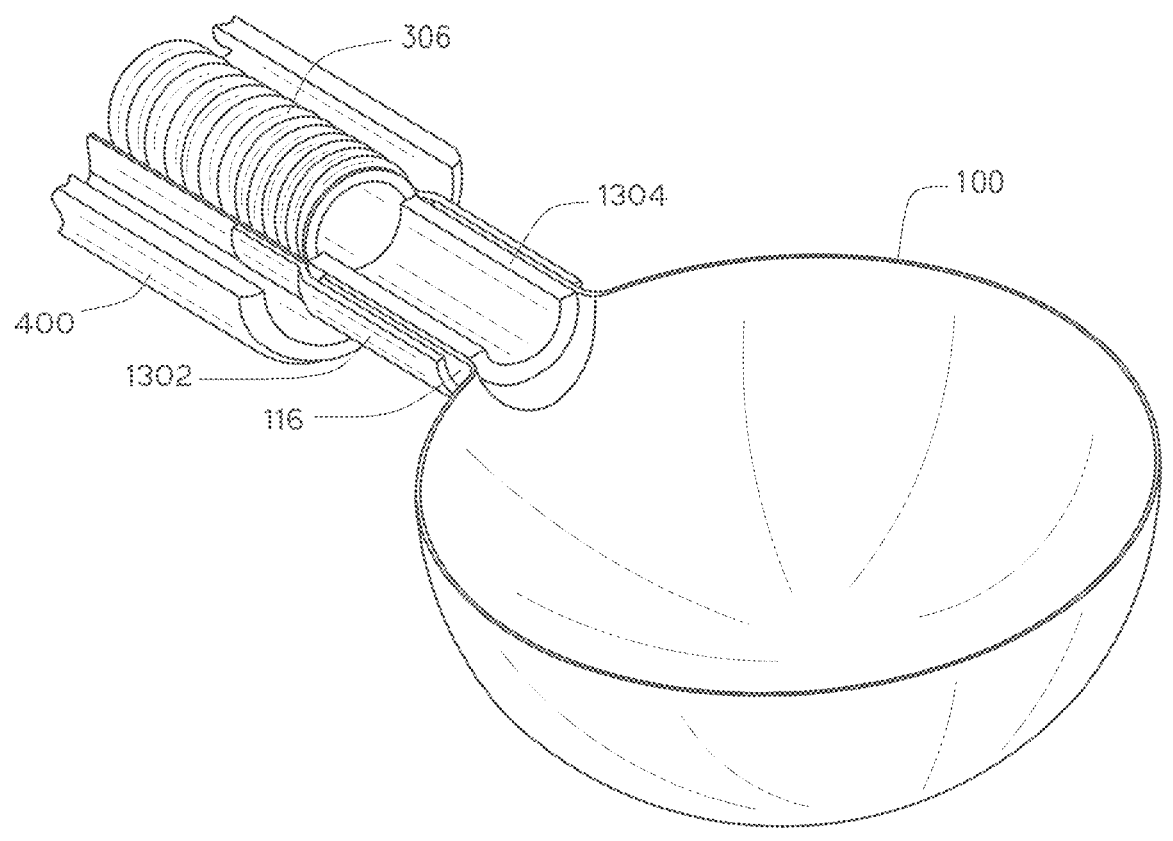
FIG. 25A is a perspective view of a partial cross-section of an embodiment of the medical device wherein the neck of the expandable body is attached to the delivery catheter, an elastomeric sleeve holds the neck of the expandable body to the delivery catheter, and the expandable body is expanded.

Alternatively, the expandable body and delivery catheter can be separated by other physical methods. In another embodiment, as shown in FIG. 25A, a mechanical attachment is made between an expandable body and a delivery catheter wherein an external neck 116 on the expandable body 100 or 150 is configured to fit tightly around the distal end of the hollow cylindrical member 306 of the delivery catheter 400. An elastic sleeve or wrap 1302 is attached to distal end 1304 of the hollow cylindrical member 306 of the delivery catheter 400 and extended around at least a portion of the external neck 116 of the expandable body 100 or 150 to hold the neck of the expandable body against the distal end of the hollow cylindrical member 306 of the delivery catheter 400. Once the expandable body is expanded in the lumen of the saccular aneurysm or the lumen of the target vessel segment, the expanded expandable body 100 or 150 is separated from distal end of the hollow cylindrical member 306 of the delivery catheter 400 by using the guide catheter 800, similar to above, to buttress the expandable body while the distal end of the hollow cylindrical member 306 of the delivery catheter 400 is pulled away from the expanded expandable body.

Mechanical Attachment by an Elastomer Sleeve

Figures 25B, 25C, 25D:
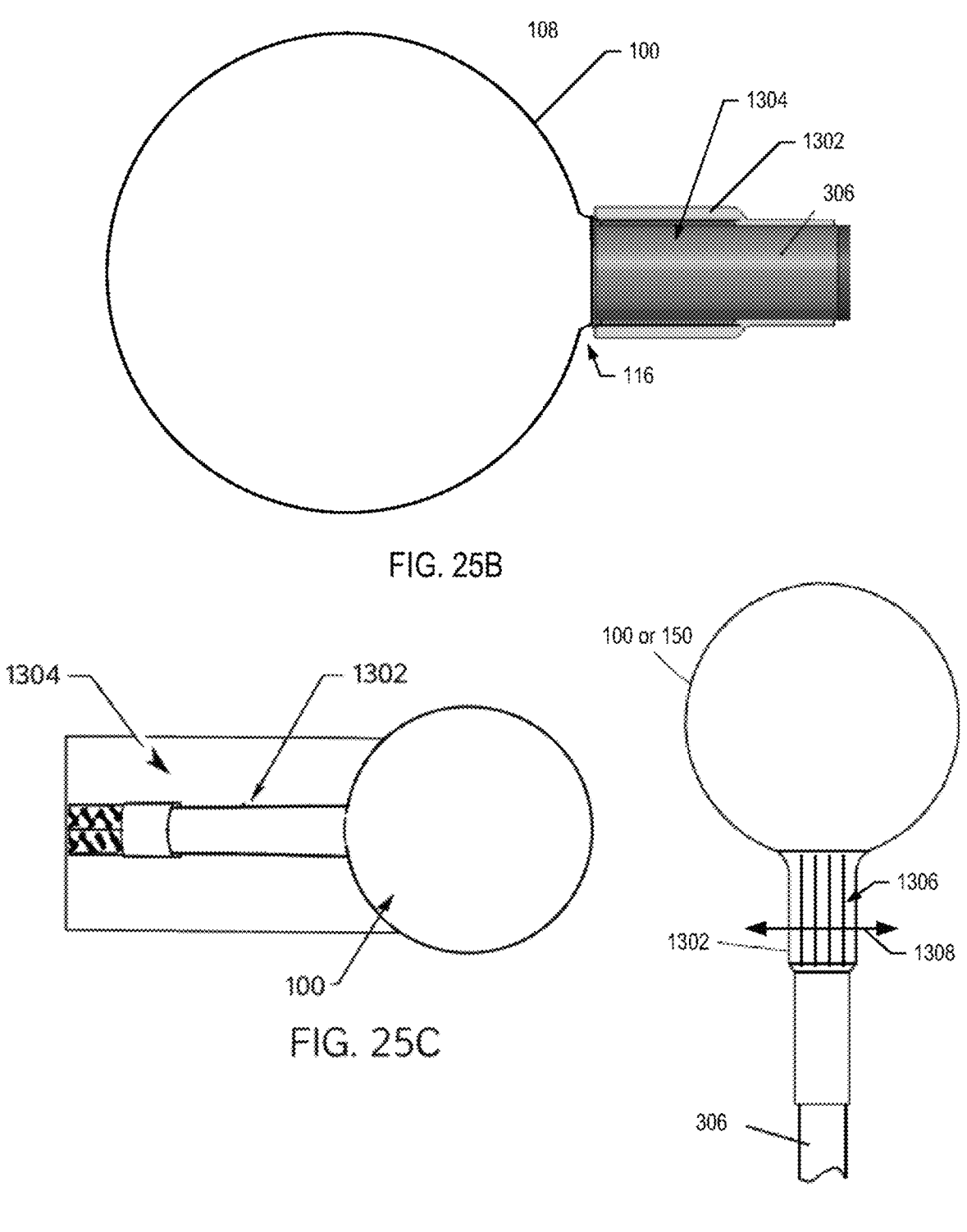
FIG. 25B is a perspective view of a partial cross-section of an embodiment of the medical device wherein the neck of the expandable body is attached to the delivery catheter with an elastomeric sleeve.
FIGS. 25C-D are plan views of an expandable body attached to a delivery catheter with an elastomeric sleeve.

As shown in FIGS. 25B-D, an elastomer sleeve or wrap 1302 is compressively or frictionally engaged around the distal end 1304 of the delivery device 306. To engage the expandable body 100 or 150 to the delivery device, according to one embodiment, the elastomer sleeve 1302 is rolled back away from the distal end 1304 of the delivery device 306, the neck 116 of the expandable body is slipped over the distal end of the delivery device 306 and the elastomer sleeve is rolled back towards the distal end of the delivery device to engage and compress around the exterior surface 3300 of the expandable body neck. The neck of the expandable body 116 is therefore held between the distal end of the delivery device 306 and the elastomer sleeve 1302.

In a preferred embodiment, shown in FIGS. 25A-B, the delivery device 306 does not extend into the interior void 108 of the expandable body 100 or 150, such that the expandable body may be collapsed, folded, and/or pleated onto itself. The elastomer sleeve 1302 secures the expandable body 100 or 150 to the delivery device 306 during positioning, inflation, and detachment. In one embodiment, the elastomer sleeve 1302 secures the neck 116 of the expandable body 100 or 150 to the delivery device 306 as electrolysis is performed at the exposed strip 3302. In another embodiment, the expandable body 100 or 150 may be detached from the delivery device 306 by pulling the delivery device away from the expandable body 100 or 150 after expansion.

The elastomer sleeve 1302 may have an inner diameter ranging between about 0.025 inches and 0.04 inches, with a thickness ranging between about 0.002 inches and 0.01 inches. In a preferred embodiment, the elastomer sleeve 1302 has an inner diameter of approximately 0.028 inches with a wall thickness of about 0.008 inches. The elastomer sleeve 1302 may be any suitable biocompatible elastomer, including but not limited to ChronoPrene™ manufactured by AdvanSource Biomaterials of Wilmington, MA or polyether block amide (PEBA), commonly known under the trade name of PEBAX®, manufactured by Arkema of Colombes, France. In a preferred embodiment, the elastomer sleeve 1302 is composed of 2533 or 25 Shore D durometer PEBAX®.

In one embodiment, shown in FIG. 25D, the elastomer sleeve 1302 may be manufactured to include a number of ribs 1306. The ribs 1306 provide structural support to the sleeve 1302. The ribs also permit the elastomer sleeve 1302 to stretch in laterally, in a direction perpendicular to the ribs as indicated by 1308. In this embodiment, the elastomer sleeve 1302 does not stretch longitudinally in line with the ribs 1306.

Mechanical Detachment Arrangements

In various other embodiments, the expandable body 100 or 150 is attached to the distal end of the hollow cylindrical member 306 of the delivery catheter 400 with an adhesive, glue, weld, or solder. In these embodiments, the expanded expandable body 100 or 150 is separated from delivery catheter 400 by one or more mechanical methods. The expanded expandable body 100 or 150 may be separated from the delivery device by a number of mechanical methods that cut, tear, or otherwise physically degrade a portion of the expandable body to separate the remainder of expandable body from the delivery catheter 400.

Figure 19:
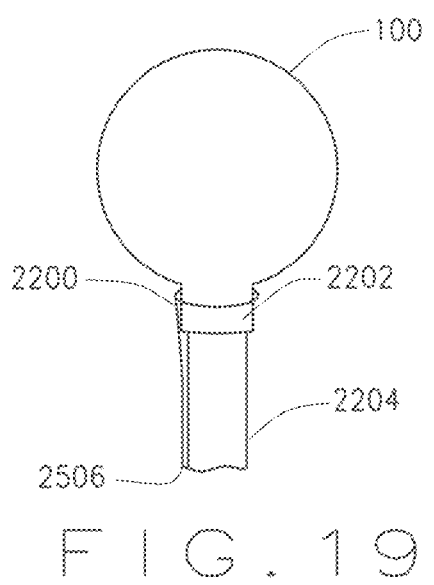
FIG. 19 is a plan view of a component and a method for separating an expandable body from a delivery catheter.

As shown in FIG. 19, in one embodiment, a flexible, thin loop of material 2200 may be positioned to encircle the outside of the external neck of the expandable body 2202. The loop of material can be formed of various thin, strong, and flexible materials such as a wire, polymer strand, filament, string, thread, or snare. After expansion of the expandable body, the loop can be pulled toward the proximal end of the delivery catheter 2204 to sever the neck 2202 of the expandable body 100 or 150, and separate the expanded expandable body from the delivery catheter. Preferably, the loop is pulled through a lumen in the delivery catheter dimensioned to accept the loop as it is pulled back. In another embodiment (not shown), a flexible thin loop of material (in certain embodiments representing a loop snare or modified loop snare) can be advanced by a second catheter until the loop is placed around the outside of the proximal portion of the external neck of an expanded expandable body. The loop can then be snugged against the neck and withdrawn into the second catheter in order to sever the neck 116 of the expandable body 100 or 150 and separate the expandable body from the delivery catheter.

Figure 20:
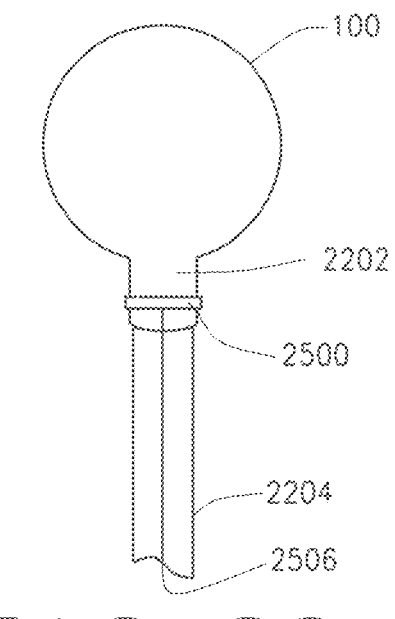
FIG. 20 is a plan view of a component and a method for separating an expandable body from a delivery catheter.

In another embodiment shown in FIG. 20, a distal end 2500 of a thin loop of material (such as a wire, polymer strand, filament, string, or thread) is affixed in a loop to the expandable body neck 2202, while the proximal end 2506 of the loop material extends to the proximal end of the delivery catheter 2204. After expansion of the expandable body 100 or 150, the loop of material is pulled toward the proximal end of the delivery catheter 2204, which tears a portion of the neck 2202 away from the expanded expandable body 100 or 150 to separate the expandable body from the delivery catheter.

Figure 21A:
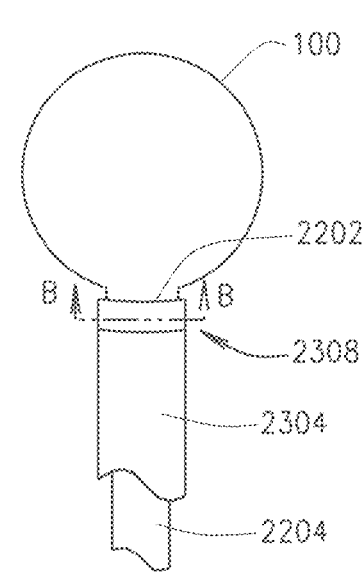
FIG. 21A is a plan view of a component and a method for separating an expandable body from a delivery catheter.
Figure 21B:
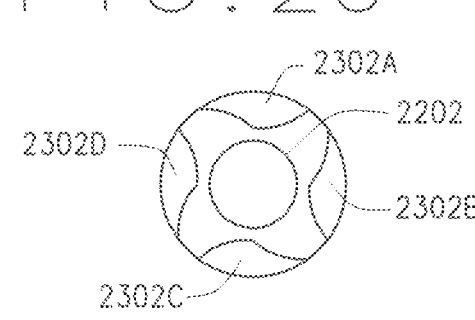
FIGS. 21B-C are cross sections taken along section line B-B in FIG. 21A.
Figure 21C:
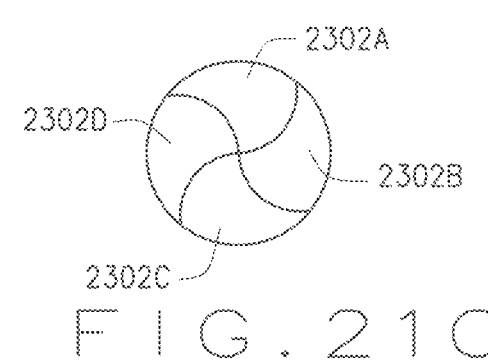

In another embodiment shown in FIGS. 21A-C, the neck 2202 of the expandable body 100 or 150 may be cut by one or more blades 2302A-D. In this embodiment, a cutting device 2304 is advanced over the delivery catheter 2204. The cutting device 2304 has a cutting region 2308 that includes the blades 2302A-D. When the expanded expandable body 100 or 150 is to be separated from the delivery catheter, the cutting device 2304 is positioned such that the neck 2202 is within the cutting region 2308. The blades 2302A-D may then be actuated to sever the neck 2202. By way of example and not limitation, the blades 2302A-D may be actuated by rotation of the cutting device, insertion of a wire, retraction of a wire, or other suitable methods. FIGS. 21B-C are cross-sectional views along line B-B of the cutting region prior to (FIG. 21B) and during actuation of the blades (FIG. 21C).

In another embodiment, shown in FIG. 22, the neck 2202 of the expandable body 100 or 150 may define a plurality of circumferential perforations 2406. The perforations 2406 are torn as the delivery catheter 2204 is pulled away from the expandable body 100 or 150.

In another embodiment, a ring structure is fixed to the distal end of the delivery catheter, while a second ring structure is fixed to the proximal end of the expandable body, with a mating of the two rings attaching the expandable body to the delivery catheter. After expansion of the expandable body, the rings can be disengaged, resulting in separation of the expanded expandable body 100 or 150 and the delivery catheter. The unlocking of the rings could be accomplished by actuating a spring-loaded clamp or other similar methods in order to release the expandable body.

In other embodiments, hydraulic methods may be used to separate the expanded expandable body 100 or 150 from the delivery catheter device. In one embodiment, the expanded expandable body 100 or 150 separates from the delivery catheter after the fluid medium is injected through a lumen to actuate a mechanical joint between the expandable body 100 or 150 and the delivery catheter, resulting in separation of the expanded expandable body 100 or 150 and the delivery catheter.

Detachment by Electrolysis

One method for using electrolysis to detach the expandable body 100 or 150 may be performed using the one, two, or three electrical conductor single lumen catheters 1000, as shown in FIGS. 29B-F. The one or two conductor arrangement 1007 and 1008, respectively, may be used to perform constant current electrolysis. The three conductor arrangement 1010 may be used to perform constant voltage electrolysis or electrolysis using a square-wave voltage potential. In any of these arrangements, the electrical conductors may be composed of any biocompatible conductive material including platinum, stainless steel, gold, or silver, and alloys thereof. In one example, the electrical conductors may be a platinum-iridium alloy.

When using the one or two electrical conductor arrangement 1008 to perform constant current electrolysis, there is less control over the voltage potential in the anode or working electrode 1014. As such, the voltage potential at the working electrode 1014 increases until the potential and current flowing to the working electrode 1014 is sufficient to cause oxidation of ions in the bloodstream at the working electrode. For example, the current may break down $H_2O$ molecules in the bloodstream to form $H^+$ ions and electro-negative $O_2$ molecules. The $O_2$ molecules then bond to the exposed gold at the detachment site of a gold expandable body 100 or 150 and dissolve the exposed gold strip. The polymer coating on the expandable body 100 or 150 is a dielectric that prevents the $H^+$ ions and $O_2$ molecules from reacting with the coated portions of the expandable body.

Figure 29G:
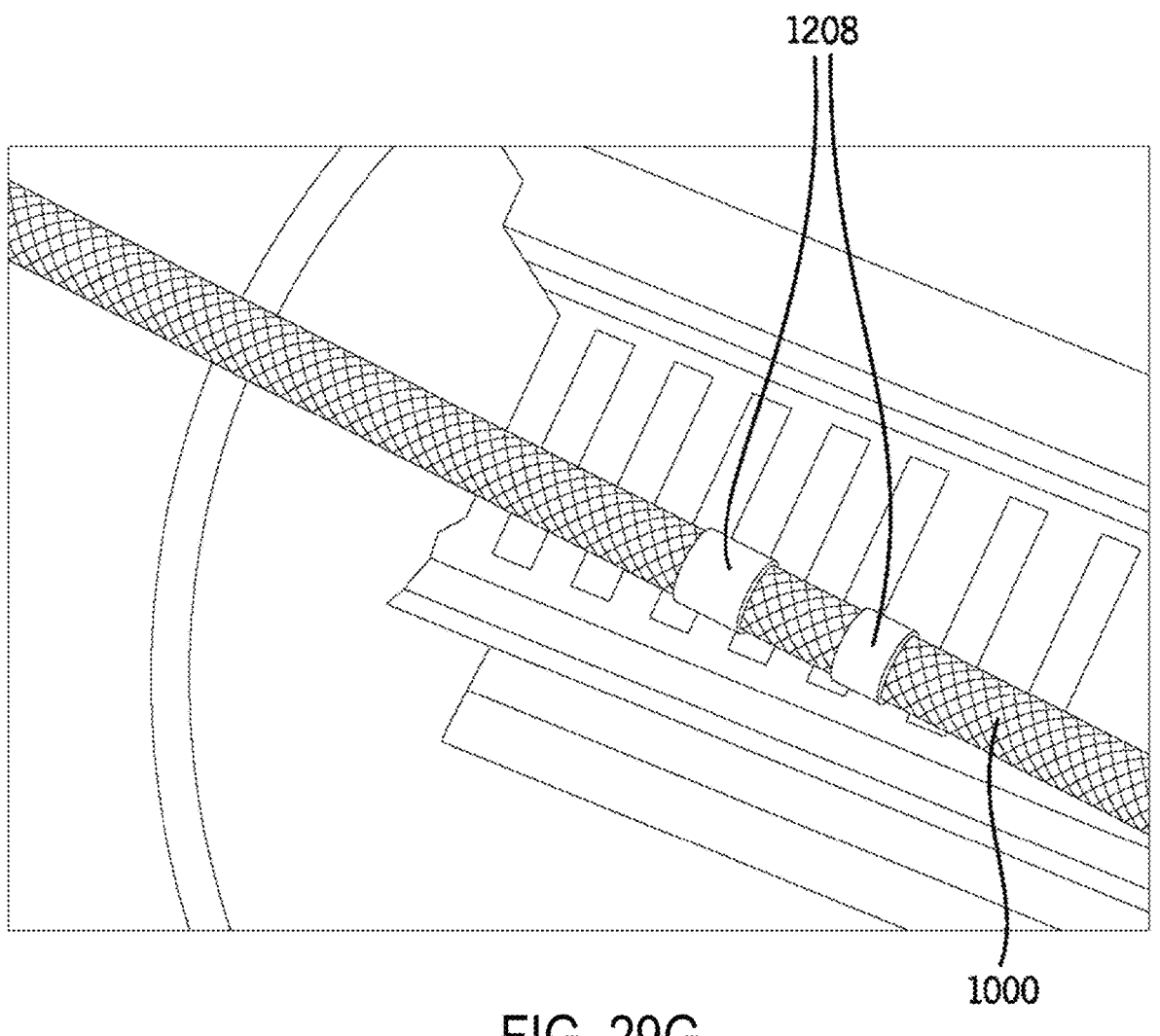
FIG. 29G is a plan view of a catheter supporting one or more electrode rings.
Figure 29H:
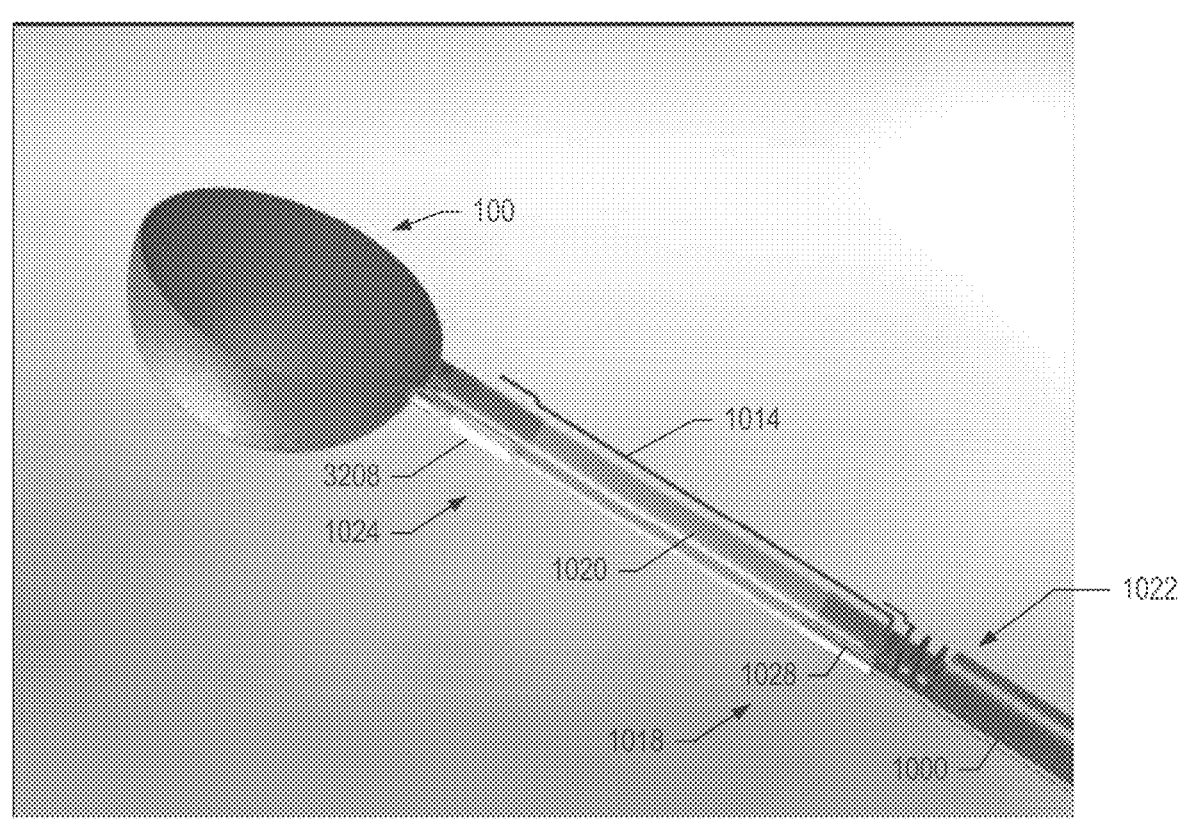
FIGS. 29H-I are partial cross-section and perspective views of an expandable body attached to a delivery device.
Figure 29I:
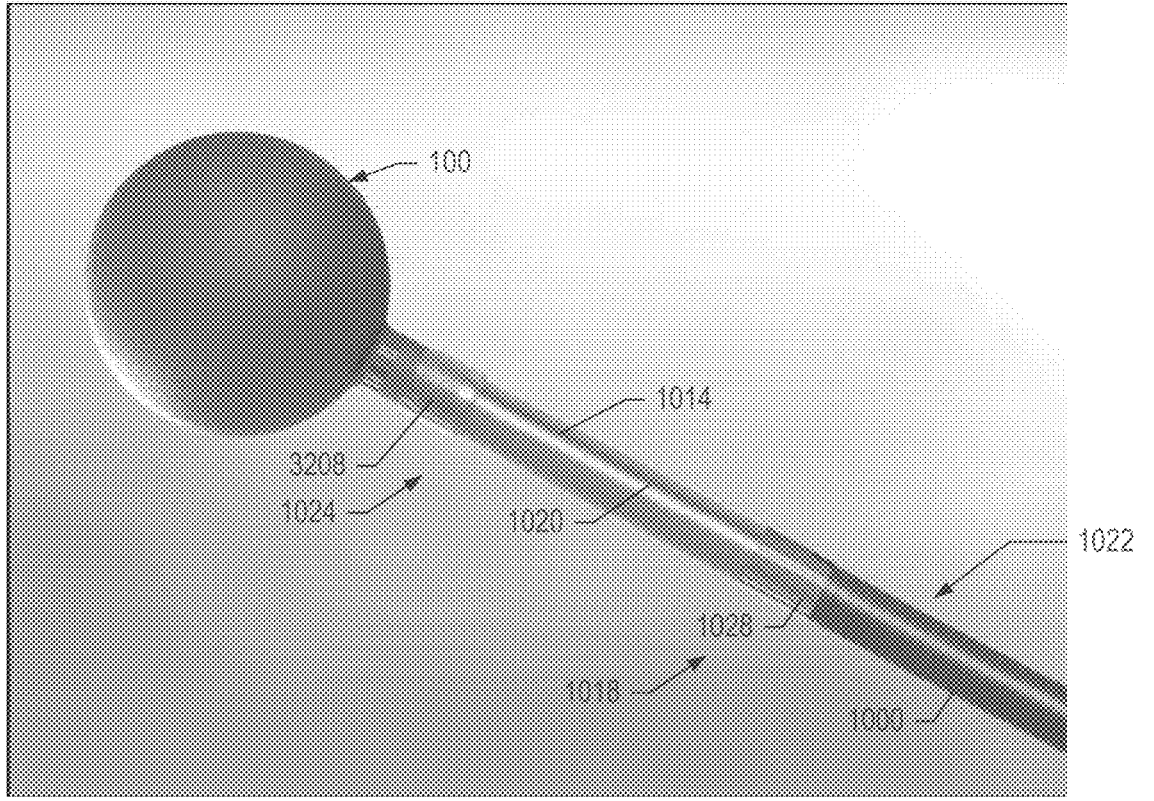

In one embodiment, approximately 0.01 to 5.0 mA of constant current is provided between the anode or working electrode 1014 and a cathode or ground electrode 1016 electrically engaged to one or more conductive cathode rings 1028 bonded to the catheter 1000, as shown in FIG. 29G. Another embodiment of the two electrical conductor arrangement 1008 is shown in FIGS. 29H-I. In this embodiment, the proximal end 1018 of a thermoset polymer segment 1020 is bonded to a distal end 1022 of the catheter 1000, while the distal end 1024 of the thermoset polymer segment is bonded to metallic ring 3208 formed in the neck 116 of the expandable body 100 or 150. The working electrode 1014, in a partial cross-section of the thermoset polymer segment 1020 as shown in FIG. 29H, is embedded within the polymer segment 1020 and bonded to the metallic anode ring 3208. In one aspect, the anode or working electrode 1014 may be bonded directly to the metallic ring 3208 using a silver adhesive or any other suitable adhesive.

In another embodiment, the three electrical conductor arrangement 1010 may be used to provide more control and selectivity in the voltage potential of the working electrode 1014. In addition to the working electrode 1014 and the ground electrode 1016, the three electrical conductor arrangement 1010 includes a reference electrode 1026 and a potentiostat (not shown) that are used to monitor and control the voltage potential of the working electrode relative to the reference electrode. In various embodiments, the reference electrode 1026 is preferably made of platinum, silver, or silver chloride.

By way of example and not limitation, the three electrical conductor arrangement 1010 can be used to detach the expandable body 100 or 150 using a constant current, a constant voltage or an alternating square wave-potential voltage. The anode or working electrode 1014 is modulated based on a comparison between the voltage of the working electrode and the voltage of the reference electrode 1026, which in this embodiment is supported on the delivery catheter. In one embodiment, the potentiostat is configured to provide a voltage in the range between approximately +0.5V and +1.5V at the working electrode 1014 relative to the reference electrode 1026.

In various embodiments, the electrical current travels from the cathode ring 1028 that is supported on the delivery catheter 1000 to a location outside the body of the patient by a conductive electrode 1016 embedded in the wall of the delivery catheter. The electrode 1016 also provides structural reinforcement for the wall of the delivery catheter 1000.

In another embodiment, the expandable body 100 or 150 and the delivery catheter 300 may be joined by one or more non-insulated welds 316, solder, or an adhesive 318, as shown in FIG. 29A. An electrolysis electrical conductor 320, which may be in the form of a wire, or cable that relies on the surrounding electrical insulating material of the catheter wall and/or a dedicated electrical insulating jacket of the electrical conductor itself for electrical insulation, extends along the length of the delivery catheter from the proximal end of the delivery catheter 400 to the distal end of the delivery catheter. The proximal end of the electrical conductor 320 is electrically coupled to a power source or source of electrical current 3100 outside the patient's body. The power source 3100 is also in electrical communication with a needle or electrode patch 3106 on the patient's skin that functions as the cathode for the electrolysis process. The distal end of the electrolysis electrical conductor 320 is coupled to the proximal portion of the expandable body 100 or 150, which is also coupled to the distal portion of the delivery catheter. The expandable body 100 or 150 is functioning as the anode for electrolysis. In this manner, the electrolysis electrical conductor 320 is in electrical communication with the portion 3102 of the expandable body that is not electrically insulated and that is not bonded to the delivery catheter. In various embodiments, the electrolysis electrical conductor 320 can lie within the wall of the delivery catheter 300 as shown in FIG. 29A, along the exterior surface of the delivery catheter, or within a lumen of the delivery catheter.

In some embodiments, the electrolysis electrical conductor 320 is insulated, wherein a proximal portion 3102 of the expandable body 100 or 150 is not insulated, which is similar to detachment site 3302. In some embodiments, the electrolysis electrical conductor 320 and the remainder of the expandable body 100 or 150 and 116 are insulated, while a proximal portion 3102 of the expandable body is not insulated. In other embodiments, the neck 116 of the expandable body 100 or 150 is comprised of metal that can readily undergo electrolysis (such as stainless steel or gold) wherein the remainder of the expandable body is comprised of a metal that does not readily undergo electrolysis, such as platinum. For this embodiment, the platinum portion of the expandable body 100 or 150 need not be insulated. An electrical current or charge is applied to the electrolysis electrical conductor 320 after the expandable body 100 or 150 is expanded. The current is applied in an amount and for a time sufficient to dissolve at least a portion of the non-insulated portion 3102 of the expandable body 100 or 150, resulting in separation of the delivery catheter from the expandable body, leaving the expandable body expanded at the desired position while the delivery catheter 300 is removed.

An electrical current is applied to the electrolysis electrical conductor 320 after the expandable body 100 or 150 is expanded. The current is applied in an amount and for a time sufficient to dissolve at least a portion of the weld or solder and separate the delivery catheter from the expandable body 100 or 150, leaving the expandable body expanded at the desired position while the delivery catheter is removed. In another embodiment, the current is applied in an amount and for a time sufficient to dissolve at least a portion of the expandable body and separate the delivery catheter from the expandable body 100 or 150, leaving the expandable body expanded at the desired position while the delivery catheter is removed. In one embodiment the current is a direct current (DC) while in another embodiment, the current is an alternating current (AC).

Typically, during constant current electrolysis, gas bubbles formed as a byproduct of the electrolysis tend to form an insulating barrier at the detachment site. The gas bubble barrier in combination with an aggregation of non-ionic blood constitutes (fats, proteins, and amino acids, among others) at the detachment site tends to increase impedance at the detachment site and increase the time necessary for detachment, as the rate of electrolysis is decreased. Similarly, blood may begin to clot at the detachment site 3302 further impeding the detachment processes.

Electrolysis is preferably performed when the expandable body 100 or 150 is positioned such that the detachment site 3302 is within a constant stream of ionic blood constituents. For example, when the ballstent 100 is positioned to fill an aneurysm, the detachment site 3302 is positioned such that the detachment site protrudes into the adjacent blood vessel or near the adjacent blood vessel. While in or near the adjacent vessel, the detachment site 3302 is exposed to a constant stream of ionic blood constituents that aid in the electrolysis process to detach the ballstent 100. The constant stream of blood also minimizes the incidence of blood coagulation at the detachment site 3302 during electrolysis, thereby potentially reducing the time required to separate the expanded expandable body 100 or 150 and the deliver catheter.

In another embodiment, voltage controlled electrolysis is performed using an alternating square wave potential voltage. By way of example and not limitation, the potential at the anode or working electrode 1014 alternates between approximately +0.5V and approximately +0.8V, relative to the reference electrode 1026, at a frequency in a range between 0.1 Hz and 10 Hz. In one aspect, the rate at which the voltage potential of the anode or working electrode 1014 varies may be configured to allow for removal of oxides that form on the surface of the anode or working electrode and any aggregation of protein that may form. In this embodiment, oxides are removed during the "depassivation" period of lower voltage while aggregated proteins are removed during the "passivation or hydrolysis" period of higher voltage. The removal of both oxides and aggregated proteins is promoted by the voltage cycling. Therefore, the use of an alternating square wave potential voltage or the use of square wave voltage pulses may allow for a shorter and more consistent detachment times.

In various embodiments, the voltage ranges used to perform voltage controlled electrolysis may vary in response to the composition of the material at the detachment site 3302 and the reference electrode. For example, if the detachment site 3302 is composed of gold and the reference electrode 1026 is composed of platinum then the voltage at the gold anode may alternate between approximately +0.6V and approximately +1.4V relative to the reference electrode at approximately 1 Hz. Conversely, the voltage potential at a detachment site 3302 composed of 304 stainless steel may alternate between approximately +0.1V and approximately +0.4V relative to the platinum reference electrode 1026 at approximately 1 Hz. In one embodiment, the detachments site 3302 is 316L stainless steel. In this embodiment, electrolysis is performed such that the potential at the 316L stainless steel anode alternates between approximately +0.7V and approximately +1.2V relative to the platinum reference electrode 1026 at approximately 1 Hz. In various embodiments, it is desirable for the lower voltage of the alternating square wave voltage potential to be below the hydrolysis potential of water.

Detachment by Thermal Operation

Figure 26B:
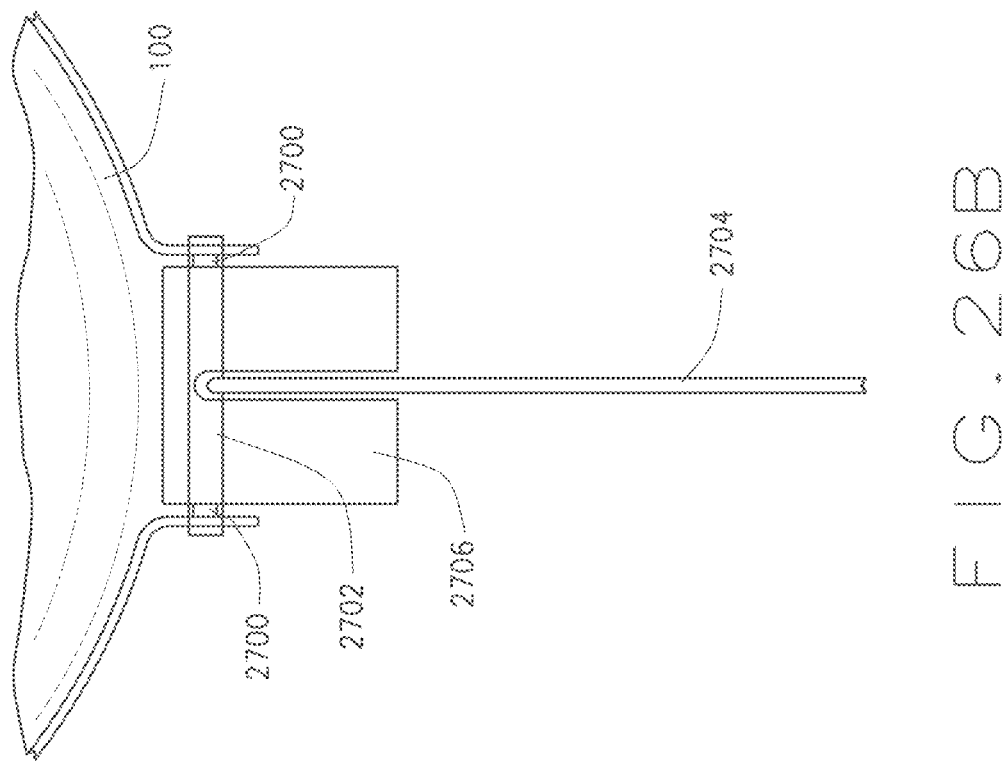
FIGS. 26A-B are a perspective view and plan view, respectively, of an embodiment of the medical device wherein the expandable body is attached to the delivery catheter with an adhesive that can be warmed with a resistive heating element.
Figure 26A:
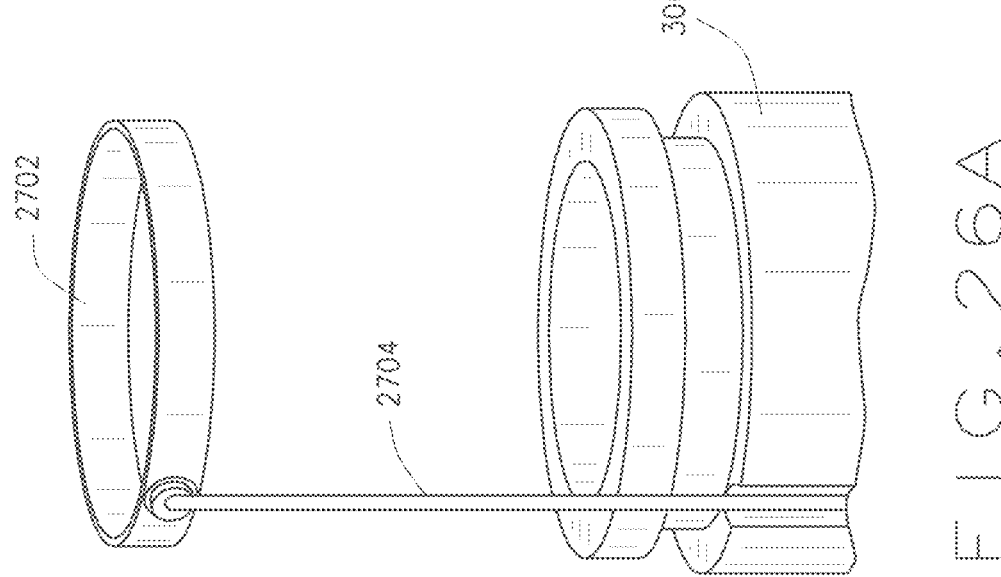

In another embodiment, as shown in FIGS. 26A-B, a mechanical attachment is made between an expandable body and a delivery catheter wherein a portion of the expandable body is attached to the distal portion of the delivery catheter using a binding link 2700. The binding link 2700 may be an adhesive, a metal (e.g. gold foil), a polymer, a polymer binding agent, or other material that reacts to heating (such as with a low melting temperature binding agent) when applied between the hollow cylindrical member 306 of the delivery catheter 400, and the expandable body. The binding link 2700 may also be a tube or ring of temperature-sensitive material (e.g. gold foil, a polymer, or other binding agent) that joins the expandable body 100 or 150 to the delivery catheter. By way of example and not limitation, polymer binding links may be composed of hydrogel polymer, polyurethane, polyethylene terephthalate, polyethylene, high density polyethylene, polyetherethylketone, polyphenylenesulfide, polyolefin, polyolefin elastomer, polyamide, polypropylene, Hytrel®, ethylene vinyl alcohol (EVA), wholly aromatic polyester polymers including liquid crystal polymers (LCP) such as Vectran, and combinations thereof.

After expansion of the expandable body 100 or 150, an electrical current is passed through the resistance heating element 2702 in electrical communication with an electrical conductor (e.g., wire or cable) 2704, resulting in warming or heating of the heat sensitive material that forms the binding link 2700. As the binding link 2700 is heated, the expandable body 100 or 150 may be separated from the delivery catheter 306 through one or more methods. For example, heating the binding link 2700 may cause the link to reach its liquid transition temperature, thereby causing the link to reflow and separate the link. In another example, heating the binding link may weaken the link, by changing the strength of the material. Therefore, if the binding link 2700 is under a tensile load, the increase in temperature will weaken the binding link until it fails under the load. In yet another example, heating the binding link 2700 may cause the link to deform and undergo a significant dimensional change. If the binding link 2700 is heated only at a specific point, the link may undergo a non-symmetric change in geometry, thereby allowing it to transition between a "closed" and an "open" configuration.

In another embodiment, the binding link 2700 may be a collar or other linking structure made of a shape-memory metallic alloy, including but not limited to nitinol, or a shape-memory polymer (SMP). In this embodiment, the binding link 2700 is engaged to the neck 116 of the expandable body 100 or 150. The resistance heating element 2702 is then wrapped around the collar to heat and reshape the collar, which returns to an originally open configuration, thereby releasing the expandable body 100 or 150 from the catheter.

Detachment by Chemical Operation

In another embodiment, a mechanical attachment is made between an expandable body 100 or 150 and a delivery catheter wherein a portion of the expandable body is attached to the distal portion of the delivery catheter using one or more bonds that are sensitive to chemical dissolution. The bonding medium may be composed such that the bonding medium dissolves when contacted by a solution with a high salt concentration, an acid, a base, or a specific chemical. By way of example and not limitation, a cover or other shielding device may be removed from the region where the expandable body 100 or 150 is joined to the delivery catheter to expose the bonding medium. Also by way of example and not limitation, injection or infusion of a solution with a high salt concentration, an acid, a base, or a specific chemical to the region of the bonding, after expansion of the expandable body 100 or 150 at the desire location can result in dissolution of the bonding medium and separation of the expanded expandable body and the delivery catheter.

Detachment by Sonic Operation

In another embodiment, a mechanical attachment is made between an expandable body 100 or 150 and a delivery catheter wherein a portion of the expandable body is attached to the distal portion of the delivery catheter using one or more adhesives, glues, bonds, welds, or solder that are sensitive to sonic waves. In this embodiment, the bond between the expandable body 100 or 150 and the delivery catheter is broken using sound waves, such as focusing pulsed ultrasound waves, resulting in separation of the delivery catheter and the expanded expandable body.

Sealing the Detached Expandable Body

In one embodiment, the wall opening 112 of the expanded expandable body 100 or 150 is left open at the end of the procedure. In other embodiments, the wall opening of the expanded expandable body 100 or 150 is closed prior to the end of the procedure. By way of example and not limitation, the opening 112 may be sealed by applying an external force with the inflation of the balloon portion 1102 of a balloon catheter 1100 adjacent to the expanded expandable body 100 or 150, as shown in FIG. 11. Alternatively, an opening may be sealed by snugging a loop of flexible material around the external surface of the neck of the expandable body 100 or 150 prior to separation of the expanded expandable body and the delivery catheter. In this method, the loop of material may comprise a wire, polymer strand, filament, string, thread, or snare.

Radiopaque Marking of the Expandable Body

According to any of the methods where the expandable body 100 or 150 is separated from delivery catheter, one or more radiopaque markers may be incorporated into the appropriate portions of the expandable body or delivery catheter to assist in the positioning of the expandable body, expansion of the expandable body, separation of the expanded expandable body from the delivery catheter, and removal of the delivery catheter after separation. For example, a radiopaque marker band or spot may be incorporated into the medical device to identify the location where separation is intended or designed to occur. In addition, radiopaque material may be incorporated into the ballstent 100 or the ballstent 150. In addition, a radiopaque spot or marker band may be incorporated into distal end of the delivery catheter so that the tip of the delivery catheter can be visualized under fluoroscopy while pulling the delivery catheter away from the expanded expandable body 100 or 150. A radiopaque spot or marker band may also be placed onto the detachment components, as need be. The radiopaque marker may be comprised of various radiodense materials, including but not limited to a metal band, a metal spot or line, or spot or a line of barium.

In various embodiments, a saccular aneurysm or a blood vessel may be visualized by using a radiopaque dye. The radiopaque dye may be injected prior to introducing the ballstent 100 or the ballstent 150 and can be used to confirm the appropriate size and position for the compressed or expanded ballstent 100 or expanded ballstent 150.

Expandable Body Medical Kit

In various embodiments, a medical kit may be provided for treating a patient with the medical device. The medical kit may include the medical device 500, a guide wire 302, one or more guide catheters 800, one or more expandable body support structures, and methods for separating the expanded expandable body 100 or 150 from the delivery catheter 300 or 400 including separate medical devices for separation, (such as a power source and controller for performing electrolysis or heating a thermally-sensitive binding structure that joins the expandable member 100 or 150 and the delivery device). The medical kit may further include instructions for use. The instructions for use may be provided on the packaging of the medical kit in the form of a label. The instructions for use may be provided in any tangible medium (e.g., paper, CD, DVD, etc.) either separate from the medical kit or contained within the packaging of the medical kit. The instructions for use may be provided via an electronic data feed or via instructions posted on the Internet.

The medical device 3400A can be used as part of various systems, methods, and medical kits. These systems, methods, and medical kits can be used to treat saccular arterial aneurysms, such as a saccular cerebral aneurysm. Alternatively, these systems, methods, and medical kits can be used to treat a variety of medical conditions. In one embodiment, the systems, methods, and medical kits can be used to occlude biological conduits in patients in need thereof, the biological conduits including arteries, veins, vascular structures, ducts, airways, bile ducts, pancreatic ducts, enterocutaneous fistulas, ureters, fallopian tubes, and urethras, among others. The medical kit includes the medical device and instructions for use. The medical kit may also contain additional components for carrying out a variety of treatments using the medical device 500.

Example Methods for Manufacturing a Medical Kit

FIGS. 45-47 are flowcharts of methods to manufacture the expandable body 100 or 150, a delivery catheter 1000, and a medical kit. In one embodiment, a method 4000 for making the expandable body 100 or 150 includes forming the expandable body on a mandrel at step 4002 and coating the expandable body at step 4004. At step 4006, the detachment site and the sites where the conductive wires are bonded to the expandable body 100 or 150 are exposed. The expandable body 100 or 150 is then annealed, folded, wrapped, and annealed again at steps 4008-4012.

A method 4100 to manufacture or otherwise prepare an existing delivery catheter is provided. At step 4102, a coil-reinforced catheter 3402 is obtained and the outer coating is removed from the catheter to expose a portion of the electrical conductors of the coil at step 4104. At step 4106 a portion of the exposed electrical conductors are unwrapped, a cathode ring 1028 is bonded to the catheter 1000 at step 4108, and the exposed electrical conductors are then covered with an insulating material at step 4110. The bonding sites on the catheter 3402 are masked, and the catheter is coated with a hydrophilic or lubricious coating at steps 4112 and 4114. One end of the catheter 3402 is configured for engagement to a fluid source and optionally a source of electrical current. By way example and not limitation, the catheter 1000 may be bonded to a hub that may further include a Luer fitting.

The anode and cathode electrical conductors 1014 and 1016 are bonded to extension electrical conductors, which are then covered in insulating jackets at steps 4118 and 4120. At steps 4122 and 4124, the extension electrical conductors are soldered to an electrical plug, such as the electric terminal 3422, and the soldered joint is covered with an insulating heat-shrink jacket.

As shown in FIG. 47, the method 4200 to assemble the medical device 3400A and a medical kit includes bonding the expandable body 100 or 150 to the catheter 3402 at step 4202. At step 4204, the anode electrical conductor 1014 is bonded to the expandable body 100 or 150 and the exposed conductive surfaces are further insulated at step 4206. Once assembled, the device 3400A is tested at step 4208 and packaged in a medical kit at step 4210.

Example Methods of Using the Expandable Body

Figure 27A:
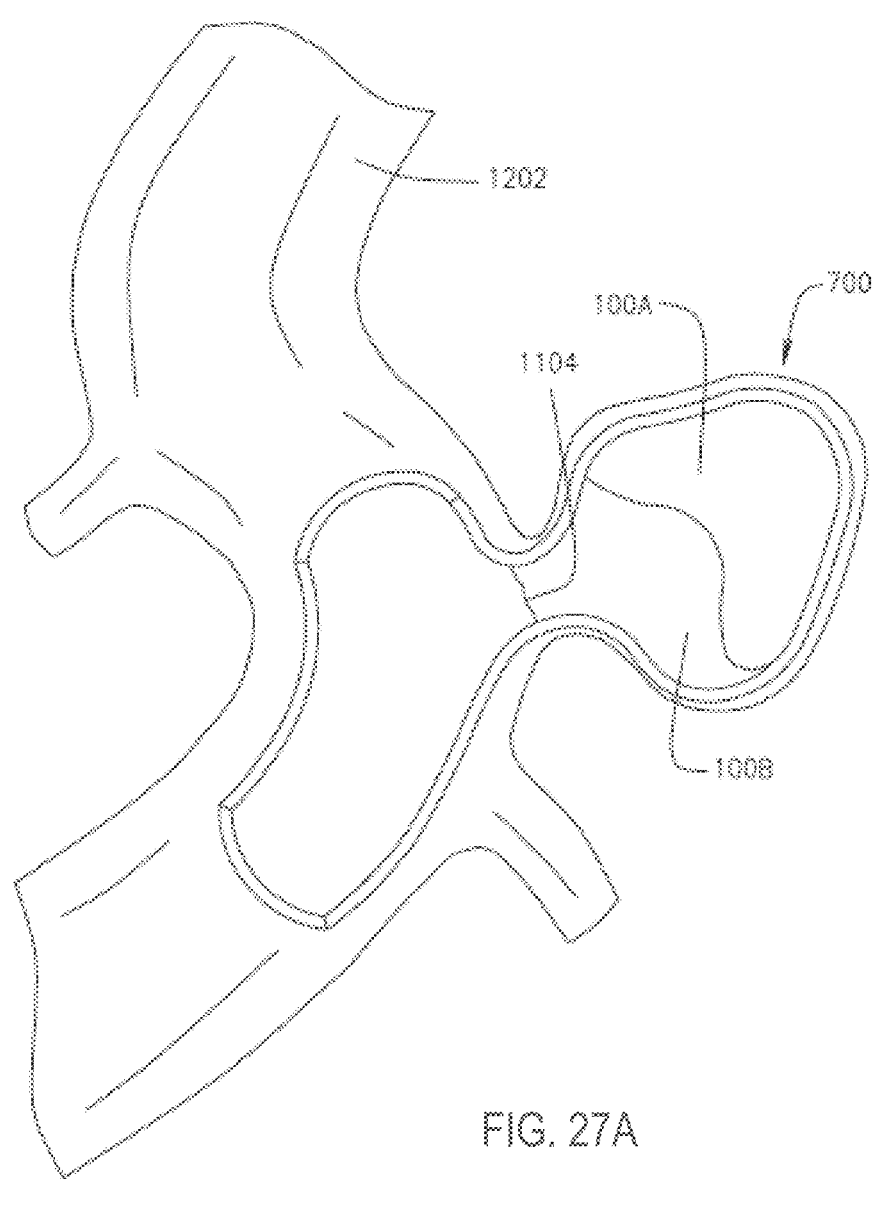
FIGS. 27A-B are plan views an aneurysm filled by two ballstents and a blood vessel filled by two blockstents, respectively.
Figure 27B:
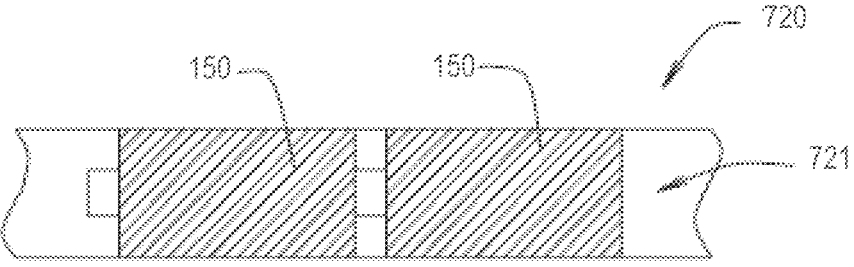

A typical method for using the medical device 3400A to treat a saccular aneurysm includes accessing the vascular system of a human with a needle, passing a guidance member, or guide wire, 302 into the vessel, optionally placing a vascular sheath, advancing the medical device comprising a compressed ballstent 100 and a delivery catheter 300 or 400 and advancing it until the compressed ballstent is located in the lumen 701 of an aneurysm sac 700. Then the ballstent 100 is expanded by passing a fluid, liquid, gas, or solid material, or combinations thereof, through the delivery catheter and into the central void or space 108 of the ballstent. The delivery catheter and the expanded ballstent 100 are then separated and the delivery catheter is removed from the body, while the expanded ballstent remains in place within the lumen 701 of the aneurysm sac 700. The position of the ballstent 100 during and after the procedure may be monitored by any suitable methods, including fluoroscopy, computed tomography, MRI, and ultrasound, including intravascular ultrasound Two or more ballstents 100A-B may be used in combination to fill the lumen or void 701 of the aneurysm sac 700, as illustrated in FIG. 27A, while two or more blockstents 150 may be used in combination to fill the lumen or void 721 of the blood vessel segment 720, as illustrated in FIG. 27B. Additionally, a second, third, or additional expandable bodies 100 or 150 may be required to fill the remaining portion of the aneurysm sac or blood vessel segment not filled by the first ballstent 100A or the first blockstent 150A, respectively.

In various embodiments of the ballstent 100, the shape of a ballstent that has been expanded in the lumen of a saccular aneurysm is determined, in part, by the formed shape of the ballstent. For example, in some embodiments, the ballstent 100 is manufactured into a round, oblong, irregular, or non-spherical orientation to match the contours of the cavity for a particular saccular aneurysm 700. The expanded shape is also determined by the size and shape of the lumen of the saccular aneurysm. The expanded shape can also be determined by the application of an external force, such as by inflating the balloon portion of a balloon catheter adjacent to the expanded ballstent 100. In certain embodiments of the methods, the balloon portion 1102 of a balloon catheter 1100 is inflated in the lumen of the parent blood vessel 1202 adjacent to the expanded ballstent 100 in the lumen of the aneurysm sac, thereby pushing the wall 1104 of the ballstent 100 toward the aneurysm, as shown in FIG. 11A. In other embodiments, the ballstent 100 is manufactured into a non-spherical orientation to match the contours of the cavity for a particular saccular aneurysm 700.

In all embodiments, the expanded shape of the ballstent 100 is determined by the following factors: 1) the manufactured shape of the ballstent 100; 2) the degree of ballstent expansion; 3) the size and shape of the aneurysm 700; and 4) the effect of any applied external force on the ballstent after expansion. By way of example and not limitation, the manufactured size and shape of the ballstent 100 may be determined by making measurements of the aneurysm 700. The measurements can be made by using medical images, including two-dimensional and three-dimensional reconstructions, and standard distance reference markers. Other methods of measuring the aneurysm may also be used.

In another embodiment, the position, size, and shape of the expanded ballstent 100 can be manipulated while positioned within the aneurysm 700. In this embodiment, it is not necessary to determine the precise contours of the aneurysm 700 prior to inserting the ballstent 100. The ballstent 100 is shaped by the degree of expansion of the ballstent and the application of external forces. For example, an external force may be applied by inflating the balloon portion of a balloon catheter adjacent to the expanded ballstent 100, or by tools inserted through or around the delivery catheter 400 or guide catheter 800. In other embodiments, the ballstent 100 may be shaped in a step prior to or after the step of separating the expanded ballstent from the delivery catheter 400.

In various embodiments, the ballstent 100 is designed so that the exterior surface 110 or 124 of the expanded ballstent 100 makes contact with a substantial portion of the inner surface 704 of the aneurysm 700, as shown in FIGS. 4A-E and 8A-E. In some embodiment, the exterior surface 110 or 124 of the ballstent 100 makes contact with at least 50%, 75%, 90% or more of the inner surface 704 of the aneurysm 700, including up to 100%. In embodiments, the expanded ballstent 100 is designed to fill the lumen of the aneurysm sac 701. In one embodiment, the expanded ballstent 100 fills at least 50%, 75%, 90% or more of the volume of the lumen 701 of the aneurysm 700, including up to 100%.

In various embodiments of the blockstent 150, the shape of the blockstent that has been expanded in the lumen of a blood vessel segment is determined, in part, by the formed shape of the blockstent. For example, in some embodiments, the blockstent 150 is manufactured into a cylindrical, oblong, irregular, or non-spherical orientation to match the contours of the lumen, void, or cavity for a particular blood vessel segment 720 or biological conduit segment. The expanded shape is also determined by the size and shape of the lumen, void, or cavity of the blood vessel segment, or biological conduit segment. The expanded shape can also be determined by the application of an external force, such as by inflating the balloon portion of a balloon catheter adjacent to the expanded ballstent 150. In certain embodiments of the methods, the balloon portion 1102 of a balloon catheter 1100 is inflated in the lumen of the parent blood vessel 1202 adjacent to the expanded blockstent 150 in the lumen of the blood vessel or biological conduit, thereby pushing the wall 1104 of the blockstent 150 away from the balloon portion of the balloon catheter, as shown in FIG. 11B. In other embodiments, the blockstent 150 is manufactured into a non-spherical orientation to match the contours of the lumen, void, or cavity for a particular blood vessel segment 720, or biological conduit segment.

In all embodiments, the expanded shape of the blockstent 150 is determined by the following factors: 1) the manufactured shape of the blockstent; 2) the degree of blockstent expansion; 3) the size and shape of the lumen, void, or cavity of the blood vessel segment, or biological conduit segment; and 4) the effect of any applied external force on the blockstent after expansion. By way of example and not limitation, the manufactured size and shape of the blockstent 150 may be determined by making measurements of lumen, void, or cavity to be filled. The measurements can be made by using medical images, including two dimensional and three dimensional reconstructions, and standard distance reference markers. Other methods of measuring the lumen, void, or cavity may also be used.

In another embodiment, the position, size, and shape of the expanded blockstent 150 can be manipulated and configured or changed in vivo or even in situ while positioned within the blood vessel segment 720 or biological conduit. In this embodiment, it is not necessary to determine the precise contours of the lumen, void, or cavity to be filled prior to inserting the blockstent 150. The blockstent 150 is shaped by the degree of expansion of the blockstent and the application of internal and/or external forces. For example, an external force may be applied by inflating the balloon portion of a balloon catheter adjacent to the expanded blockstent, or by tools inserted through or around the delivery catheter 400 or guide catheter 800. In other embodiments, the blockstent 150 may be shaped in a step prior to or after the step of separating the expanded blockstent from the delivery catheter 400.

In various embodiments, the ballstent 150 is designed so that the exterior surface 110 of the expanded blockstent makes contact with a substantial portion of the inner surface 724 of the blood vessel segment 720 as shown in FIGS. 4F-J and 8F-J. In some embodiment, the exterior surface 110 of the blockstent 150 makes contact with at least 50%, 75%, 90% or more of the inner surface 724 of the blood vessel segment 720 including up to 100%. In embodiments, the expanded ballstent 150 is designed to fill the lumen 721 of the blood vessel segment 720. In one embodiment, the expanded blockstent 150 fills at least 50%, 75%, 90% or more of the volume of the lumen 721 of the blood vessel segment 720 including up to 100%.

In all embodiments, the ballstents 100 and blockstents 150 are configured to maintain their expanded shapes. As such, the expanded bodies are not designed for or intended for compression or flattening into disc-like structures before or after separation from the delivery catheter.

An Example Method of Treatment Using the Expandable Body

By way of example and not limitation, as can be understood from FIGS. 2, 3A-B, and 4A-E, a first method of using the device 500 or 3400A to treat a patient may include the steps of examining a patient and collecting diagnostic medical images to identify a saccular aneurysm. The vascular system may be accessed using any suitable method including accessing an artery using the Seldinger technique. A guide wire 302 is then inserted into the vascular system. Then a guide catheter 800 is inserted into the vascular system and advanced into or near the lumen of the saccular aneurysm. The position and luminal dimensions of the saccular aneurysm are then visualized by an intra-arterial injection of radiographic contrast solution under fluoroscopy. The guide wire 302 is removed and the medical device 500 or 3400A is then inserted through the guide catheter 800 until the compressed ballstent 100 is advanced into the lumen 701 of the aneurysm 700. The ballstent 100 is then expanded in the lumen 701 of the aneurysm 700. A radiographic contrast solution may be injected into the parent vessel 1202 of the aneurysm 700 to confirm that the size of the expanded ballstent 100 is appropriate and that it is properly positioned in the aneurysm. Once proper placement and sizing of the expanded ballstent 100 has been confirmed, the expanded ballstent is separated from the delivery catheter 400 by any of the methods disclosed herein, and the delivery catheter is removed. The expanded ballstent 100 is left in the patient, where subsequent examination may be conducted to determine if additional treatment is necessary. The expanded ballstent 100 left in the patient functions to prevent bleeding or expansion of the aneurysm, and as such it alleviates future medical problems the patient might experience had the aneurysm 700 not been treated.

By way of example and not limitation, as can be understood from FIGS. 6, 7A-B, and 8A-E, a second method of using the device 500 or 3400A to treat a patient may include the steps of examining a patient and collecting diagnostic medical images to identify a saccular aneurysm. The vascular system may be accessed using any suitable method including accessing an artery using the Seldinger technique. A guide wire 302 is then inserted into the vascular system. Then a guide catheter 800 is inserted into the vascular system and advanced with the guide wire 302 until the guide wire 302 is positioned in or near the lumen of the saccular aneurysm. The position and luminal dimensions of the saccular aneurysm are then visualized by an intra-arterial injection of radiographic contrast solution under fluoroscopy. The guide catheter 800 is removed and the medical device 500 or 3400A is then inserted over the guide wire 302 until the compressed ballstent 100 is advanced into the lumen 701 of the aneurysm 700. The guide wire 302 is removed. The ballstent 100 is expanded in the lumen 701 of the aneurysm 700. A radiographic contrast solution may be injected into the parent vessel 1202 of the aneurysm 700 to confirm that the size of the ballstent 100 is appropriate and that it is properly positioned in aneurysm. Once proper placement and sizing of the expanded ballstent 100 has been confirmed, the expanded ballstent is separated from the delivery catheter 300 by any of the methods disclosed herein and the delivery catheter is removed. The expanded ballstent 100 is left in the patient, where subsequent examination may be conducted to determine if additional treatment is necessary. The expanded ballstent 100 left in the patient functions to prevent bleeding or expansion of the aneurysm, and as such it alleviates future medical problems the patient might experience had the aneurysm 700 not been treated.

In another embodiment, the ballstent 100 may be rapidly deployed during an emergency. In particular, the ballstent 100 may be deployed rapidly to treat a ruptured cerebral aneurysm, thereby eliminating the need to open the patient's skull prior to treating such an aneurysm.

An Exemplary Method of Treating a Patient Having a Cerebral Aneurysm

A hypothetical method for using the medical device 500 or 3400A to treat a patient having a saccular cerebral aneurysm may begin with one or more pre-surgical consultations, where a number of tests may be performed. The tests may include blood tests, urine tests, an electrocardiogram, and imaging tests including a head CT, a head MRI, and a cerebral angiogram, among others. From the diagnostic imaging tests, images and measurements of the aneurysm may be obtained demonstrating the position, size, and shape of the aneurysm. The consultations may occur several days before, or on the same day, that the procedure is performed.

On the day of the procedure, the patient is prepared for the procedure and typically given local anesthesia. The patient's groin is then prepped and draped in an aseptic manner. Then a physician accesses a femoral artery in the patient with a micropuncture set. A 0.035" soft tip guide wire 302 is inserted in a retrograde fashion into the femoral artery. A 6Fr vascular sheath is placed. A 5Fr diagnostic catheter is advanced over the guide wire until the tip of the 5Fr diagnostic catheter is in the lumen of the saccular cerebral aneurysm, where it can act as a guide catheter 800. While the physician is positioning the guide catheter 800, a surgical assistant prepares the ballstent portion 100 of the medical device by wetting the porous exterior layer 104 of the ballstent with a solution containing thrombin. The medical device 500 or 3400A is advanced through the guide catheter 800 and positioned in the lumen 701 of the aneurysm sac 700. The tip of the guide catheter 800 is pulled back, exposing the compressed ballstent 100. After the compressed ballstent 100 is in the desired position, the compressed ballstent is expanded by injecting a saline solution through the lumen 312 of the delivery catheter 300 or 400 and into the central void 108 of the ballstent until the ballstent expands to fill at least a portion of the aneurysm. The physician obtains an angiogram of the aneurysm 700 and the parent artery 1202 by injection of radiographic contrast material in order to confirm that the expanded ballstent 100 is positioned properly within the lumen 701 of the saccular aneurysm 700 and fills the aneurysm adequately. The physician then connects the proximal end of an electrolysis wire 320 or the insulated conductor wire to a DC power source and applies a current to the electrolysis wire or insulated conductor wire which is electrically coupled to the neck 116 of the ballstent 100 in an amount, and for a time sufficient, to result in the dissolution of a portion of the neck or proximal body 208 of the ballstent that is uncoated and without insulation, resulting in separation of the expanded ballstent and the delivery catheter. The physician obtains another angiogram of the aneurysm 700 and the parent artery 1202 in order to confirm that the expanded, released ballstent 100 is positioned properly within the lumen of the saccular aneurysm and fills the aneurysm adequately. The physician removes the delivery catheter 400, and the guide catheter 800. The physician advances a balloon catheter 1100 over the guide wire 302 until the balloon 1102 is adjacent to the expanded ballstent 100. The balloon portion 1102 of the balloon catheter 1100 is then inflated with a saline solution until it fills the lumen of the parent artery 1202 and flattens and pushes the wall 1104 of the expanded ballstent 100 toward the aneurysm 700. The physician obtains another angiogram of the aneurysm 700 and the parent artery 1202 in order to confirm that the expanded, released ballstent 100 is positioned properly within the lumen of saccular aneurysm, fills the aneurysm adequately, and that the lumen of the parent artery 1202 is free of obstruction. The physician withdraws the balloon catheter 1100, the guide wire 302, and the sheath and achieves hemostasis of the femoral artery puncture with compression. The patient is then transported to a recovery room. During and after recovery, the physician periodically monitors the patient as well as the position of the ballstent 100 and the completeness of the sealing of the aneurysm 700.

It will be appreciated that the devices and methods of the present invention are capable of being incorporated in the form of a variety of embodiments, only a few of which have been illustrated and described above. The disclosures herein may be embodied in other specific forms without departing from its spirit or essential characteristics. The described embodiments are to be considered in all respects only as illustrative and not restrictive and the scope of the present invention is, therefore indicated by the appended claims rather than by the foregoing description. All changes that come within the meaning and range of equivalency of the claims are to be embraced within their scope.

What is claimed is:

1. A medical device, comprising:
   a hollow structure, initially in a pleated and folded configuration, comprising:

a proximal neck and a distal neck;
   a wall with an interior surface that defines a central void, wherein the wall of the hollow structure comprises a polymer layer;
   a proximal opening, defined by the proximal neck that allows for the passage of fluid from a first lumen into the central void; and a distal opening, defined by the distal neck, that allows for the passage of a guidewire through the wall of the hollow structure; wherein:
   the passage of fluid into the central void of the pleated and folded hollow structure results in expansion of the pleated and folded hollow structure;
   at least one metal coil or wire; and wherein;
   the hollow structure, when expanded, assumes a shape wherein the body of the expanded hollow structure is generally round or cylindrical;
   the hollow structure configured to receive the at least one metal coil or wire; into the central void of the hollow structure after expansion of the hollow structure; and
   the expanded hollow structure configured to detach from a catheter, and
   wherein the distal neck of the hollow structure is detachably engaged to a second cylindrical member.

2. The medical device of claim 1, wherein the wall of the hollow structure comprises an interior layer comprising a polymer layer and an exterior layer comprising a metal layer.

3. The medical device of claim 2, wherein the exterior metal layer is a continuous layer.

4. The medical device of claim 2, wherein the exterior metal layer is a discontinuous layer.

5. The medical device of claim 1, wherein the expanded hollow structure comprises a single lobe.

6. The medical device of claim 1, wherein, when expanded, the wall of the proximal neck and the distal neck of the hollow structure is thicker than the wall of the body of the hollow structure.

7. The medical device of claim 1, wherein the proximal neck of the hollow structure configured to fit around a distal end of the catheter.

8. The medical device of claim 1, wherein the hollow structure is formed into pleats, and the pleats are folded or compressed against a portion of the catheter.

9. The medical device of claim 1, wherein the pleated and folded hollow structure can be expanded by injection of a fluid into the central void of the hollow structure from a pressurized fluid source.

10. The medical device of claim 1, wherein the hollow structure is attached or engaged to the catheter by a joining or uniting of components.

11. The medical device of claim 10, wherein one component is fixed to the catheter and a second component is fixed to the proximal neck of the hollow structure.

12. The medical device of claim 10, wherein, after expansion of the hollow structure, the components can be detached, disengaged or separated, resulting in separation of the expanded hollow structure and the catheter.

13. The medical device of claim 1, wherein the hollow structure is attached or engaged to the catheter by a fitting of mechanical parts.

14. The medical device of claim 1, wherein the hollow structure is attached or engaged to the catheter by a physical coupling of mated parts, wherein, after expansion of the hollow structure, the mated parts can be detached, disengaged, or separated, resulting in separation of the expanded hollow structure and the catheter.

15. The medical device of claim 1, wherein the hollow structure and the catheter are configured such that the expanded hollow structure and the catheter can be pulled apart.

16. The medical device of claim 1, wherein the hollow structure and the catheter are configured such that the expanded hollow structure and the catheter can be pulled apart by withdrawing the catheter while the expanded hollow structure is held in place.

17. The medical device of claim 1, comprising a component configured to cause detachment, disengagement, or separation of the catheter and the expanded hollow structure.

18. The medical device of claim 1, configured such that the catheter and the expanded hollow structure can be detached, disengaged, or separated after actuation of a component of the medical device.

* * * * *